United States Patent
Kochi et al.

(10) Patent No.: US 7,067,808 B2
(45) Date of Patent: Jun. 27, 2006

(54) ELECTRON BEAM SYSTEM AND ELECTRON BEAM MEASURING AND OBSERVING METHOD

(75) Inventors: Nobuo Kochi, Tokyo (JP); Hiroyuki Aoki, Tokyo (JP)

(73) Assignee: Topcon Corporation, Tokyo (JP)

( * ) Notice: Subject to any disclaimer, the term of this patent is extended or adjusted under 35 U.S.C. 154(b) by 42 days.

(21) Appl. No.: 10/962,752

(22) Filed: Oct. 13, 2004

(65) Prior Publication Data
US 2005/0161601 A1  Jul. 28, 2005

(30) Foreign Application Priority Data
Oct. 14, 2003 (JP) ............................. 2003-354020
Jun. 17, 2004 (JP) ............................. 2004-180341

(51) Int. Cl.
*G01N 23/00* (2006.01)
(52) U.S. Cl. ..................................... 250/307; 250/310
(58) Field of Classification Search ............. 250/492.2, 250/310, 307, 306; 310/328; 315/366, 382
See application file for complete search history.

(56) References Cited

U.S. PATENT DOCUMENTS

2004/0264764 A1* 12/2004 Kochi et al. ................. 382/154
2005/0061972 A1*  3/2005 Kochi et al. ................. 250/310
2005/0133718 A1*  6/2005 Miyamoto et al. .......... 250/307

FOREIGN PATENT DOCUMENTS

JP  2002-270126 A  9/2002
JP  2002-270127 A  9/2002

OTHER PUBLICATIONS

K. Ebihara, "Medical and Biological Electron Microscope Observation Method," Japanese Society of Electron Microscopy, Jan. 20, 1982 (4th edition: Aug. 20, 1988), pp. 278-299.

* cited by examiner

*Primary Examiner*—Nikita Wells
*Assistant Examiner*—Johnnie L Smith, II
(74) *Attorney, Agent, or Firm*—Foley & Lardner LLP

(57) ABSTRACT

This invention provides an electron beam measuring device capable of performing three-dimensional image measurement of a sample with high precision, irrespective of the tilt angle and height of the sample, by adjusting an electron optical system of a scanning charged-particle beam device so as to be suitable for image measurement. The electron beam measuring device includes a measuring section 20 adapted to tilt a reference template held by a sample holder 3 and an irradiated electron beam 7 relative to each other by means of a sample tilting section 5, to find the shape or coordinate values of the reference template based on a stereo image photographed by an electron beam detecting section 4, a calibration data preparing section 30 for comparing the measuring results at the measuring section 20 with known reference data to prepare calibration data for a stereo image photographed by the electron beam measuring device, and a calibration section 40 for performing a calibration based on the calibration data so as to reduce aberration in an image of the sample detected by the electron beam detecting section 4. Based on the stereo image calibrated by the calibration section 40, the shape or coordinate values of the sample 9 are found.

40 Claims, 42 Drawing Sheets

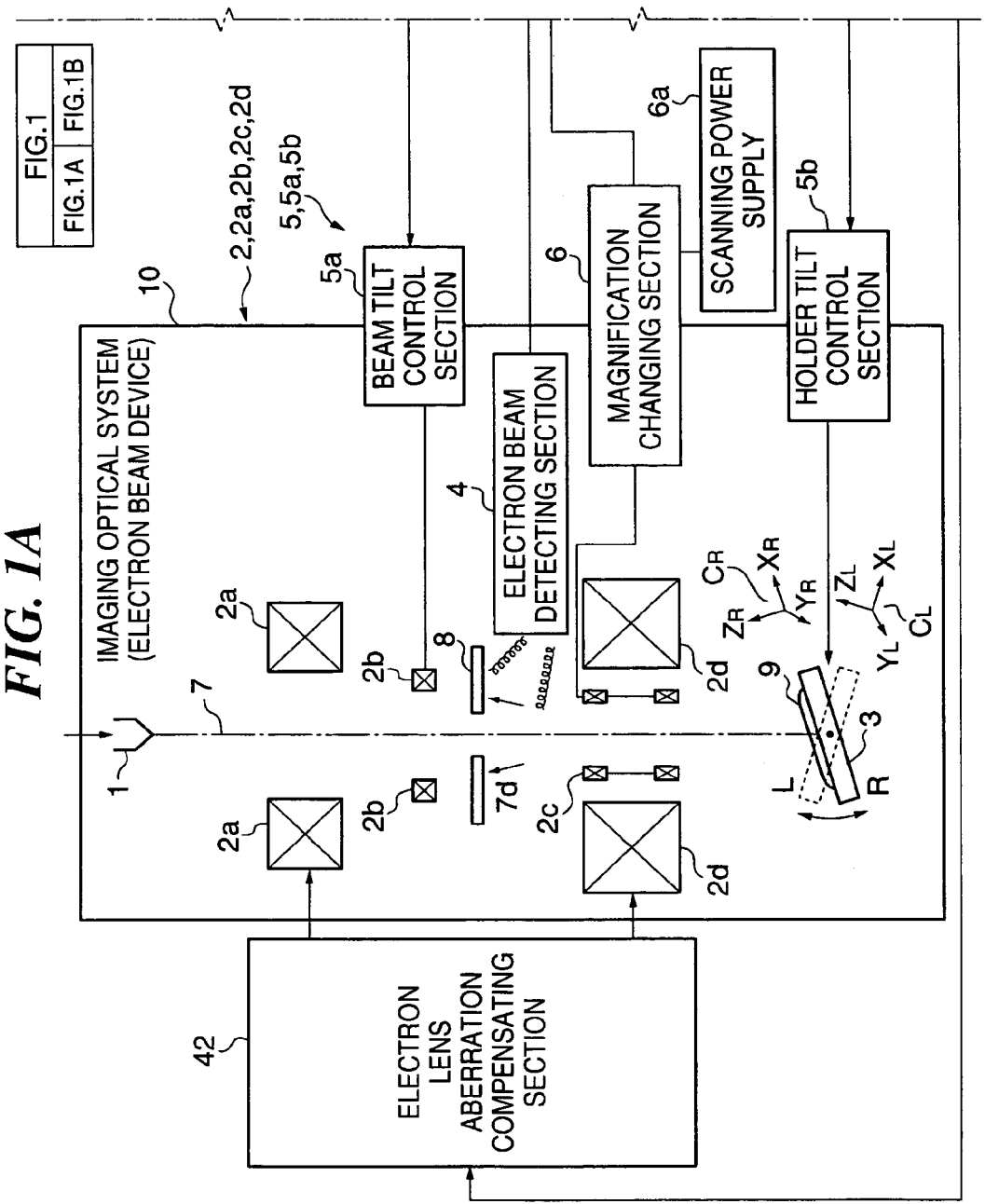

ACQUISITION OF TILTED IMAGES

TWO – DIMENSIONAL REFERENCE TEMPLATE

THREE – DIMENSIONAL REFERENCE TEMPLATE

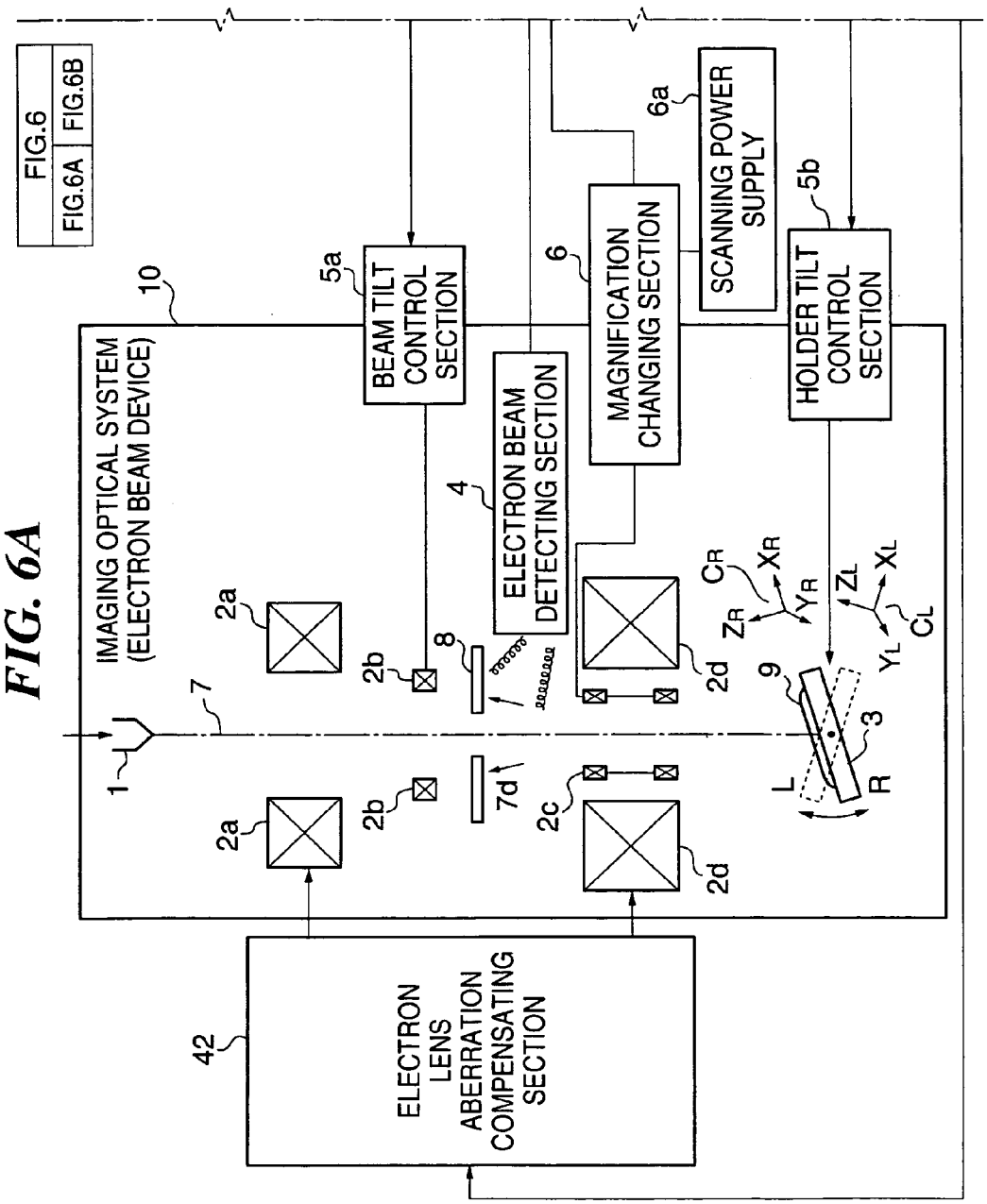

TILTING SAMPLE

WHEN PHOTOGRAPHING ANGLES ARE OPPOSITE WITH RESPECT TO Z- AXIS

WHEN TILT AXIS IS TILTED

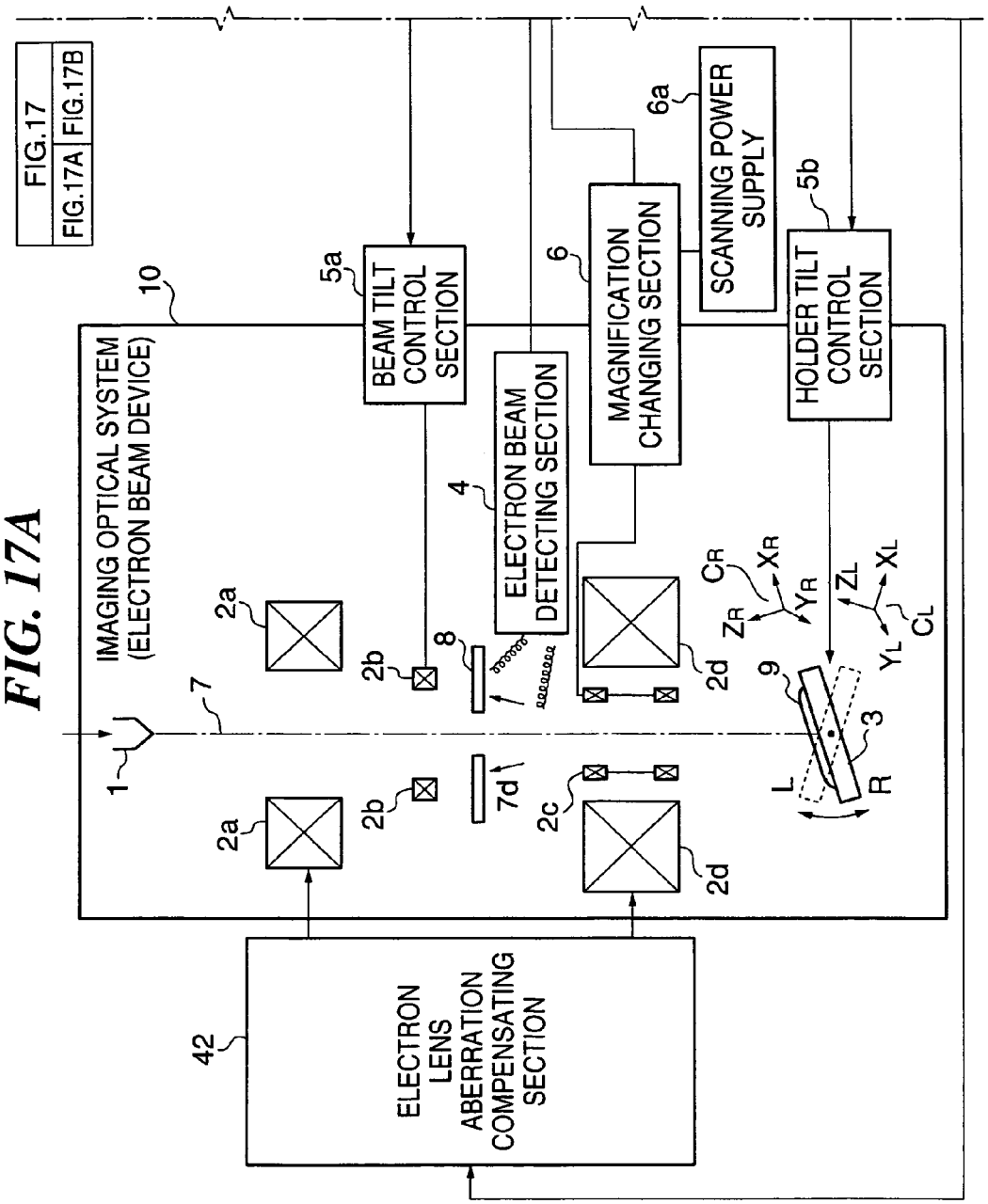

PITCH INTERVAL AND TILT OF REFERENCE TEMPLATE

SIDE SURFACE
OF REFERENCE TEMPLATE

FIG. 23
REFERENCE TEMPLATES
DEALING WITH PLURAL DIRECTIONS
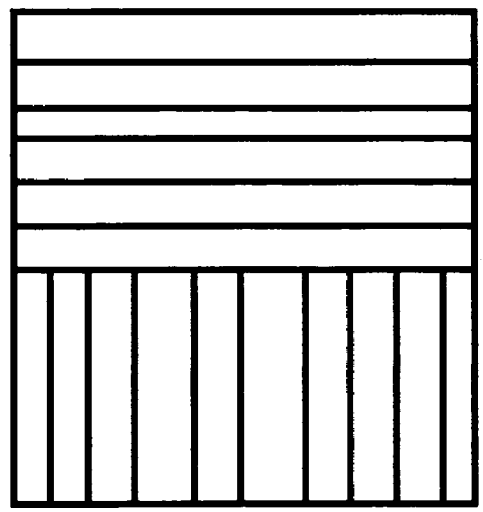
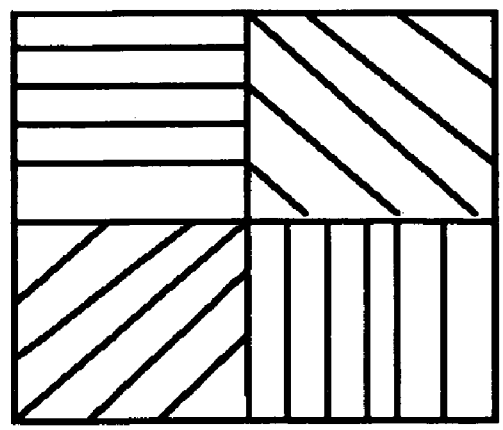

ELECTRON BEAM SYSTEM AND ELECTRON BEAM MEASURING AND OBSERVING METHOD

BACKGROUND OF THE INVENTION

1. Technical Field

This invention relates to an electron beam system and an electron beam measuring method capable of performing three-dimensional measurement of a sample with high precision, using a photographed sample image, and in particular to improvement in adjusting corrections made to an electron optical system of a scanning charged-particle beam device so as to be suitable for image measurement.

This invention relates to an electron beam system and a reference sample for an electron beam system capable of performing three-dimensional measurement of a sample with high precision, using a photographed sample image, and in particular to an electron beam system and a reference sample for an electron beam system capable of adjusting, when the beam or sample of a scanning charged-particle beam device is tilted, corrections made to the angle and magnification and corrections made to an electron optical system, at the time of 3D measurement, so as to be suitable for image measurement.

2. Related Art

In conventional scanning charged-particle beam devices such as scanning electron microscopes (SEM), off-axis aberration of electron lenses is corrected to increase resolution of images from the scanning electron microscopes or the like. Off-axis aberration of the electron lenses is corrected by compensating for spherical aberration, coma, curvature of field aberration, astigmatism, and image surface distortion aberration. For spherical aberration, Scherzer's theorem is known. It is known that spherical aberration cannot be reduced to zero in axisymmetric electron lenses used in the electron microscopes or the like, whether they are an electrostatic type or a magnetic type. Therefore, in order to compensate for spherical aberration, an aspherical mesh or aspherical form is used as the shape of an electrostatic electrode or magnetic pole.

On the other hand, in cases of a transmission electron microscope (TEM), the sample is tilted to obtain transmission images at different tilt angles, and stereo observation is performed using the images as right and left images. In cases of a scanning electron microscope (SEM), the sample or the electron beam is tilted to obtain reflection images at different tilt angles, and stereo observation is performed using the images as right and left images. In the field of semiconductor manufacturing equipment, an electron beam device and a data processing device for an electron beam device are proposed which are capable of appropriately processing stereo detection data obtained from an electron microscope to permit accurate and precise three-dimensional observation of an image of a sample and performing three-dimensional shape measurement of the sample based on the observation.

However, in measuring a sample such as a semiconductor chip or a silicone wafer, in particular, electron beam distortion or magnification distortion dependent on the directions of the tilt and height of the sample may be present. When electron beam distortion or magnification distortion is present in the measuring direction of the sample image, the precision in performing image measurement of the sample varies. In fine processing of semiconductor in recent years, the width of the patterns formed on a chip, for example, is as small as in the order of submicrons, and the margin of dimensional error acceptable in three-dimensional shape measurement has been increasingly small as compared with the past. Therefore, conventional methods for compensating for off-axis aberration of electron lenses such as spherical aberration cannot achieve the precision necessary for stereo image measurement.

In the 3D measurement of a sample such as a semiconductor chip or a silicone wafer, in particular, it is necessary to accurately find the tilt angle of the beam or sample and the magnification at the time of measurement and photographing. Also, there may be electron beam distortion or magnification distortion dependent on the directions of the tilt and height of the sample. When the tilt angle or magnification is not accurate or when electron beam distortion or magnification distortion is present in the measuring direction of the sample image, the values used in the image measurement of the sample are not correctly found and the precision further varies. In fine processing of semiconductor in recent years, the width of the patterns formed on a chip, for example, is as small as in the order of submicrons, and the margin of dimensional error acceptable in three-dimensional shape measurement has been increasingly limited as compared with the past. Therefore, conventional methods for the approximate tilt angle value or magnification and for compensating off-axis aberration of electron lenses such as spherical aberration cannot achieve the precision necessary for stereo image measurement.

This invention has been made to solve the foregoing problems, and it is therefore an object of this invention to provide an electron beam device and a reference sample for an electron beam device capable of performing image measurement of a sample with high precision, irrespective of the tilt angle and height of the sample.

SUMMARY OF THE INVENTION

In order to achieve the object above, an electron beam system according to this invention comprises, as shown in FIG. 1 for example, an electron optical system 2 for irradiating an electron beam emitted from an electron beam source 1 on a sample 9, a sample holder 3 for holding the sample 9, a sample tilting section 5 for tilting the sample holder 3 and the irradiated electron beam 7 relative to each other so that a stereo image can be acquired, and an electron beam detecting section 4 for detecting an electron beam 7 outgoing from the sample 9, and has the following composition. That is, the system comprises a first measuring section (for example, measuring section 20) for finding a shape or coordinate values of the reference template held by the sample holder based on a stereo image of the reference template photographed by the electron beam detecting section 4 while the reference template and the irradiated electron beam are tilted relative to each other by the sample tilting section 5, a calibration data preparing section 30 adapted to compare measurement results of the reference template by the first measuring section with known reference data on the reference template, to prepare calibration data for a stereo image photographed by the electron beam detecting section, a calibration section 40 for performing a calibration based on the calibration data so as to reduce aberration in an image of the sample detected by the electron beam detecting section 4, and a second measuring section (for example, a shape/coordinate measuring section 50) for finding a shape or coordinate values of the sample 9 based on a stereo image, photographed by the electron beam detecting section 4, of the sample 9 placed in a tilt state made by the sample tilting section 5 on the sample holder 3, where the sample 9 is calibrated by the calibration section 40. This electron beam system may be referred to as an electron beam measuring device.

In a device constituted as described above, an electron beam device of the electron beam system includes the electron beam source 1, the electron optical system 2, the sample holder 3, the sample tilting section 5, and the electron beam detecting section 4. The first measuring section photographs a reference template in a specific tilt state by means of the electron beam detecting section 4, to find the shape or coordinate values of the reference template based on an acquired stereo image. The calibration data preparing section 30 compares the measurement results of the reference template by the first measuring section with known reference data on the reference template, to prepare calibration data for a stereo image photographed by the electron beam detecting section. The calibration section 40 performs a calibration based on the calibration data so as to reduce aberration in an image of the sample detected by the electron beam detecting section 4. The second measuring section finds the shape or coordinate values of the sample 9 based on the stereo image, photographed by the electron beam detecting section 4, of the sample 9 placed in a tilt state created by the sample tilting section 5 on the sample holder 3, where the sample 9 is calibrated by the calibration section 40. In this manner, three-dimensional image measurement of a sample can be performed with high precision, irrespective of the tilt angle and height of the sample, by adjusting an electron optical system of a scanning charged-particle beam device so as to be suitable for image measurement.

Preferably, as shown for example in FIG. 6, the electron beam system according to this invention further comprises a correction factor storing section 64 for storing correction factors for a stereo image, photographed by the electron beam detecting section 4, for a plurality of tilt states made by the sample tilting section 5; and an image correcting section 60 adapted to read a correction factor corresponding to a tilt state in which the stereo image is photographed from the correction factor storing section 64, to correct the stereo image. And, the second measuring section (for example, a shape/coordinate measuring section 50) includes an approximate measurement section 52 for finding an approximate shape or coordinate values of the sample 9 photographed in the stereo image, and a precise measurement section 54 for finding a shape or coordinate values of the sample 9 based on the stereo image corrected by the image correcting section 60; and the image correcting section 60 is configured to correct the stereo image based on the shape or coordinate values of the sample 9 found by the approximate measurement section 52 and using the correction factor read from the correction factor storing section 64.

In order to achieve the object above, an electron beam system according to the present invention is, as shown for example in FIG. 1, an electron beam measuring device comprising an electron optical system 2 for irradiating an electron beam 7 emitted from an electron beam source 1 on a sample 9, a sample holder 3 for holding the sample 9, a sample tilting section 5 for tilting the sample holder 3 and the irradiated electron beam 7 relative to each other so that a stereo image can be acquired, and an electron beam detecting section 4 for detecting an electron beam 7 outgoing from the sample 9, and has a following composition. That is, the electron beam system comprises a first measuring section (for example, measuring section 20) for finding a shape or coordinate values of the reference template held by the sample holder 3 based on a stereo image of the reference template photographed by the electron beam detecting section 4 while the reference template and the irradiated electron beam 7 are tilted relative to each other by the sample tilting section 5; a calibration data preparing section 30 adapted to compare measurement results of the reference template by the first measuring section with known reference data on the reference template, to prepare calibration data for a stereo image photographed by the electron beam detecting section; a calibration section 40 for performing a calibration based on the calibration data so as to reduce aberration in an image of the sample detected by the electron beam detecting section 4; a second measuring section (for example, a shape/coordinate measuring section 50) for finding a shape or coordinate values of the sample 9 based on a stereo image, photographed by the electron beam detecting section 4, of the sample 9 placed in a tilt state made by the sample tilting section 5 on the sample holder 3, where the sample 9 is calibrated by the calibration section 40; and an image display section 28 for displaying a stereo image of the sample 9 based on the electron beam detected by the electron beam detecting section 4.

Preferably, in the electron beam system according to the present invention, as shown for example in FIG. 1 and FIG. 16, the sample tilting section 5 is configured to tilt the sample holder 3 and the irradiated electron beam 7 relative to each other in at least one of a first sample tilt mode where the irradiation direction of the electron beam irradiated by the electron optical system 2 is changed with respect to the sample 9 and a second sample tilt mode where the sample holder 3 is tilted with respect to the electron beam.

Preferably, in the electron beam system according to the present invention, the calibration data preparing section 30 prepares calibration data on the tilt amount by the sample tilting section 5; and the calibration section 40 calibrates the tilt amount by the sample tilting section 5.

Preferably, in the electron beam system according to the present invention, the calibration data preparing section 30 prepares calibration data on the irradiation direction of the electron beam 7 irradiated by the electron optical system 2; and the calibration section 40 calibrates the irradiation direction of the electron beam 7 irradiated by the electron optical system 2.

Preferably, in the electron beam system according to the present invention, the calibration data preparing section 30 prepares calibration data on the magnification of the electron optical system 2; and the calibration section 40 calibrates the scanning range of the electron optical system 2.

Preferably, in the electron beam system according to the present invention, the calibration data preparing section 30 prepares calibration data on distortion correction for the electron optical system 2; and the calibration section 40 calibrates the scanning direction of a scan coil of the electron optical system 2.

In order to achieve the object above, an electron beam measuring method according to the present invention uses, as shown for example in FIG. 4, an electron beam system including an electron optical system 2 for irradiating an electron beam emitted from an electron beam source 1 on a sample 9, a sample holder 3 for holding the sample 9, a sample tilting section 5 for tilting the sample holder 3 and the irradiated electron beam 7 relative to each other so that a stereo image can be acquired, and an electron beam detecting section 4 for detecting an electron beam 7 outgoing from the sample 9, and has the following steps. That is, a computer is caused to perform: a first measuring step (S102, S104, S106) of finding a shape or coordinate values of the reference template held by the sample holder 3 based on a stereo image of the reference template photographed by the electron beam detecting section 4 while the reference template and the irradiated electron beam 7 are tilted relative to each other by the sample tilting section 4; a calibration data preparing step (S108) of comparing measurement results of the reference template in the first measuring step with known reference data on the reference template, to prepare calibration data for a stereo image photographed by the electron beam detecting section; a calibration step (S110) of performing a calibration based on the calibration data so as to reduce aberration in an image of the sample detected by the electron beam detecting section 4; and a second measuring step (S112, S114, S116) of finding a shape or coordinate values of the sample 9 based on a stereo image, photographed by the electron beam detecting section 4, of the sample 9 placed in a tilt state made by the sample tilting section 5 on the sample holder 3, where the sample 9 is calibrated in the calibration step.

In order to achieve the object above, an electron beam measuring method according to the present invention uses, as shown for example in FIG. 7, an electron beam system including an electron optical system 2 for irradiating an electron beam 7 emitted from an electron beam source 1 on a sample 9, a sample holder 3 for holding the sample 9, a sample tilting section 5 for tilting the sample holder 3 and the irradiated electron beam 7 relative to each other so that a stereo image can be acquired, and an electron beam detecting section 4 for detecting an electron beam 7 outgoing from the sample 9, and has the following steps. That is, a computer is caused to perform: a first measuring step (S202, S204, S206) of finding a shape or coordinate values of the reference template held by the sample holder based on a stereo image of the reference template photographed by the electron beam detecting section 4 while the reference template and the irradiated electron beam 7 are tilted relative to each other by the sample tilting section 5; a calibration data preparing step (S208) of comparing measurement results of the reference template in the first measuring step with known reference data on the reference template, to prepare calibration data for a stereo image photographed by the electron beam detecting section; a calibration step (S210) of performing a calibration based on the calibration data so as to reduce aberration in an image of the sample detected by the electron beam detecting section 4; a correction factor storing step (S212) of storing correction factors for a stereo image, photographed by the electron beam detecting section 4, for a plurality of tilt states made by the sample tilting section 5; an approximate measurement step (S214, S216, S218) of finding an approximate shape or coordinate values of the sample 9 based on a stereo image, photographed by the electron beam detecting section 4, of the sample 9 placed in a tilt state made by the sample tilting section 5 on the sample holder 3, where the sample 9 is calibrated in the calibration step; an image correcting step (S220, S22) of reading a correction factor corresponding to a tilt state in which the stereo image is photographed from the correction factors stored in the correction factor storing step and applying the correction factor to the shape or coordinate values of the sample 9 found in the approximate measurement step to correct the stereo image; and a precise measurement step (S224) of finding a shape or coordinate values of the sample 9 based on the stereo image corrected in the image correcting step.

In order to achieve the object above, an electron beam measuring method according to the present invention uses, as shown for example in FIG. 4, an electron beam system including an electron optical system 2 for irradiating an electron beam 7 emitted from an electron beam source 1 on a sample 9, a sample holder 3 for holding the sample 9, a sample tilting section 5 for tilting the sample holder 3 and the irradiated electron beam 7 relative to each other so that a stereo image can be acquired, and an electron beam detecting section 4 for detecting an electron beam 7 outgoing from the sample 9, and has the following steps. That is, a computer is caused to perform: a first measuring step (S102, S104, S106) of finding a shape or coordinate values of the reference template held by the sample holder 3 based on a stereo image of the reference template photographed by the electron beam detecting section 4 while the reference template and the irradiated electron beam 7 are tilted relative to each other by the sample tilting section 5; a calibration data preparing step (S108) of comparing measurement results of the reference template in the first measuring step with known reference data on the reference template, to prepare calibration data for a stereo image photographed by the electron beam detecting section; a calibration step (S110) of performing a calibration based on the calibration data so as to reduce aberration in an image of the sample detected by the electron beam detecting section 4; a second measuring step (S112, S114, S116) of finding a shape or coordinate values of the sample 9 based on a stereo image, photographed by the electron beam detecting section 4, of the sample 9 placed in a tilt state made by the sample tilting section 5 on the sample holder 3, where the sample 9 is calibrated in the calibration step; and an image displaying step (S118) of displaying a stereo image of the sample 9 based on the electron beam detected by the electron beam detecting section 4.

In order to achieve the object above, an electron beam system according to the resent invention is, as shown for example in FIG. 17, an electron beam measuring device comprising: an electron optical system 2 for irradiating the electron beam 7 emitted from an electron beam source 1 on a sample 9; a sample holder 3 for holding the sample 9; a sample tilting section 5 for tilting the sample holder 3 and the irradiated electron beam 7 relative to each other so that a stereo image can be acquired; and an electron beam detecting section 4 for detecting an electron beam 7 outgoing from the sample 9, and has the following constitution. That is, the device includes a third measuring section (for example, a shape/coordinate measuring section 50) for finding a shape or coordinate values of the sample 9 based on an output corresponding to the acquired stereo image in the tilt state made by the sample tilting section 5; a first measuring step of finding a shape or coordinate values of the reference template based on a signal corresponding to the stereo image outputted from the electron beam detecting section 4 while the reference template held by the sample holder 3 and the irradiated electron beam are tilted relative to each other; a correction factor storing section 64 adapted to compare measurement results of the reference template by the first measuring section with the identified reference data on the reference template, to store a correction factor for a space other than a tilted surface to which the sample 9 is tilted by the sample tilting section 5; and an image correcting section 60 adapted to read a corresponding correction factor from the correction factor storing section 64 to correct the image.

Then, the third measuring section performs, as shown for example in FIG. 17 and FIG. 18, an approximate measurement step (S402) of finding an approximate shape or coordinate values of the sample 9 based on the output corresponding to the stereo image from the electron beam detecting section 4, the image correcting section 60 performs an image correcting step (S404, S406) of reading a corresponding image correction factor from the correction factor storing section 64 to correct the image based on the shape or coordinate values of the sample 9 found in the approximate measurement step, and the third measuring section performs a precise measurement step (S408) of finding a shape or coordinate values of the sample 9 based on the corrected stereo image corrected by the image correcting section 60.

In order to achieve the object above, an electron beam system comprises, as shown for example in FIG. 19, an electron beam source 1 for emitting an electron beam; an electron optical system 2 for converging the electron beam 7 emitted from the electron beam source 1 and irradiating the electron beam 7 on a sample 9; a detecting section 4 for receiving an electron 7d from the sample 9 on which the electron beam 7 is irradiated; a sample holder 3 for holding the sample 9; a sample tilting section 5 (5a, 5b) for tilting the electron beam 7 irradiated on the sample 9 held by the sample holder 3 and the sample 9 relative to each other; a data processing section 20 adapted to receive, for each tilt angle, a signal detected by the detecting section 4 receiving an electron from a reference sample 9a having at least two tilted surfaces and held by the sample holder 3 so as to be free in the relative tilt, to find a tilt angle of the reference sample 9a based on an image of the two tilted surfaces and a reference dimension of the reference sample 9a; and so on.

In the electron beam system, the data processing section may be configured to further find a magnification of an image of the sample.

Furthermore, the data processing section may be configured to find a correction factor for a tilt amount of the sample based on the found tilt angle, to correct the tilt angle based on the correction factor for the tilt amount of the sample. The sample herein typically refers to a measuring object.

The data processing section may be configured to find a correction factor for a tilt amount of the sample between tilt angles where a measurement is performed based on a plurality of found tilt angles, to correct a tilt amount of the sample for a tilt angle other than the tilt angles where a measurement is performed.

In order to achieve the object above, an electron beam system comprises, as shown for example in FIG. 19, an electron beam source 1 for emitting an electron beam; an electron optical system 2 for converging the electron beam 7 emitted from the electron beam source 1 and irradiating the electron beam 7 on a sample; a detecting section 4 for receiving an electron from the sample 9 on which the electron beam 7 is irradiated; a sample holder 3 for holding the sample 9; a sample tilting section 5 (5a, 5b) for tilting the electron beam 7 irradiated on the sample 9 held by the sample holder 3 and the sample 9 relative to each other; and a data processing section adapted to receive, for each tilt angle, a signal detected by the detecting section 4 receiving an electron from a reference sample 9a having at least two tilted surfaces and held by the sample holder 3 so as to be free in the relative tilt, to perform a process of finding a tilt angle of the reference sample 9a based on an image of the two tilted surfaces derived from an image of the sample in a position where little displacement in the electron optical system occurs due to tilting of the sample 9 and a reference dimension of the reference sample 9a, and a process of finding a correction factor based on a difference between a magnification in a neighboring image at the tilt angle and a magnification in an image according to the detected signal. This electron beam system typically performs angle measurement and image correction of electron lens distortion, scanning distortion, and the like, and typically performs parallel projection.

In the electron beam system, the sample tilting section 5 may be configured to perform either tilt control 5b of the sample holder 3 (for example, FIG. 19) for allowing the sample 9 to tilt relative to the electron beam 7, or deflection control 5a of the electron beam 7 (for example, FIG. 28) for allowing the electron beam 7 to be irradiated at different angle relative to the sample 9.

The data processing section may include an image forming section 24 for forming an image of the sample in which electron lens distortion, scanning distortion, and/or the like are corrected using the correction factor and based on a signal from the electron beam detecting section. The sample herein typically refers to a measuring object. The electrons detected by the electron beam detecting section 4 may include secondary electrons and reflected electrons.

In the electron beam system, the data processing section may be configured to find by interpolation a correction factor for a tilt angle where a measurement is not performed in addition to a correction factor for a tilt angle where a measurement is performed.

In order to achieve the object above, the reference sample 9a used in the present invention has a pattern including a bottom portion, a top portion, and a side surface portion connecting therebetween at a predetermined taper angle, where a dimension of a respective portion, an angle of the side surface portion and a height are known.

The reference sample 9a may be configured with a line-and-space pattern.

The reference sample 9a may formed with a line-and-space pattern in a direction perpendicular to a tilt direction of the sample.

According to the electron beam system of this invention, the calibration data preparing section compares the measurement results of the reference template by the first measuring section with known reference data on the reference template, to prepare calibration data for a stereo image photographed by the electron beam measuring device, and the calibration section performs a calibration based on the calibration data so as to reduce aberration in an image of the sample detected by the electron beam detecting section 4. Therefore, three-dimensional image measurement of a sample can be performed with high precision, irrespective of the tilt angle and height of the sample, by adjusting an electron optical system of a scanning charged-particle beam device so as to be suitable for image measurement.

Also, according to the electron beam system and the reference sample for an electron beam system of this invention, the tilt angle, magnification, and distortions involved with the electron optical system, for example, can be calculated and corrected, thereby rectifying a photographed image and allowing measurement of a sample with high precision.

The basic Japanese Patent Applications No. 2003-354020 filed on Oct. 14, 2003 and No. 2004-180341 filed on Jun. 17, 2004 are hereby incorporated in its entirety by reference into the present application.

The present invention will become more fully understood from the detailed description given hereinbelow. The other applicable fields will become apparent with reference to the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiments. Among the disclosed changes and modifications, those which may not literally fall within the scope of the present claims constitute, therefore, a part of the present invention in the sense of doctrine of equivalents.

The use of the terms "a" and "an" and "the" and similar referents in the context of describing the invention (especially in the context of the following claims) are to be construed to cover both the singular and the plural, unless otherwise indicated herein or clearly contradicted by context. The use of any and all examples, or exemplary language (e.g., "and the like") provided herein, is intended merely to better illuminate the invention and does not pose a limitation on the scope of the invention unless otherwise claimed.

BRIEF DESCRIPTION OF THE DRAWINGS

FIG. 1A and FIG. 1B are general block diagrams illustrating the structure of a first embodiment of this invention.

FIG. 6A and FIG. 6B are block diagrams illustrating the structure of a second embodiment of this invention.

FIG. 17A and FIG. 17B are general block diagrams illustrating the structure of a fourth embodiment of this invention.

FIG. 21 illustrates the pitch interval and tilt of the reference template of FIG. 20. The figure shows the shape of depressions and projections, or an interval L between the depressions and projections (in cases of a line-and-space pattern, a pitch interval L) and a height h of the depressions and projections, a taper angle Φ, and so on.

FIG. 23 illustrates examples of a reference template with the reference templates as shown in FIG. 20 mounted thereon in a plurality of directions.

DETAILED DESCRIPTION OF THE PREFERRED EMBODIMENT

Principle

Figure 2A:
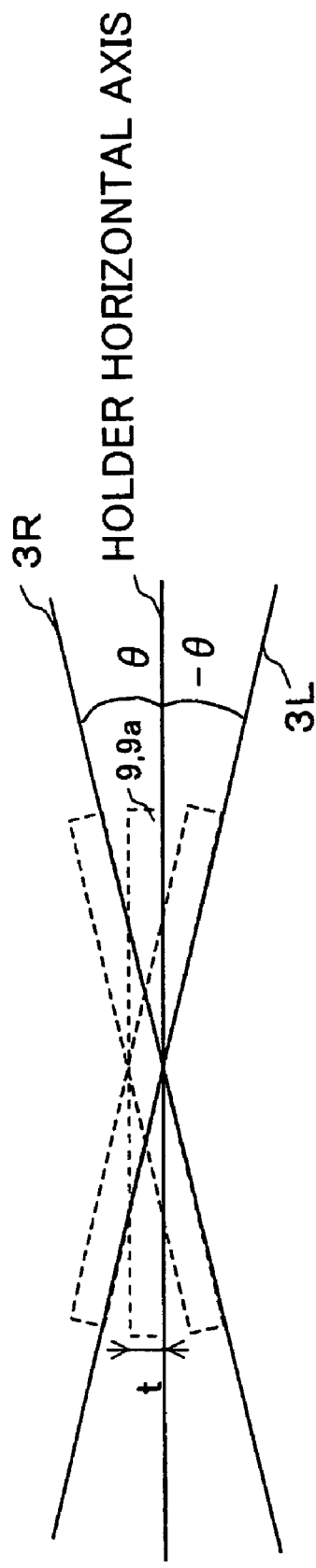
FIG. 2A and FIG. 2B are diagrams illustrating tilt states of a sample holder of an electron beam measuring device.
Figure 2B:
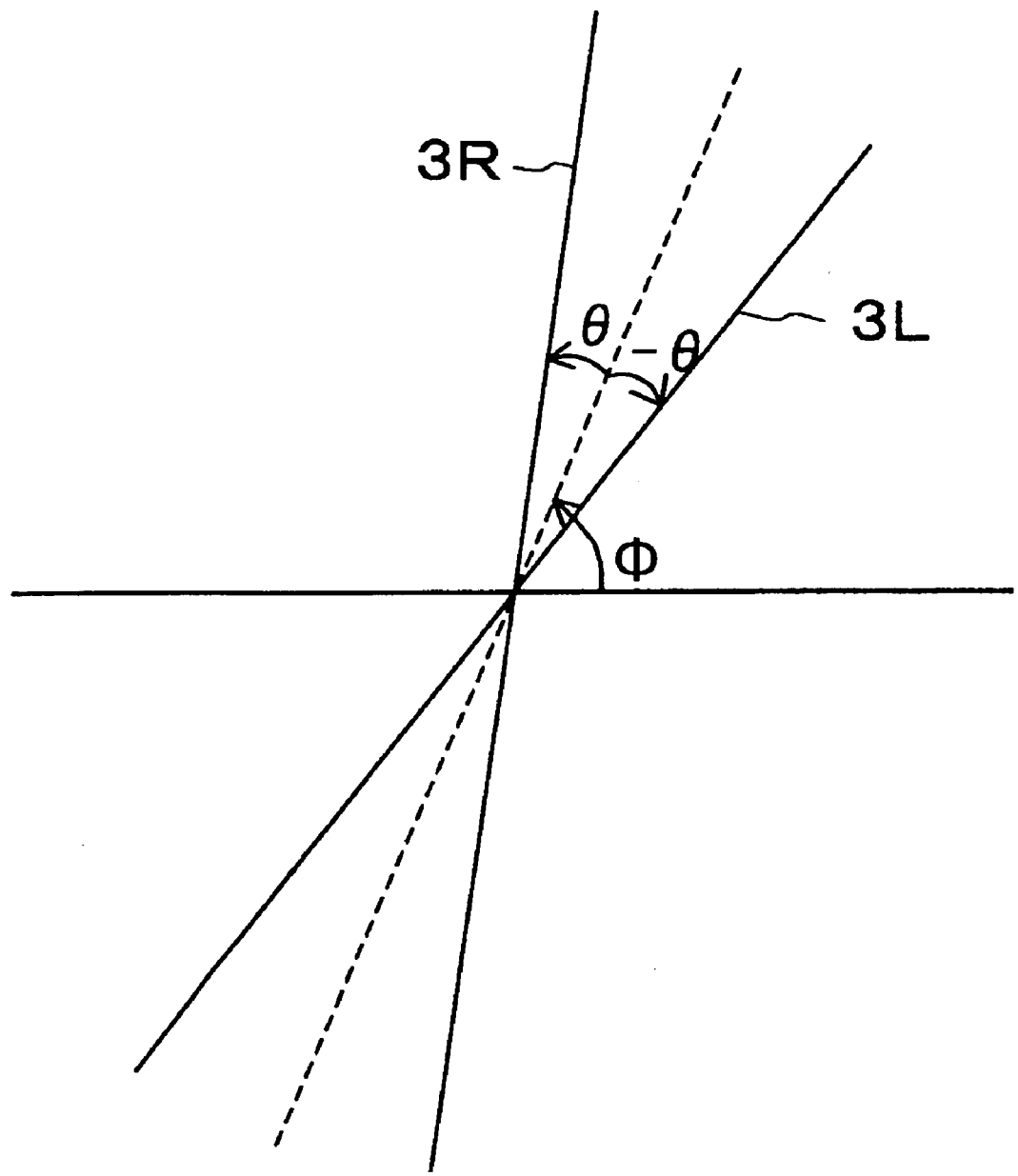

With reference to FIGS. 2 and 3, a description is made below of the principle of this invention. FIG. 2 is a diagram illustrating tilt states of a sample holder of an electron beam measuring device as an electron beam system. In the figure, 2A shows a case where a tilt state is achieved with a horizontal state as a standard state and 2B shows a case where a tilt state is achieved with a certain tilt state as a standard state. For tilt states of a sample holder 3, there are a first mode where the sample holder 3 is tilted at an arbitrary angle (±θ) from a horizontal state as a standard state (see FIG. 2A), and a second mode where the sample holder 3 is tilted at an arbitrary angle (±θ) from a state where it is tilted at a specific angle (Φ) as a standard state (see FIG. 2B). When the sample holder 3 is in a tilt state, the angle between a reference template 9a or a sample 9 placed on the sample holder 3 and an electron beam incident on it is adjusted so that the electron beam measuring device can acquire right and left images of the sample necessary for stereo image measurement. The thickness of the reference template 9a is represented by t.

Figure 3A:
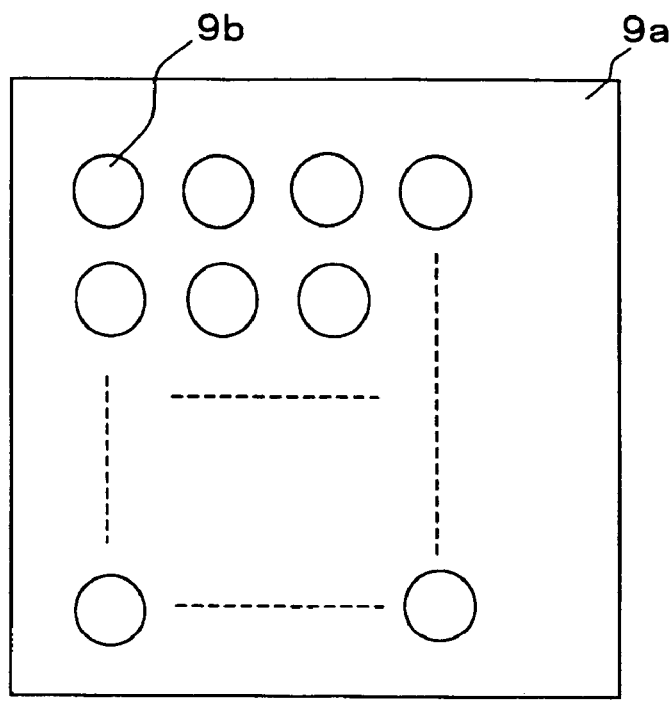
FIGS. 3A and 3B respectively illustrate a two-dimensional reference template and a three-dimensional reference template.

FIG. 3A is a diagram illustrating the distribution of targets arranged on a two-dimensional reference template. A plurality of precisely measured targets 9b are arranged on a two-dimensional reference template 9a. The targets 9b, which may also be referred to as measurement reference points or characteristic points, are marks formed on a surface of the reference template 9a in an easily viewable manner. The reference template 9a can assume a horizontal attitude or a tilted attitude while placed on the sample holder 3 of the electron beam device 10 (see FIG. 1).

Figure 3B:
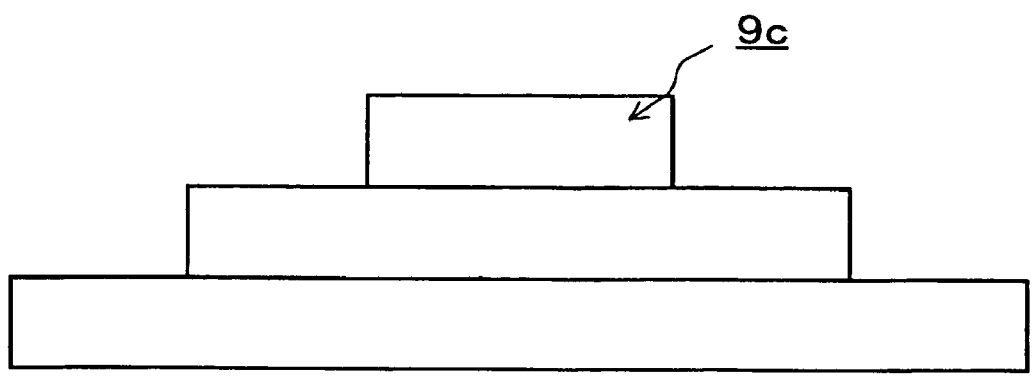

FIG. 3B is a diagram illustrating a three-dimensional reference template. Here, the three-dimensional reference template has a configuration in which three two-dimensional reference templates are stacked. In a three-dimensional reference template, the height of a reference template 9c is equal to the total of the thicknesses of the two-dimensional reference templates. The three-dimensional reference template 9c is placed on the sample holder 3 and can be brought into an arbitrary tilt state. Here, an arbitrary tilt state means the condition setting the tilt state of the three-dimensional reference template 9c to an angle selected for a space where a measuring object can be present, so as to perform the calibrating of the measuring object in the space. When the three-dimensional reference template 9c in such an arbitrary tilt state is photographed, image distortion in the height direction can be calculated using the reference targets at different heights included in the photographed image. Then, compensation values for magnetic potentials or electrostatic potentials of an electron optical system of the electron beam measuring device are calculated to compensate for the calculated image distortion values in the height direction, and a calibration is performed to reduce aberration in an image of the sample detected by an electron beam detecting section 4 of the electron beam measuring device. A calibration can then be achieved with respect to the space in the height direction (for example, in the optical axis direction).

With a device constituted as described above, the electron beam measuring device acquires the positions of the targets in the image of the reference template at each tilt angle, and acquires calibration data for removing image distortion in the height direction of the reference template. Then, a sample 9 is placed on the sample holder 3 in place of the reference template, and an image of the sample 9 as a subject is acquired at an arbitrary tilt angle by the electron beam measuring device.

When image distortion inevitable in image measurement still remains even after calibrating the electron beam measuring device in this manner, an image correcting section 60 (see FIG. 6) is used to correct an image of the sample 9 based on the approximate height and position of the sample 9. That is, each tilt angle of the reference template 9a used to correct the electron beam measuring device 2 can be known from the approximate height and position of the subject (sample 9), and image distortion in every part of the subject at the tilt angle can be calculated based on the image distortion pattern at the tilt angle. Image distortion in every part of the subject is calculated with respect to its entirety for each subject, and the image of the sample 9 is corrected to compensate for the image distortion. Alternatively, image distortion may be calculated as an image distortion pattern at each height (space) of the electron beam measuring device so that the image distortion pattern can be stored in a memory of the electron beam measuring device. That is, using positional information on the targets on the reference template 9a as shown in FIG. 3A, a distortion factor of the targets on the reference template 9a at each tilt angle can be acquired.

First Embodiment

Figure 1B:
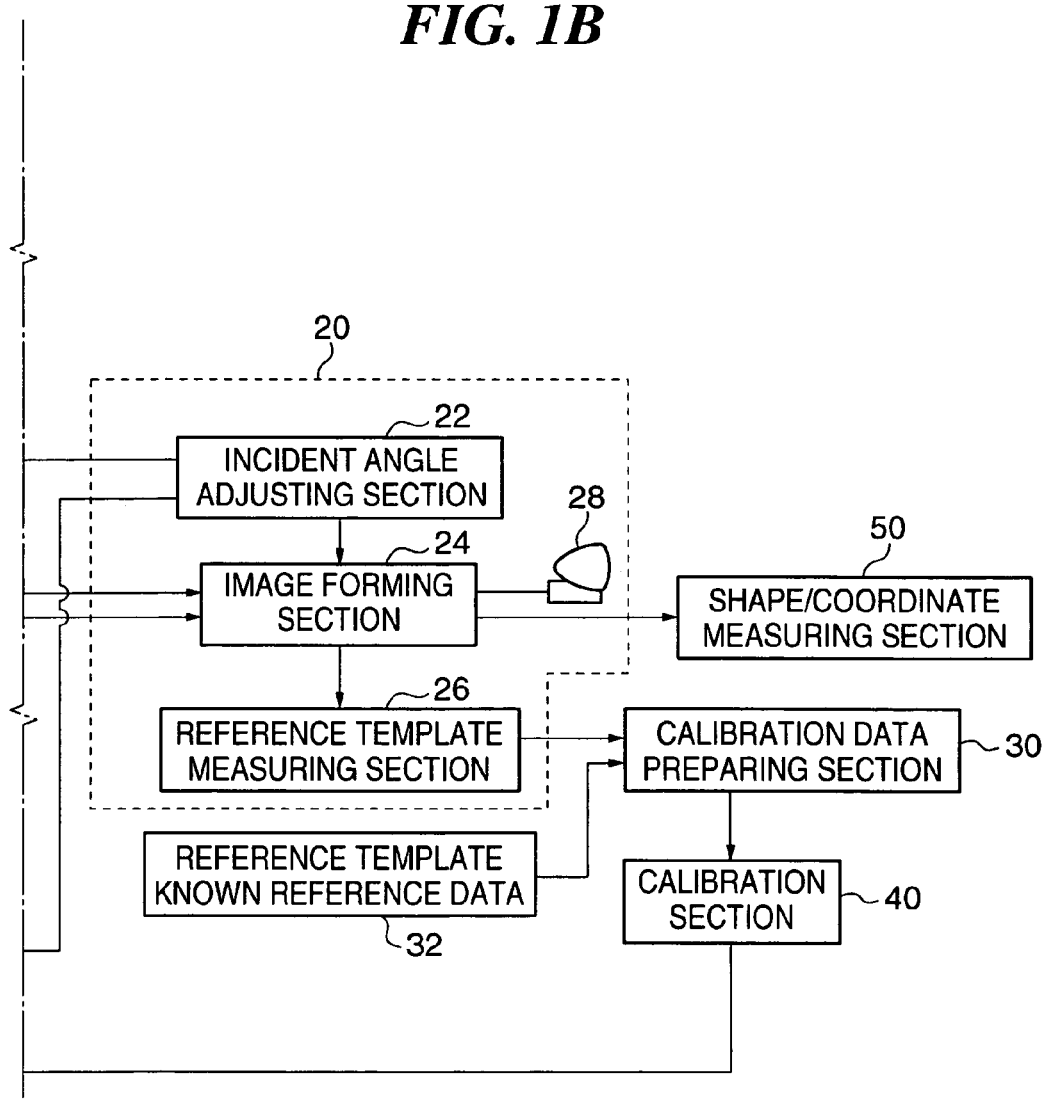

With reference to FIG. 1, an embodiment of this invention will be described hereinafter. FIG. 1 is a block diagram illustrating the structure of a first embodiment of this invention. In the first embodiment, the rotational angle of a holder for holding an object is adjusted to adjust the tilt angle of the object so that a stereo image of the object can be obtained. As shown in the figure, an electron beam device 10 (scanning electron microscope) as an imaging optical system in an electron beam measuring device as an electron beam system includes an electron beam source 1 for emitting an electron beam 7, an electron optical system 2 for irradiating the electron beam 7 on an object 9, a sample holder 3 for tiltably holding the object 9, a magnification changing section 6 for changing the magnification of the electron optical system 2, a scanning power supply 6a for supplying electric power to the magnification changing section 6, a detector 4 for detecting the electron beam 7, a holder tilt control section 5b as a tilt control section 5 for controlling the tilt of the sample holder 3, and a secondary electron converting target 8 for attenuating the energy of secondary electrons outgoing from the object 9 to reflect the secondary electrons toward the detector 4. A beam tilt control section 5a as the tilt control section 5 for controlling the tilt of the electron beam 7 is not used in the first embodiment but used in a third embodiment described later.

The electron optical system 2 includes condenser lenses 2a for changing the electron flow density, divergence angle and irradiation area of the electron beam 7 emitted from the electron beam source 1, deflection lenses 2b for controlling the incident angle of the electron beam 7 on a sample surface, scanning lenses 2c for deflecting the electron beam 7 with a reduced diameter to cause it to scan the sample surface two-dimensionally, and objective lenses 2d which focus the incident probe beam on the sample surface and serve as condenser lenses in the final stage. The area on the sample surface which the scanning lenses 2c cause the electron beam 7 to scan is determined according to a magnification change command from the magnification changing section 6. The beam tilt control section 5b transmits a tilt control signal to the sample holder 3 to switch it between a first attitude 3L in which it makes a first tilt angle relative to the irradiated electron beam 7 and a second attitude 3R in which it makes a second tilt angle relative to the electron beam 7.

A three-dimensional coordinate system $C_L$ of the object 9 placed on the sample holder in the first attitude 3L can be represented as $(X_L, Y_L, Z_L)$ in a fixed coordinate system of the electron beam device 10. Also, a three-dimensional coordinate system $C_R$ of the object 9 placed on the sample holder in the second attitude 3R can be represented as $(X_R, Y_R, Z_R)$ in a fixed coordinate system of the electron beam device 10. Although the holder tilt control section 5b can switch the tilt angle of the sample holder 3 relative to the irradiated electron beam 7 between an angle R tilted upward to the right and an angle L tilted upward to the left in the figure, the sample holder 3 may be configured to be tilted at a multiplicity of angles, not limited to two angles. At least two angles are necessary to obtain stereo detection data. When a yaw axis, a pitch axis and a roll axis, for example, are set as a three-dimensional coordinate system of the object 9, the yaw axis, the pitch axis and the roll axis correspond to Z-axis, X-axis and Y-axis, respectively.

The object 9 is a chip of a semiconductor material such as a silicon semiconductor or a gallium arsenide semiconductor, or may be an electronic component such as a power transistor, a diode or a thyristor, or may be a display device component using glass such as a liquid crystal panel or an organic EL panel. Under typical observing conditions for a scanning electron microscope, the electron beam source 1 is set to a potential of −3 kV and the object 9 to −2.4 kV. Secondary electrons released from the object 9 are attenuated in energy as they collide with the secondary electron converting target 8 and detected by the detector 4.

The electron beam measuring device includes a measuring section 20 as a first measuring section, a calibration data preparing section 30, a known reference data storing section 32, a calibration section 40, an electron lens aberration compensating section 42, and a shape/coordinate measuring section 50 as a second measuring section.

The measuring section 20 is adapted to tilt the reference template 9a, 9c held by the sample holder 3 relative to the irradiated electron beam 7 by means of the sample tilting section 5, to find the shape or coordinate values of the reference template 9a, 9c based on a stereo image of the reference template 9a, 9c photographed by the electron beam detecting section 4. The measuring section 20 has an incident angle adjusting section 22, an image forming section 24, a reference template measuring section 26, and a display device 28.

The incident angle adjusting section 22 adjusts the attitude of the object 9 (including the reference template 9a, 9c), to adjust the incident angle of the electron beam 7 projected from the electron beam device 10 onto the object 9 relative to the object 9 so that a stereo image of the object 9 can be formed. That is, the incident angle adjusting section 22 transmits a control signal to the holder tilt control section 5b to adjust the attitude of the object 9. In addition, the incident angle adjusting section 22 transmits a control signal to the holder tilt control section 5b to adjust a reference surface to be scanned by the electron beam 7 emitted from the electron beam source 1 so that right and left images necessary to form a stereo image can be formed. The image forming section 24 forms an image of the sample surface using a secondary electron beam detected by the detector 4 when the electron beam 7 is caused to scan a region on the sample surface by the scanning lenses 2c. The reference template measuring section 26 finds the shape or coordinate values of the reference template 9a, 9c based on the stereo image of the reference template 9a, 9c photographed by the electron beam detecting section 4. The display device 28 is adapted to display right and left images constituting the stereo image of the object 9 (including the reference template 9a, 9c) photographed by the electron beam detecting section 4. A CRT or liquid crystal display, for example, may be used as the display device 28.

The calibration data preparing section 30 compares the measurement results of the reference template by the measuring section 20 with known reference data on the reference template 9a, 9c, to prepare calibration data for a stereo image photographed by the electron beam measuring device. The known reference data storing section 32 stores the positions of the targets provided on the reference template 9a, 9c. Calibration data for the electron beam measuring device prepared by the calibration data preparing section 30 may include:

(1) calibration data on the tilt amount by the sample tilting section 5,
(2) calibration data on the irradiation direction of the electron beam 7 irradiated by the electron optical system 2,
(3) calibration data on the magnification of the electron optical system 2, and
(4) calibration data on distortion correction for the electron optical system 2.

The calibration section 40 performs a calibration based on the calibration data so as to reduce aberration in an image of the sample detected by the electron beam detecting section 4. Depending on the foregoing calibration data for the electron beam measuring device prepared by the calibration data preparing section 30, the calibration section 40 may be configured to:

(1) calibrate the tilt amount by the sample tilting section 5,
(2) calibrate the irradiation direction of the electron beam 7 irradiated by the electron optical system 2,
(3) calibrate the scanning range of the electron optical system 2, and
(4) calibrate the scanning direction of a scan coil of the electron optical system 2.

The electron lens aberration compensating section 42 compensates for the distribution states of magnetic potentials and electrostatic potentials of the electron lenses constituting the electron optical system 2 according to a calibration signal outputted from the calibration section 40 so as to reduce aberration in an image of the sample, thereby adjusting the electron optical system 2 to be suitable for image measurement. The electron beam device 10 may have an electromagnetic prism called ExB that separates secondary electrons emitted from the sample 9, from the electron beam 7 emitted from the electron beam source 1, to send the secondary electrons to the electron beam detecting section 4. In such cases, the electron optical system 2 as an object of calibration by the calibration section 40 should include such an electromagnetic prism called ExB.

The shape/coordinate measuring section 50 finds the shape or coordinate values of the sample 9 based on the stereo image, photographed by the electron beam detecting section 4, of the sample 9 placed in a tilt state made by the sample tilting section 5 on the sample holder 3, where the sample 9 is calibrated by the calibration section 40. The shape/coordinate measuring section 50 uses the incident angle adjusting section 22, the image forming section 24, and the display device 28 of the measuring section 20, in common with the reference template measuring section 26.

Figure 4:
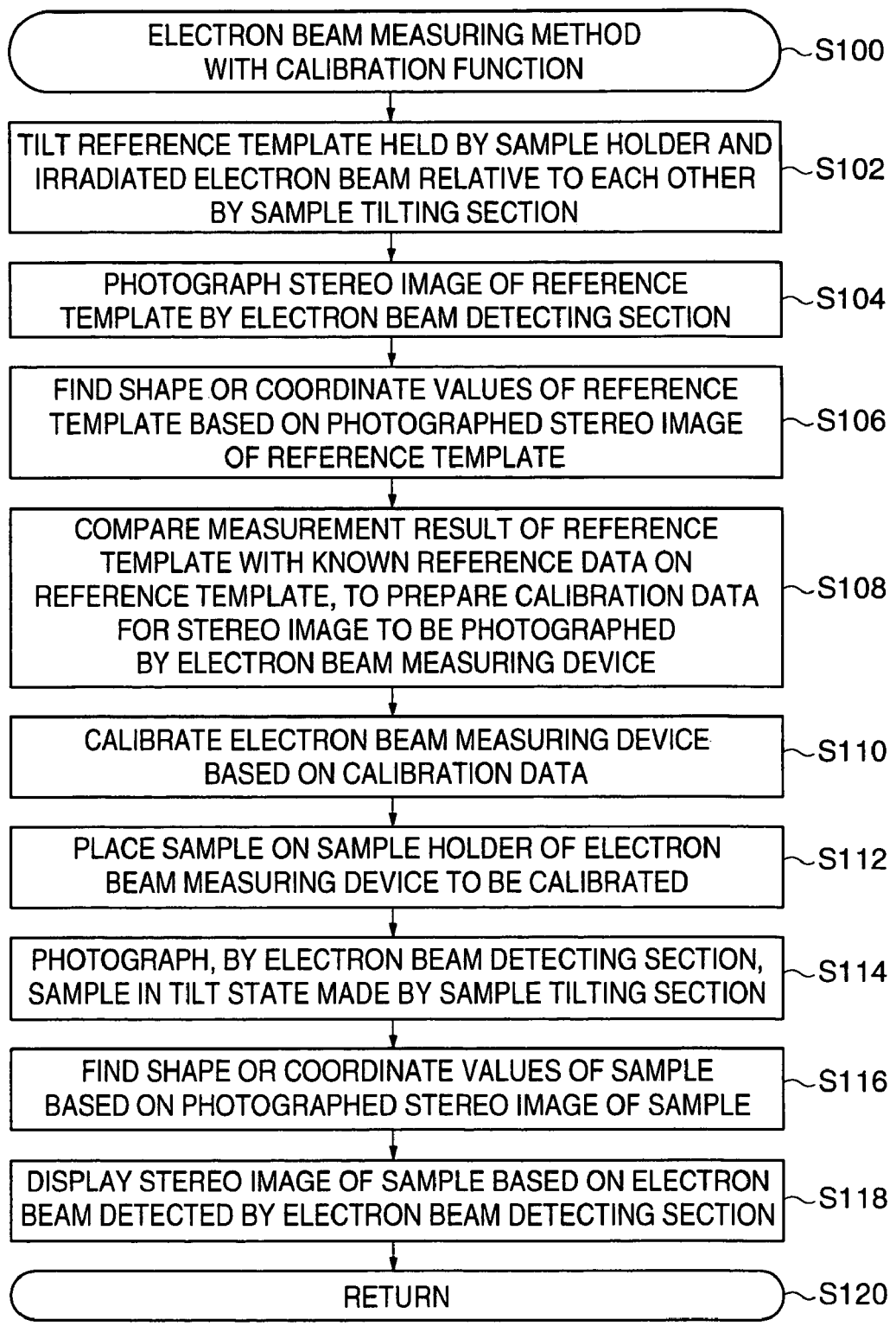
FIG. 4 is a flowchart of electron beam measurement including the calibration procedure for an electron beam device according to the first embodiment of this invention.

With reference to FIG. 4, a description is made of the calibration procedure for an electron beam device necessary for stereo image measurement by an device constituted as described above. FIG. 4 is a flowchart of electron beam measurement including the calibration procedure for the electron beam device according to the first embodiment of this invention. FIG. 4 shows a process flow of calibration of the electron beam device using the reference template 9a, 9c, and of subsequent measurement of an image of the sample (S100). A reference template 9a, 9c is placed on the sample holder 3, to bring the sample holder 3 or the electron beam 7 into a tilt state (S102). For example, the beam tilt control section 5b transmits a tilt control signal to the sample holder 3 and the incident angle adjusting section 22 adjusts the incident angle of the electron beam 7 relative to the object 9. The tilt angle is set with respect to the tilt angle of the reference template 9a, 9c to be measured. For example, the tilt angle is set to the tilt state shown in FIG. 2A or FIG. 2B. When there are a plurality of tilt angles, an image may conveniently be acquired at all the tilt angles at which a measurement may possibly be performed.

The measuring section 20 acquires a tilted image of the reference template 9a, 9c from the electron beam detecting section 4 (S104). The measuring section 20 finds the shape or coordinate values of the reference template 9a, 9c based on the stereo image of the reference template 9a, 9c photographed by the electron beam detecting section 4 (S106). Target detection and a stereo matching process described later may conveniently be used in S106.

The calibration data preparing section 30 compares the measurement results of the reference template 9a, 9c in S106 with known reference data on the reference template 9a, 9c, to prepare calibration data for a stereo image photographed by the electron beam device 10 (S108). The calibration section 40 performs a calibration of the electron beam device 10 based on the calibration data so as to reduce aberration in an image of the sample detected by the electron beam detecting section 4 (S110).

Then, a sample (measuring object) 9 is placed on the sample holder 3 (S112). The electron beam 7 or the sample holder 3 is brought into a desired tilt state, to allow the sample 9 to be photographed by the electron beam detecting section 4 (S114). As the desired tilt state, an angle at which much of the sample 9 can be viewed with minimum blind spots or an angle at which the targets particularly desired to be measured can be satisfactorily photographed may be selected, for example, when three-dimensional image measurement of the sample 9 is performed. The shape or coordinate values of the sample 9 are found based on the stereo image of the sample 9 in the desired tilt state (S116). In order to allow an observation of the sample, the stereo image of the sample 9 is displayed on the display device 28 based on the electron beam detected by the electron beam detecting section 4 (S118). The process is returned when the shape or coordinate values of the sample 9 can be acquired (S120).

Parallel Projection

Figure 5:
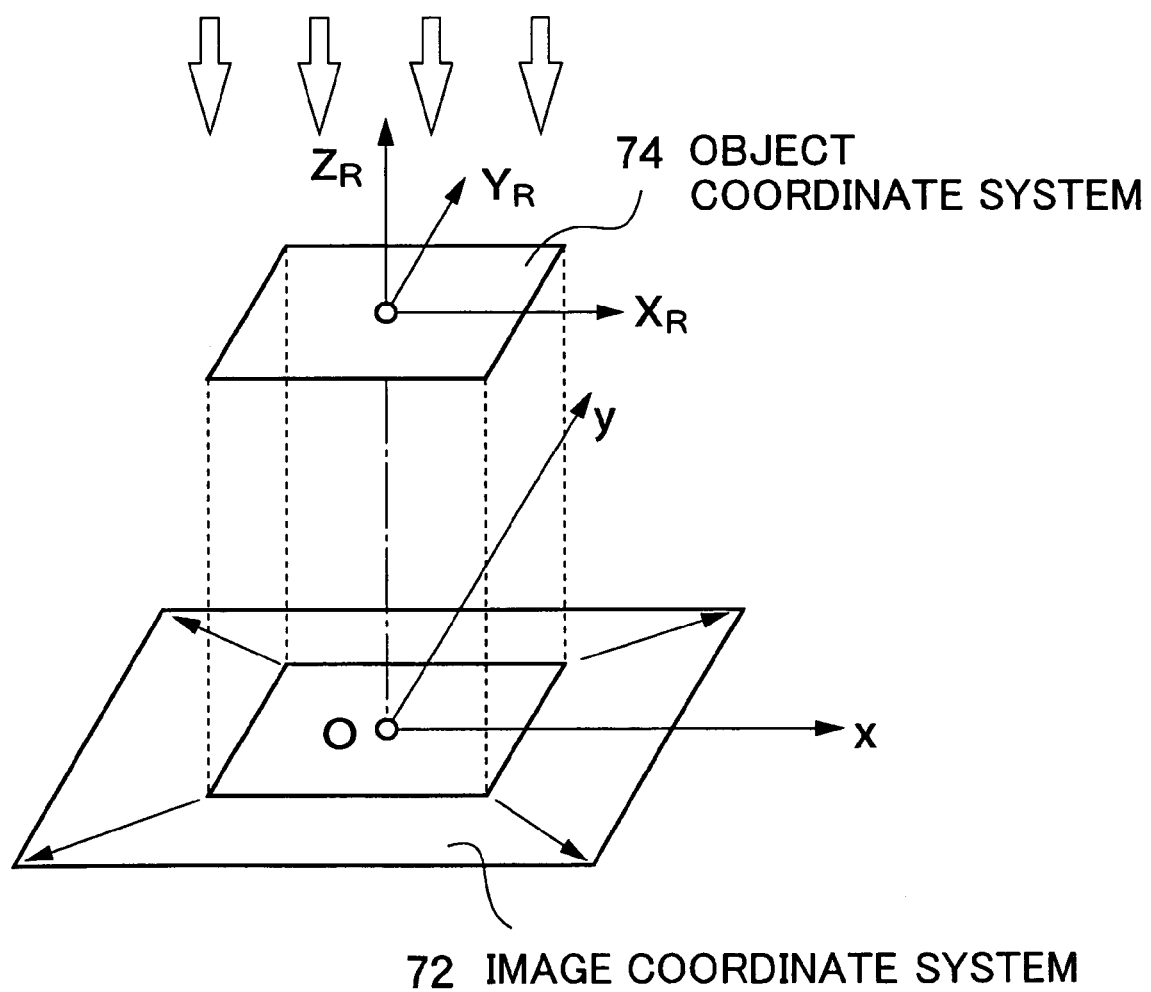
FIG. 5 is a diagram for illustrating parallel projection.

With reference to FIG. 5, a description is made of parallel projection, on which the calibration procedure for the electron beam device is premised. Electron microscopes have a wide range of magnification, ranging from low to high (for example, 2 to several million-power) magnification, and therefore the electron optical system 2 can be assumed to perform central projection with a low magnification and parallel projection with a high magnification. The magnification at which parallel projection is assumed to be performed may conveniently be determined using the calculation accuracy of deviation correction parameters as a reference. The reference magnification may be set, for example, at 1000-power or 10000-power. The deviation correction parameters are used to correct deviation between the right and left images of the sample so that a stereo image can be viewed stereoscopically.

FIG. 5 is a diagram for illustrating parallel projection. In cases of parallel projection, with a coordinate system $(X_R, Y_R, Z_R)$ in consideration of rotation used as an object coordinate system 74 and with K1 and K2 selected as scale factors, the following equation holds true:

$$\begin{bmatrix} x \\ y \\ 0 \end{bmatrix} = \begin{bmatrix} K_1 & 0 & 0 \\ 0 & K_2 & 0 \\ 0 & 0 & 0 \end{bmatrix} \begin{bmatrix} X_R \\ Y_R \\ Z_R \end{bmatrix} \quad (1)$$

Then, an origin $(X_O, Y_O, Z_O)$ selected from the object coordinate system 74 and an orientation matrix A can be used to represent the following equation:

$$\begin{bmatrix} X_R \\ Y_R \\ Z_R \end{bmatrix} = A \begin{bmatrix} X - X_0 \\ Y - Y_0 \\ Z - Z_0 \end{bmatrix} \quad (2)$$

Here, an element $a_{ij}$ of the orientation matrix A can be represented, with an element $a_{ij}$ of the rotation matrix using angles $\omega$, $\phi$, $\kappa$ of an image coordinate system 72 with respect to three axes X, Y, Z constituting the object coordinate system 74, as follows:

$$\begin{pmatrix} a_{11} = \cos\omega\cos\varphi, & a_{12} = -\cos\varphi, & a_{13} = \sin\omega \\ a_{21} = \cos\kappa\sin\varphi + \sin\kappa\sin\omega\cos\varphi, & a_{22} = \cos\kappa\cos\varphi - \sin\kappa\sin\omega\sin\varphi, & a_{23} = -\sin\kappa\cos\omega \\ a_{31} = \sin\kappa\sin\varphi - \cos\kappa\cos\omega\cos\varphi, & a_{32} = \sin\kappa\cos\varphi + \cos\kappa\sin\omega\sin\varphi, & a_{33} = \cos\kappa\cos\omega \end{pmatrix} \quad (3)$$

In order to calculate the deviation correction parameters, six exterior orientation elements $\omega$, $\Phi$, $\kappa$, $X_O$, $Y_O$, $Z_O$ included in the equations (1) and (2) must be found. That is, an observation equation is established using these equations on at least three reference marks, and the six exterior orientation elements are calculated with a successive approximation method. Concretely, in the successive approximation method, an approximation of an unknown variable is provided, Taylor-expansion is performed around the approximation for linearization, and a least squares method is used to find a correction quantity, to correct the approximation. The same operation is repeated to find a converged solution, to thereby obtain the six exterior orientation elements. In place of the equations (1) and (2), a choice can be appropriately made from a variety of operational equations used as exterior orientation in single photograph orientation, relative orientation, and other aerial triangulations, to perform operations.

Lens Distortion Correction

In order to find distortion aberration of the electron lenses constituting the electron optical system 2, a plurality of additional reference marks are prepared to obtain images from a plurality of directions, to allow correction using the equation (4). That is, when x, y coordinates after the lens distortion correction using the equations (1) and (2) are represented as x', y', then the following equation holds true:

$$x' = x + \Delta x$$

$$y' = y + \Delta y \quad (4)$$

Here, assuming k1, k2 as radial lens distortion factors, then the following equation can be used:

$$\Delta x = x_0 + x(k_1 r^2 + k_2 r^4) \quad (5)$$

$$\Delta y = y_0 + y(k_1 r^2 + k_2 r^4)$$

$$r^2 = (x^2 + y^2)/c^2$$

Distortion aberration of the electron lenses can be calculated by measuring image coordinates and object coordinates, substituting the measured coordinates into the equation above, and using the successive approximation method. Since the number of the lens distortion factors increase as unknown variables, distortion aberration of the electron lenses may conveniently be calculated by measuring image coordinates and object coordinates at increased reference points, substituting the coordinates into the equation, and using the successive approximation method. In the case of the equation (5), the lens distortion factors represent radial lens distortion. However, any element necessary for correction of tangential lens distortion, spiral lens distortion, or other distortion aberration of the electron lenses may be incorporated into the equation (5) to find respective lens distortion factors, to allow calibration of such lens distortions. For example, utilizing the found lens distortion factors, scanning of a beam can be performed in such a manner as to correct the lens distortions, to allow acquirement of a corrected image as a result. Alternatively, the lens distortions can be stored in a memory and scanning of a beam can be performed in such a manner as to correct the lens distortions, to allow lens distortion correction on an image.

Second Embodiment

Figure 6B:
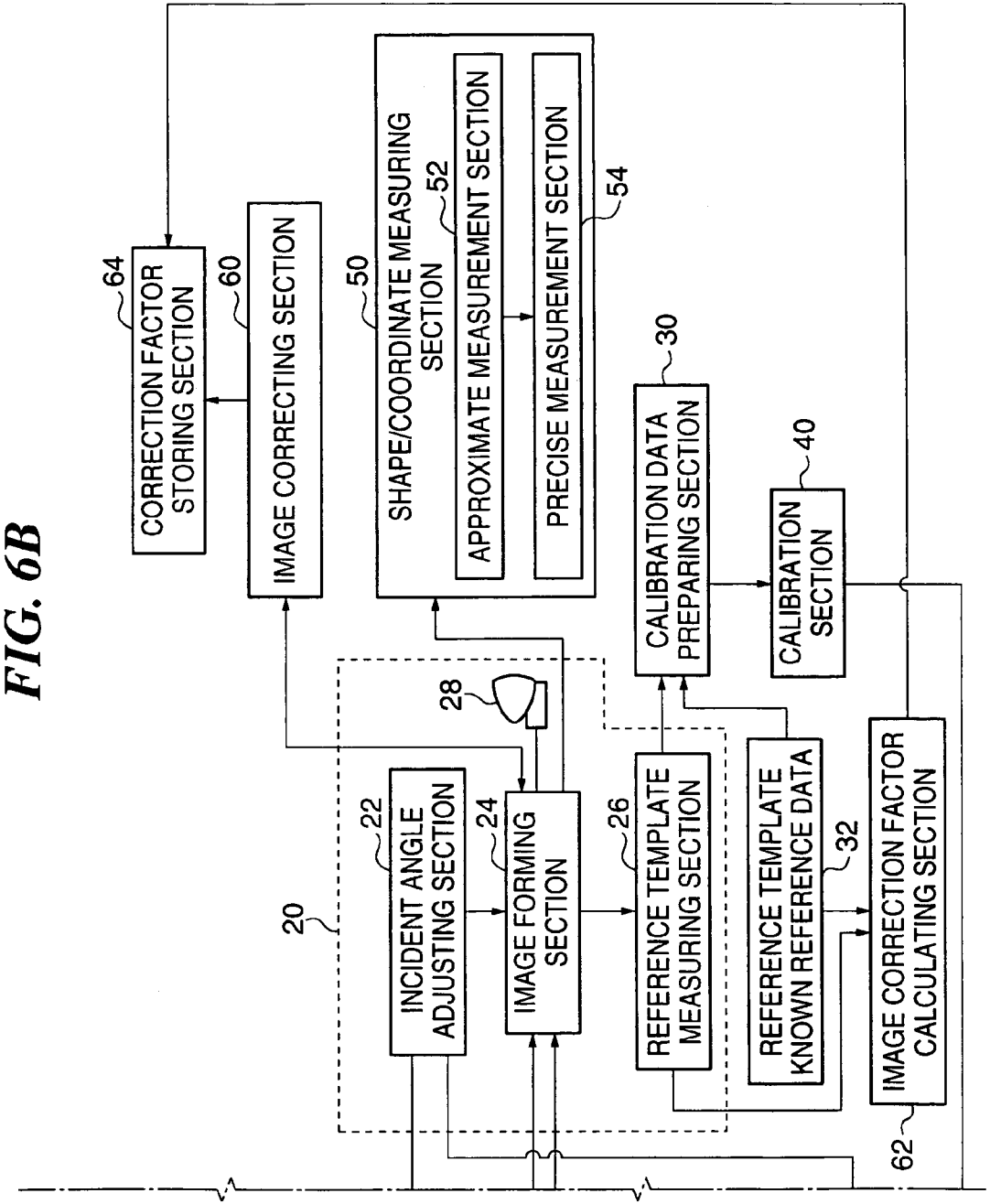

FIG. 6 is a block diagram illustrating the structure of a second embodiment of this invention. As shown in the figure, the electron beam measuring device includes an image correcting section 60, an image correction factor calculating section 62, and a correction factor storing section 64, in addition to the measuring section 20, the calibration data preparing section 30, the known reference data storing section 32, the calibration section 40, the electron lens aberration compensating section 42, and the shape/coordinate measuring section 50 described above.

The shape/coordinate measuring section 50 includes an approximate measurement section 52 and a precise measurement section 54. The approximate measurement section 52 finds the approximate shape or coordinate values of the sample 9 photographed in a stereo image. The precise measurement section 54 finds the shape or coordinate values of the sample 9 based on the stereo image corrected by the image correcting section 60.

The image correcting section 60 reads a correction factor corresponding to the tilt state in which the stereo image is photographed, from the correction factor storing section 64 based on the shape or coordinate values of the sample 9 found by the approximate measurement section 52, to correct the stereo image. The image correction factor calculating section 62 calculates correction factors for a stereo image, photographed by the electron beam detecting section 4, in a plurality of tilt states made by the sample tilting section 5. The calculation process for the correction factors will be detailed later. The correction factor storing section 64 stores the correction factors calculated with the image correction factor calculating section 62 in each of the plurality of tilt states made by the sample tilting section 5.

Figure 7A:
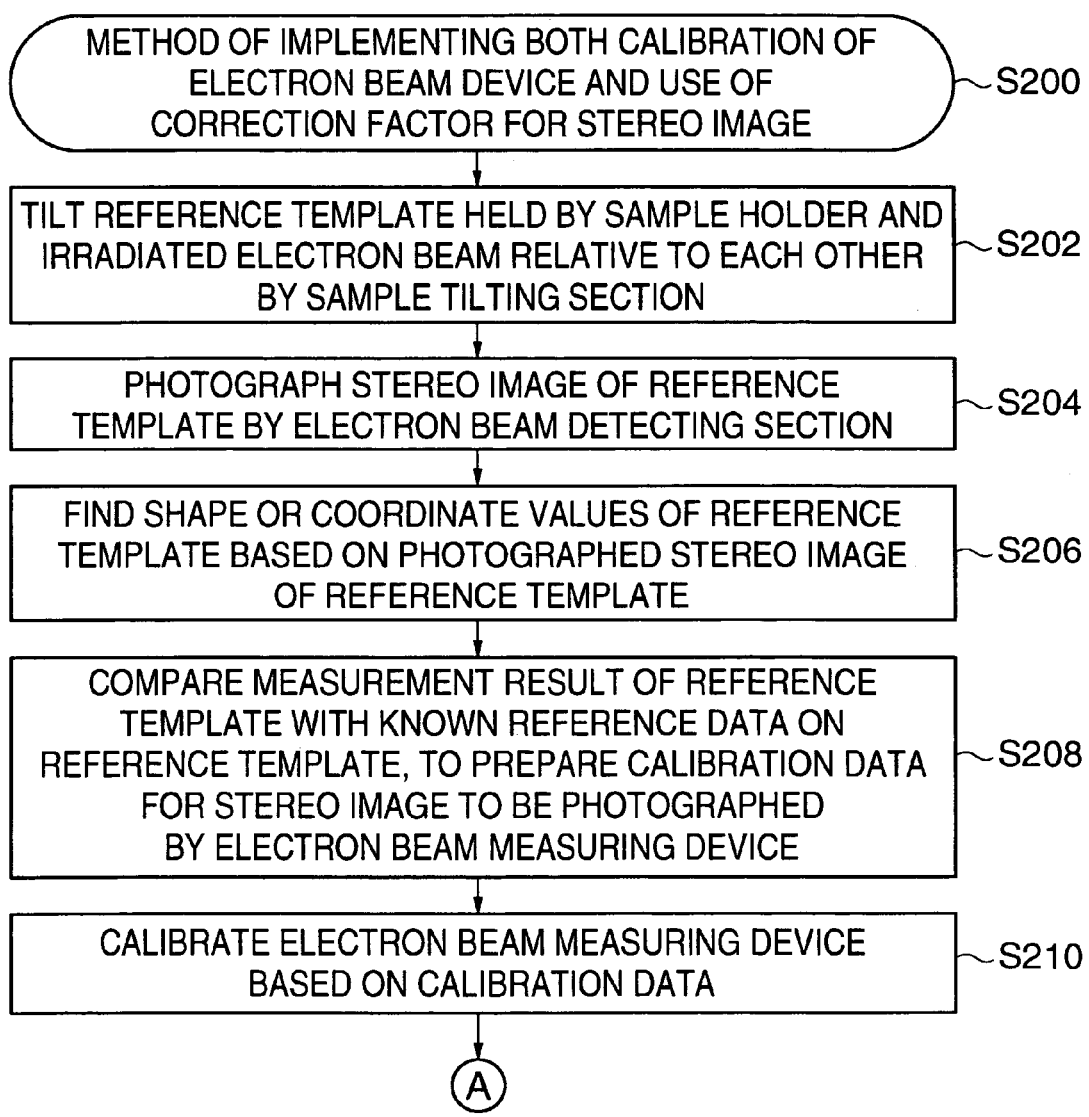
FIG. 7A and FIG. 7B are flowcharts of electron beam measurement including the calibration procedure for an electron beam device according to the second embodiment of this invention.
Figure 7B:
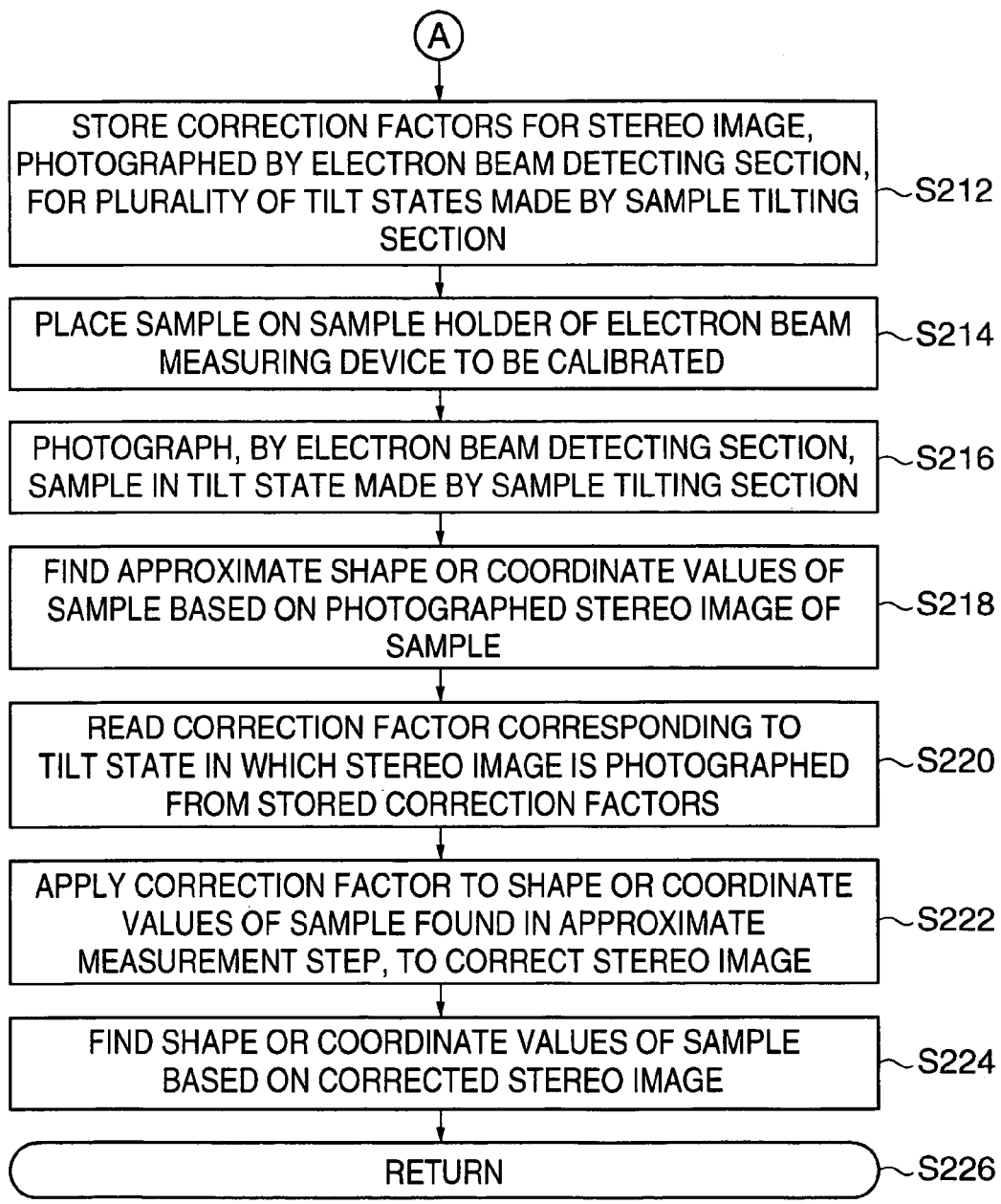

With reference to FIG. 7, a description is made of the calibration procedure for an electron beam device necessary for stereo image measurement by an device constituted as described above. FIG. 7 is a flowchart of electron beam measurement including the calibration procedure for the electron beam device according to the second embodiment of this invention. FIG. 7 shows a process flow of calibration of the electron beam device using the reference template 9a, 9c, and of subsequent measurement of an image of the sample (S200). The processes in S202 to S210 are the same as described above in S102 to S110. That is, a reference template 9a, 9c is placed on the sample holder 3, and the sample holder 3 or the electron beam 7 is brought into a tilt state (S202). The measuring section 20 acquires a tilted image of the reference template 9a, 9c from the electron beam detecting section 4 (S204). The measuring section 20 finds the shape or coordinate values of the reference template 9a, 9c based on the stereo image of the reference template 9a, 9c photographed by the electron beam detecting section 4 (S206). The calibration data preparing section 30 compares the measurement results of the reference template 9a, 9c in S206 with known reference data on the reference template 9a, 9c, to prepare calibration data for a stereo image photographed by the electron beam device 10 (S208). The calibration section 40 performs a calibration of the electron beam device 10 based on the calibration data so as to reduce aberration in an image of the sample detected by the electron beam detecting section 4 (S210). The image correction factor calculating section 62 calculates correction factors for a stereo image, photographed by the electron beam detecting section 4, in a plurality of tilt states made by the sample tilting section 5, to store the calculated correction factors in the correction factor storing section 64 (S212).

Then, a sample (measuring object) 9 is placed on the sample holder 3 (S214). The electron beam 7 or the sample holder 3 is brought into a desired tilt state, to allow the sample 9 to be photographed by the electron beam detecting section 4 (S216). As the desired tilt state, an angle at which much of the sample 9 can be viewed with minimum blind spots or an angle at which the targets particularly desired to be measured can be satisfactorily photographed may be selected, for example, when three-dimensional image measurement of the sample 9 is performed. The approximate measurement section 52 finds the shape or coordinate values of the sample 9 based on the stereo image of the sample 9 in the desired tilt state (S218).

The image correcting section 60 reads a correction factor corresponding to the tilt state in which the stereo image is photographed, from the correction factor storing section 64 (S220). The image correcting section 60 applies the correction factor read in S220 to the shape or coordinate values of the sample 9 found by the approximate measurement section 52, to correct the stereo image (S222). The precise measurement section 54 finds the shape or coordinate values of the sample 9 based on the stereo image corrected by the image correcting section 60 (S224). The process is returned when the precise shape or coordinate values of the sample 9 can be acquired (S226). Preferably, in order to allow an observation of the sample, the stereo image corrected by the image correcting section 60 may be displayed on the display device 28.

Figure 8:
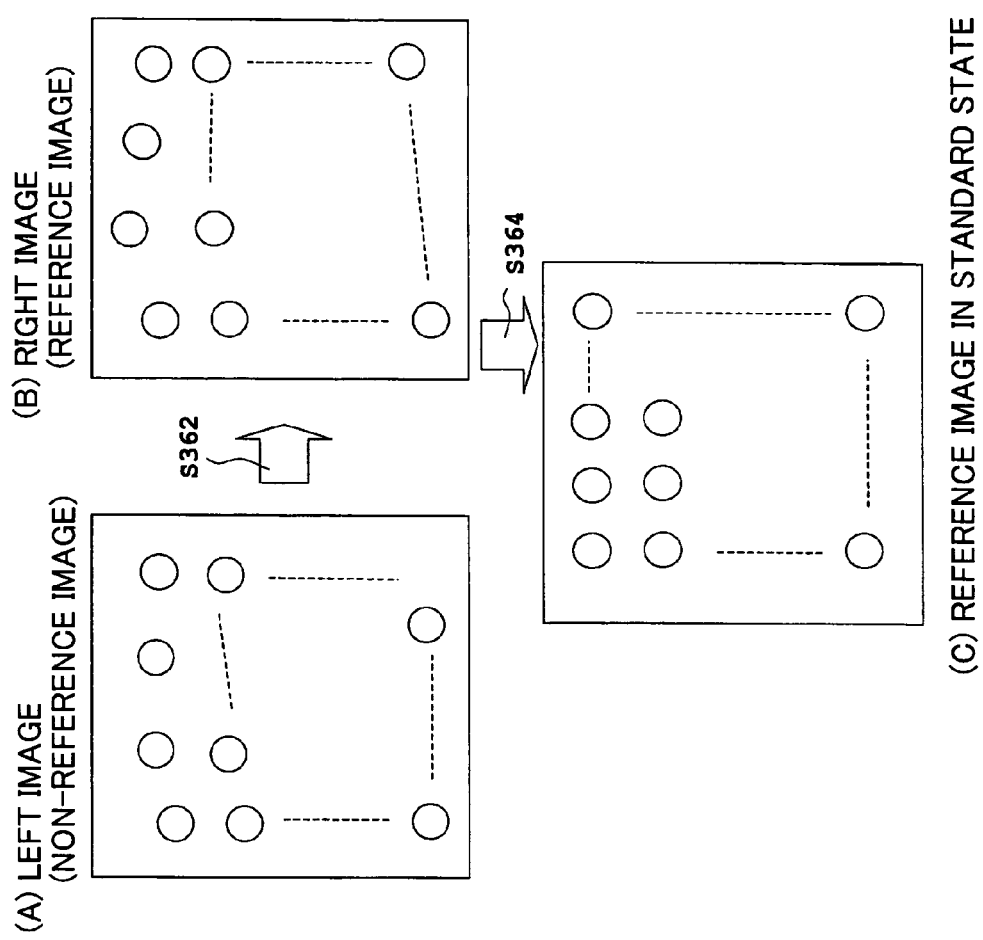
FIG. 8 is a diagram illustrating right and left images constituting a stereo image photographed by an electron beam detecting section 4, and an image in a standard state.

With reference to FIG. 8, a description is made of an example of the process performed in S106 and S116 of FIG. 4, and S206 and S218 of FIG. 7. In this process, the shape or coordinate values of the reference template 9a, 9c or the sample 9 are found based on the stereo image of the reference template 9a, 9c or the sample 9 in a desired tilt state. FIG. 8 is a diagram illustrating right and left images constituting a stereo image photographed by the electron beam detecting section 4, and an image in a standard state. In the figure, (A) shows a non-reference image, (B) shows a reference image and the non-reference image subject to an image converting process, and (C) shows an image in the standard state subject to an image coordinate transforming process. A non-reference image is subject to the image converting process using a first image correction factor into a reference image in a tilt state. The image of (B) in FIG. 8 is further subject to the image coordinate transforming process. The image coordinate transforming process is intended to transform, by way of coordinates, the reference image and the non-reference image converted by way of coordinates into images in a state where the relative tilt angle by the sample tilting section 5 is in the standard state, and may be performed by, for example, the measuring section 20 or the shape/coordinate measuring section 50. Since image distortion is not particularly corrected in the coordinate transformation, the image processing in the coordinate transformation is simpler than that in the image conversion. Also, since an image is transformed by way of coordinates into an image in the standard state, an image of the sample photographed in a tilt state can be utilized easily.

Figure 9:
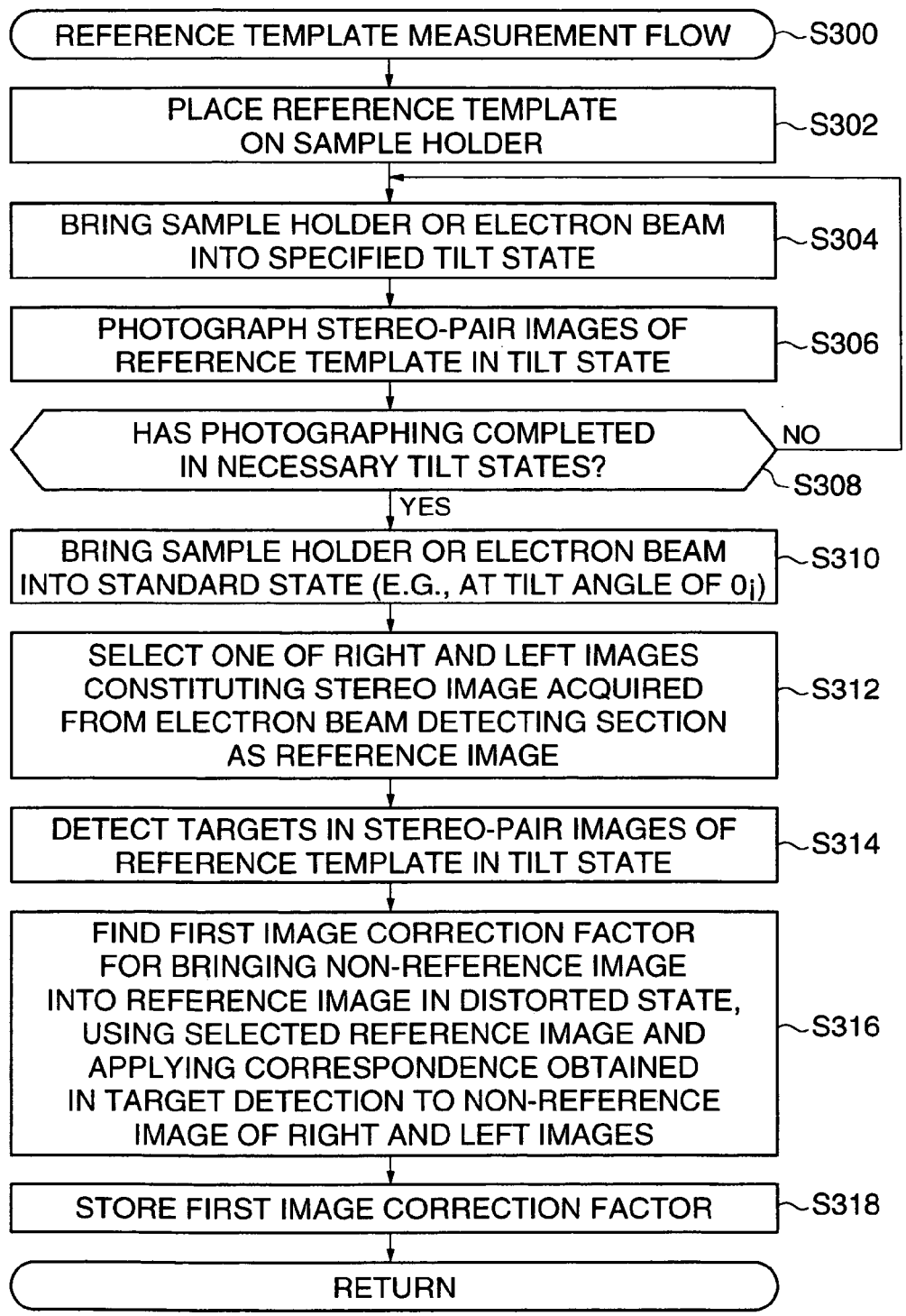
FIG. 9 is a flowchart of an example of a process for finding a shape or coordinate values of a reference template.

FIG. 9 is a flowchart of an example of a process for finding the shape or coordinate values of the reference template. FIG. 9 shows a flow of measurement of a correction factor for an image converting process using the reference template 9a, 9c performed by the measuring section 20 (S300). A reference template 9a, 9c is placed on the sample holder 3 (S302). The sample holder 3 or the electron beam 7 is brought into a tilt state (S304). The electron beam measuring device acquires a tilted image of the reference template from the electron beam detecting section 4 (S306). The electron beam measuring device determines whether or not the necessary number of images for a tilted image acquiring process have been acquired (S308). If the necessary number of images have not been acquired yet in S308, the process returns to S304, to acquire another tilted image.

If the necessary number of images have been acquired in S308, the measuring section 20 acquires an image of the reference template in a standard tilt state, such as an image in a horizontal state (at a tilt angle 0°) (S310). In cases where the design values or measurement values of the reference template 9a, 9c are known, the design values or known measurement values may be used instead of or in addition to the image measurement. In cases where the beam system is adjusted to a tilt angle 0°, an image of the reference template at a tilt angle of 0° may be used as the image in the standard tilt state.

Then, the measuring section 20 performs a variable/coefficient acquiring process (S312 to S318). The measuring section 20 selects one of the stereo-pair tilted images, that is, one of the right and left images constituting a stereo image obtained from the electron beam detecting section 4, as a reference image (S312). A target detection is performed for the stereo-pair tilted images (S314). In cases where an image at a tilt angle 0° has been acquired as the reference image, the target detection is also performed for the reference image. In this case, since the approximate positional relations among the characteristic points are known, erroneous correspondence can be avoided. Thus, image measurement can be carried out simply by designating (automatic recognition) several characteristic points as the targets, even when there is a point similar to the target in the image, according to a series of processes (i) to (v) as follows.

<i>: Reading the approximate positions of a pattern, in cases where the sample is a semiconductor chip. In such cases, if the design values or the intervals in the pattern of the semiconductor chip are identified, such identified values may be used. These are set as reference point coordinates.

<ii>: Designating at least three corresponding points each on the reference image and the search image. These are set as image coordinates.

<iii>: Calculating parameters for the reference image and the search image using the following equations. That is, the reference point coordinates corresponding to the image coordinates are substituted into the quadratic projective transformation (6) to establish an observation equation, to find parameters b1 to b8.

$$X=(b1 \cdot x+b2 \cdot y+b3)/(b7 \cdot x+b8 \cdot y+1) \quad (6)$$

$$Y=(b4 \cdot x+b5 \cdot y+b6)/(b7 \cdot x+b8 \cdot y+1)$$

where X, Y represent image coordinates, and x, y represent reference point coordinates.

<iv>: Finding the positions of all the pattern on the reference image and the search image by calculation using the found parameters b1 to b8.

<v>: Performing a measurement on the areas around the found positions corresponding to the pattern by a stereo matching process.

Stereo Matching Process

Figure 10:
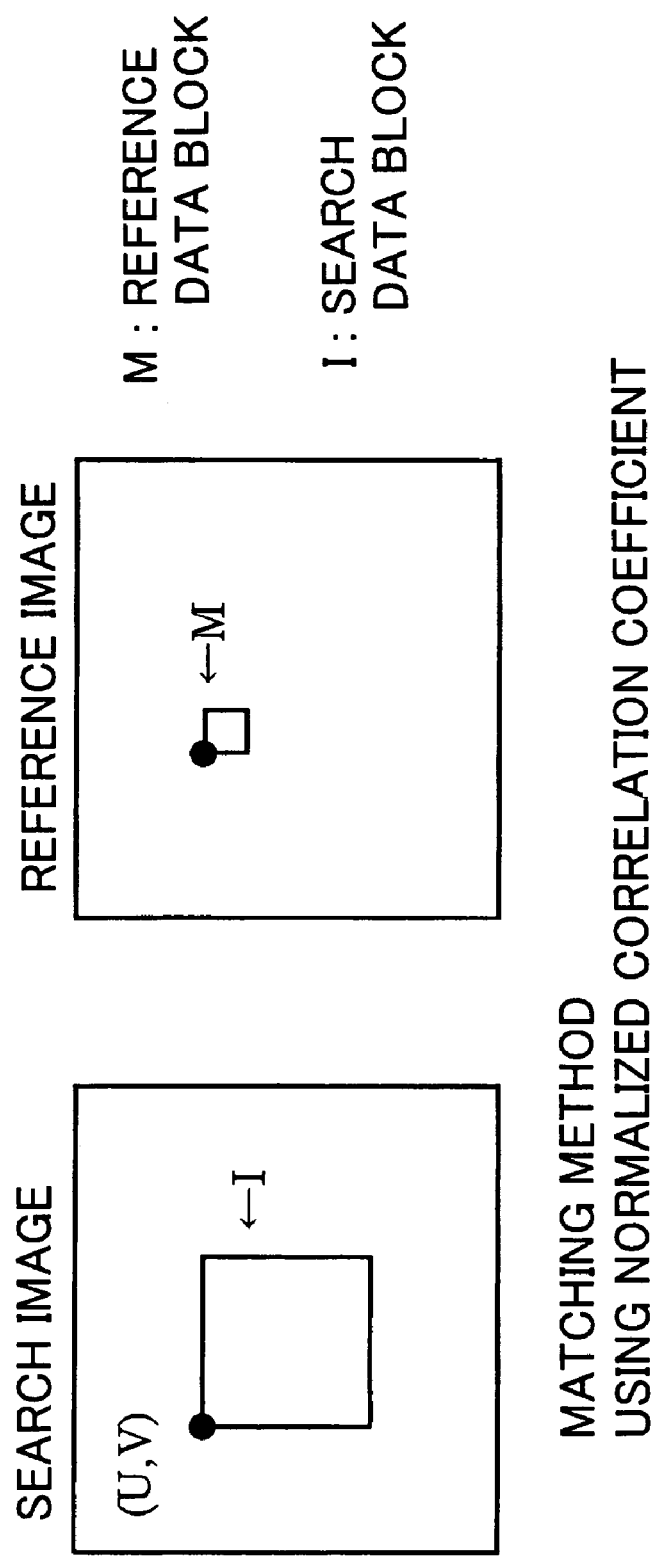
FIG. 10 is a diagram for illustrating a matching method using a normalized correlation coefficient.

With reference to FIG. 10, a description is made of an area-based matching method using a normalized correlation coefficient as an example of the stereo matching process. FIG. 10 is a diagram for illustrating a matching method using a normalized correlation coefficient. In the figure, the right and left images are a reference image and a search image, respectively. Here, a reference data block in the reference image constituted of N pieces of data is denoted as M, and a search data block in the search image with a coordinate (U, V) as a starting point is denoted as I.

The matching method using a normalized correlation coefficient is intended to find the degree of similarity between the reference data block M and the search data block I at each position using the correlation coefficient while performing a raster scanning of the reference data block M in the search data block I In the raster scanning, the reference data block M is moved in the search data block I from left to right, and when reaching the right end of the search data block I, the reference data block M is returned to the left end of the row below and again moved from left to right. By finding the position where the value of a correlation coefficient R is largest, the same position in the search data block I as the reference data block M can be found.

$$M=M(Xi, Yi) 1 \le i \le N \quad (7)$$

$$I=I(U+Xi, V+Yi) \quad (8)$$

When the equations above hold true, the normalized correlation coefficient R (U, V) can be obtained by the following equation:

$$R(U, V)=(N\Sigma Ii Mi-\Sigma Ii \Sigma Mi)/SQRT[\{N\Sigma Ii^2-(\Sigma Ii)^2\} \times \{N\Sigma Mi^2-(\Sigma Mi)^2\}] \quad (9)$$

The correlation coefficient R must take a value from −1 to +1. When the correlation coefficient R is +1, the template and the search image completely coincide with each other.

Then, the image correction factor calculating section 62 finds a first image correction factor for bringing the non-reference image into the reference image in a distorted state, using the reference image selected in S312 and applying the correspondence between the stereo-pair images to the non-reference image of the tilted stereo-pair images (S316). The first image correction factor found in S316 is stored, for example, in the correction factor storing section 64 so as to be available, for example, to the measuring section 20, the shape/coordinate measuring section 50, and the image correcting section 60 (S318). The first image correction factor is used to convert an image while correcting image distortion, by a variety of operational processes such as making a model using points detected with a calibration method using parallel projection, a curved-line approximation method using a least squares method, a method of making an approximation using an affine transformation, and of finding a factor used to make the approximation, or the like.

Affine Transformation Equation

Here, affine transformation is described as an example of the image converting process.

$$x' = b1 \cdot x + b2 \cdot y + b3 \quad (10)$$

$$y' = b4 \cdot x + b5 \cdot y + b6$$

Coefficients b1 to b6 can be calculated by measuring at least four corresponding points on the right and left images and using the successive approximation method. Thus, the coefficients can be calculated by associating the stereo-pair right and left images using the coordinate values obtained by the target detection. Then, conversion coefficients are calculated in the same manner from the detected positions in the reference image selected in S312 and the target positions in, or the reference values (design values) of, the image acquired at a tilt angle 0°.

Figure 11:
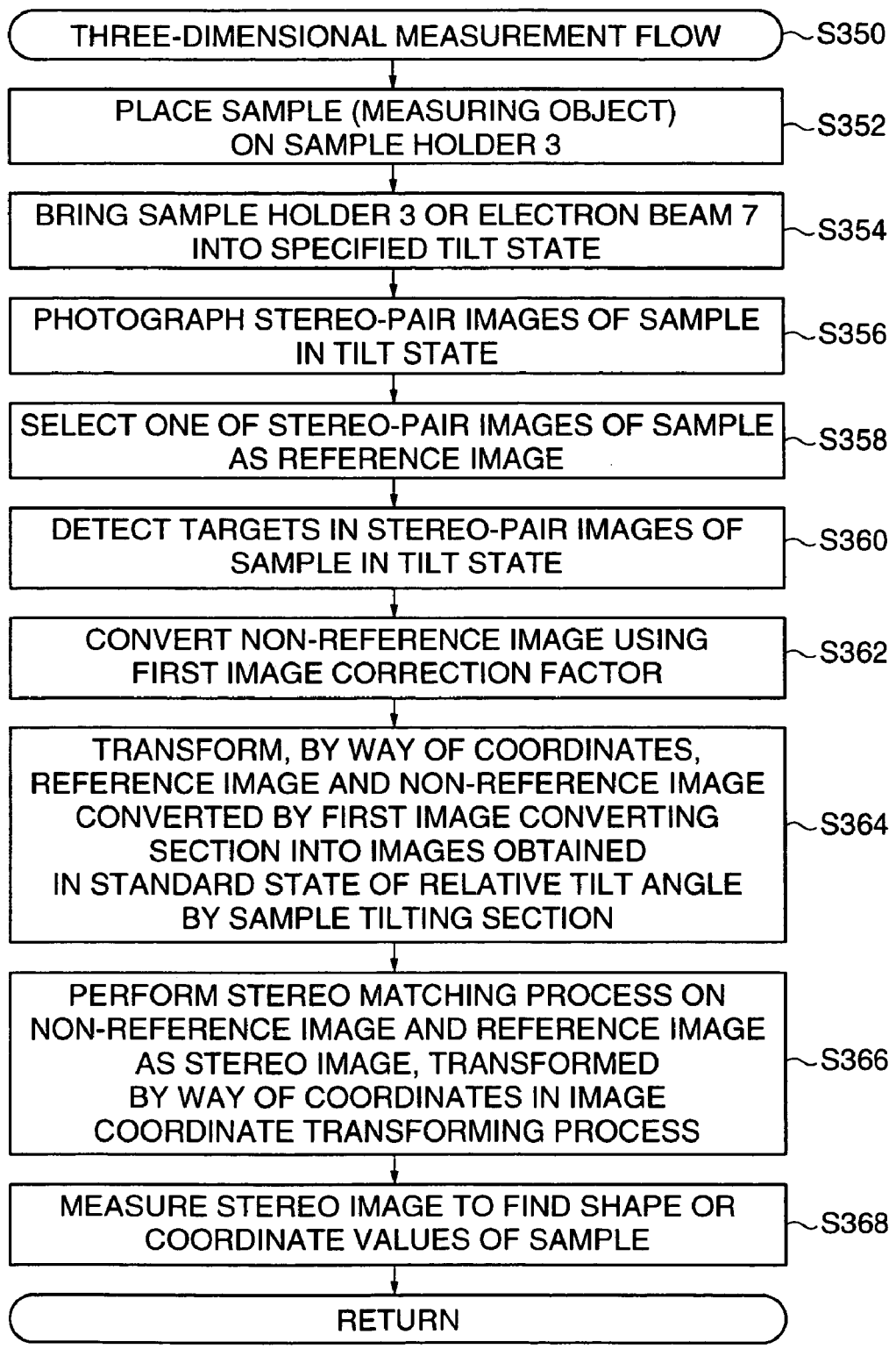
FIG. 11 is a flowchart illustrating an example of a process for finding a shape or coordinate values of a sample.

FIG. 11 is a flowchart illustrating an example of a process for finding the shape or coordinate values of the sample. FIG. 11 shows a flow of three-dimensional measurement of the sample 9 using the first image correction factor found in S316 of FIG. 9 (S350). A measuring object 9 is placed on the sample holder 3 (S352). The electron beam 7 or the sample holder 3 is brought into a desired tilt state (S354). As the desired tilt state, an angle at which much of the sample 9 can be viewed with minimum blind spots or an angle at which the targets particularly desired to be measured can be satisfactorily photographed may be selected, for example, when three-dimensional image measurement of the sample 9 is performed. Stereo-pair images of the sample 9 in the desired tilt state are acquired (S356). Then, the measuring section 20 performs a reference image selecting process. One of the stereo-pair tilted images, that is, one of the right and left images constituting a stereo image obtained from the electron beam detecting section 4 is selected as a reference image (S358). A target detection is performed for the stereo-pair tilted images (S360).

The measuring section 20 performs the image converting process. The non-reference image of the stereo-pair right and left images is converted using the first image correction factor (S362). Then, the measuring section 20 performs the image coordinate transforming process. The reference image and the non-reference image converted through the image converting process by the measuring section 20 are transformed by way of coordinates into an image in a state where the relative tilt angle by the sample tilting section 5 is in the standard state (S364). The shape/coordinate measuring section 50 performs the stereo matching process on the non-reference image and the reference image transformed by way of coordinates through the image coordinate transforming process by the measuring section 20 as a stereo image (S366).

The shape/coordinate measuring section 50 performs a stereo image measurement and calculates the three-dimensional coordinates of the photographed sample 9, to find the shape or coordinate values of the sample (S368). In the embodiment above, the stereo matching process is performed after the image converting process and the image coordinate transforming process by the measuring section 20. However, this invention is not limited thereto. The stereo matching process may alternatively be performed after the image converting process by the measuring section 20 and before the image coordinate transforming process by the measuring section 20.

An additional step may be inserted between S364 and S366, of converting the reference image and the non-reference image transformed by way of coordinates through the image coordinate transforming process by the measuring section 20, using a second image correction factor for removing image distortion in the reference image with respect to the image in a state where the relative tilt angle by the sample tilting section 5 is in the standard state. There may be cases where image distortion involved in the electron beam device 10 is different between an image photographed in a tilt state suitable to photograph the sample and an image photographed in a state where the relative tilt angle by the sample tilting section 5 is in the standard state. In such cases, the non-reference image and the reference image transformed by way of coordinates through the image coordinate transforming process by the measuring section 20 can be corrected using the second image correction factor, to thereby allow the shape/coordinate measuring section to find the accurate shape or coordinate values of the sample.

Height Measurement

Figure 12:
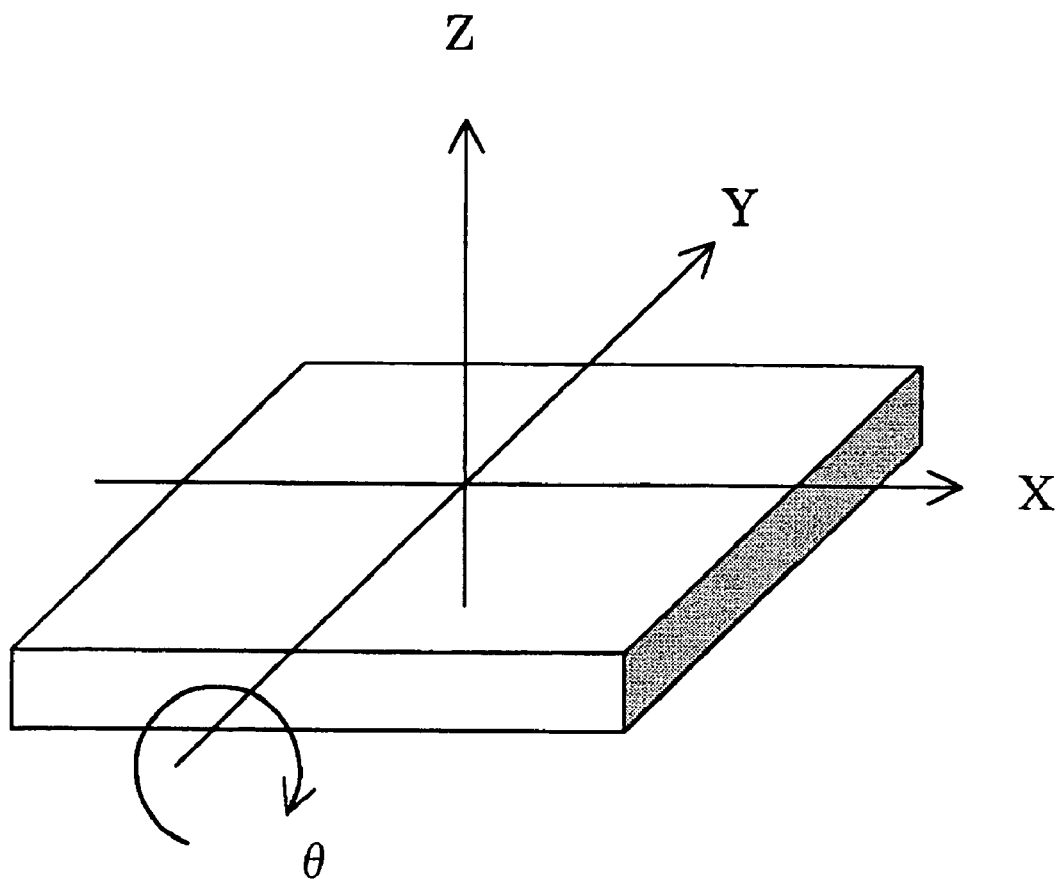
FIG. 12 is a perspective view illustrating the coordinate system of the sample holder 3.

Here, a description is made of the basic principle of height measurement. Also, a description is made of a case where a parameter for correcting the lens distortion in the height direction of the measuring object 9 is included in the first image correction factor. FIG. 12 is a perspective view illustrating the coordinate system of the sample holder 3. The height of the sample 9 placed on the sample holder 3 can be corrected at the respective tilt angles $\Phi$ as shown in FIG. 2B. Thus, a space correction may be performed at the angles and height distortion correction factors at the respective angles may be included in the first image correction factor and stored. Photographing the measuring object 9 as tilted at an angle ($\Phi$ is equivalent to photographing the measuring object 9 with the electron beam 7 tilted at an angle $\Phi$ applied by means of a tilt mechanism for an electron beam or observation optical axis. In the coordinate system of the sample holder 3, the axis of rotation is the Y-axis and the angle $\theta$ is defined with the clockwise direction being the positive direction.

Figure 13:
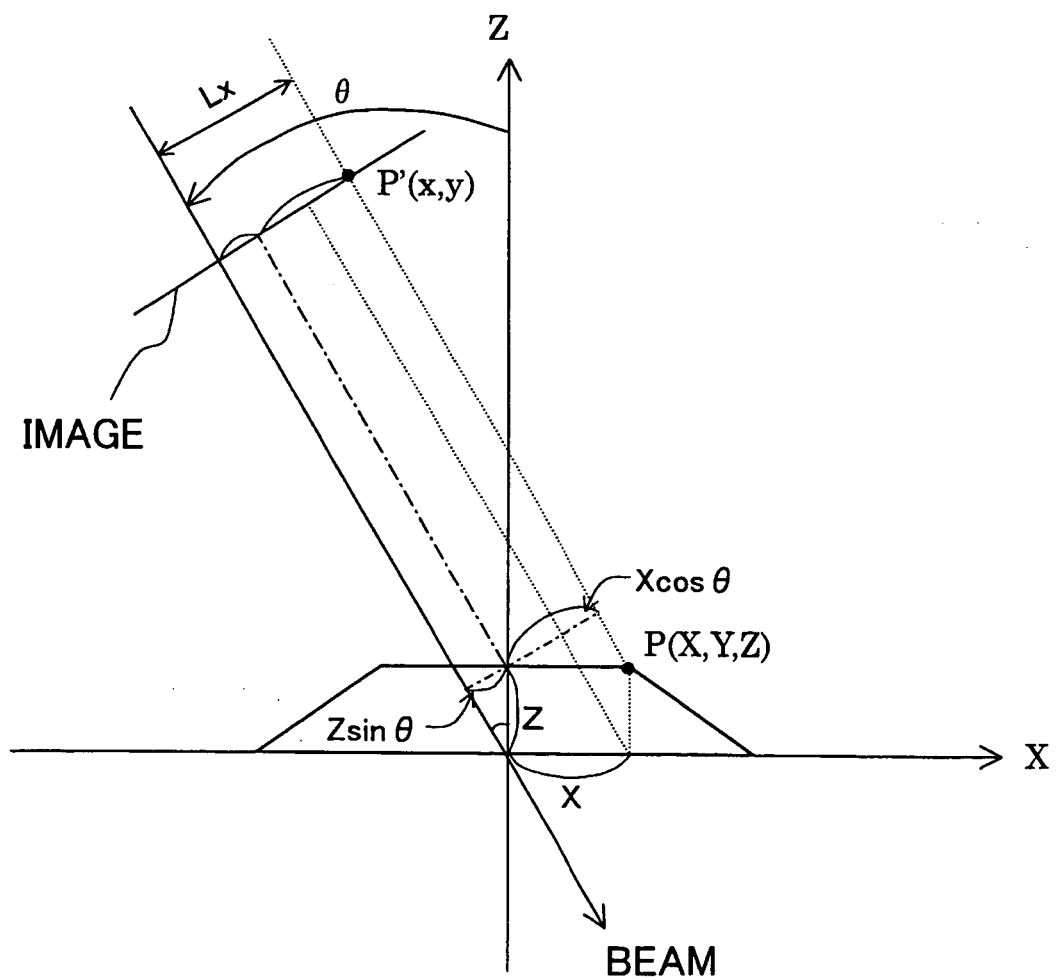
FIG. 13 is a front view showing the relation between an image and the sample when an electron beam is irradiated on the measuring object 9.

FIG. 13 is a front view showing the relation between an image and the sample when an electron beam is irradiated on the measuring object 9. From a geometric relation:

$$\text{Left image: } Lx = (X \times \cos\theta + Z \times \sin\theta) \times s \quad (11)$$

$$Ly = Y \quad (11)$$

$$\text{Right image: } Rx = (X \times \cos\theta - Z \times \sin\theta) \times s \quad (12)$$

$$Ry = Y$$

where s: resolution (1 pixel).

The three-dimensional coordinates can be found by using the orientation matrix in consideration of the rotational angle of the image and the sample, as follows:

$$X = Lx + Rx \quad (13)$$

$$Z = Lx - Rx$$

$$Y = Ly = Ry$$

Figure 14:
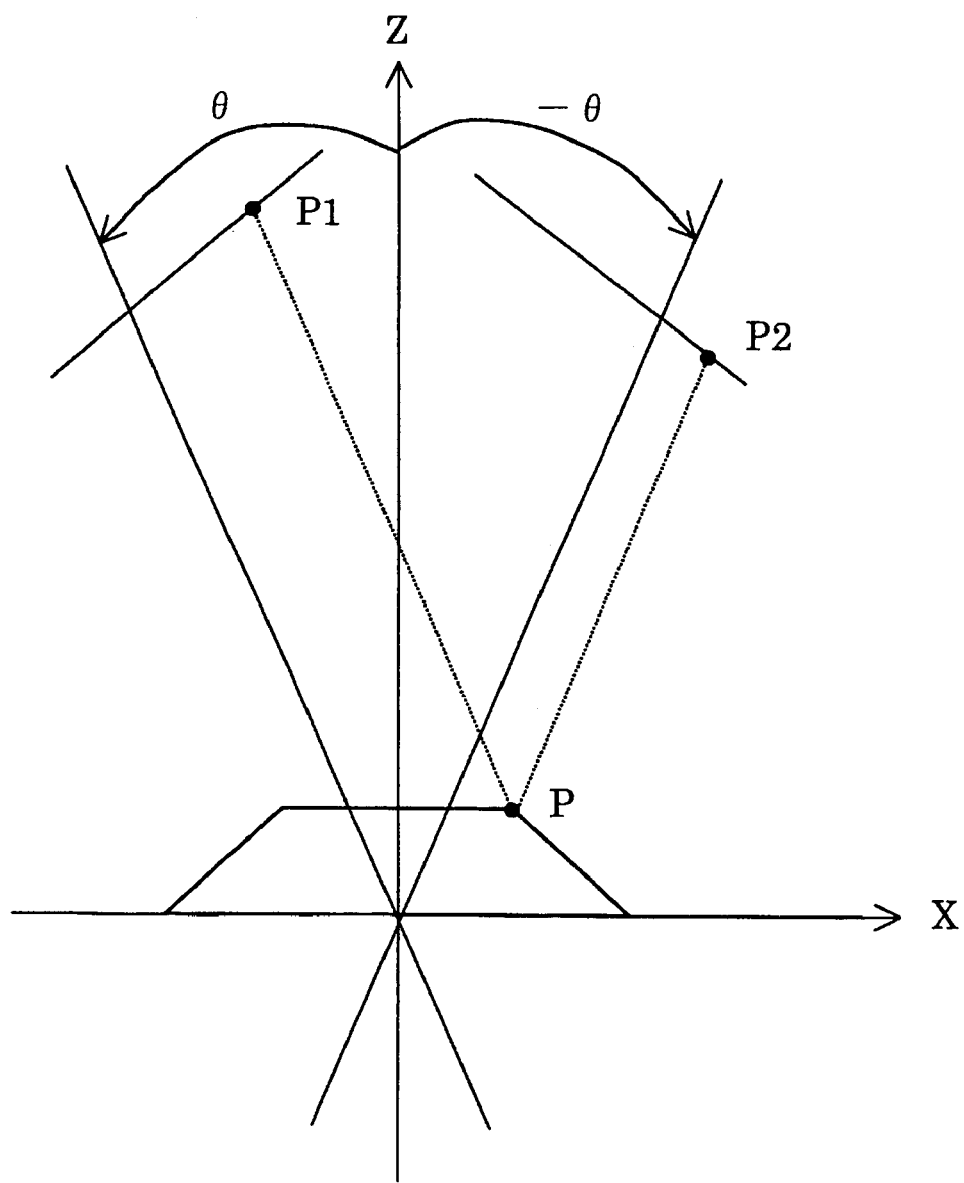
FIG. 14 shows a case where the photographing angles of right and left images constituting a stereo image are opposite with respect to the Z-axis.

The equation (13) is effective only where the photographing angles of the right and left images constituting a stereo image are opposite with respect to the Z-axis as shown in FIG. 14.

Figure 15:
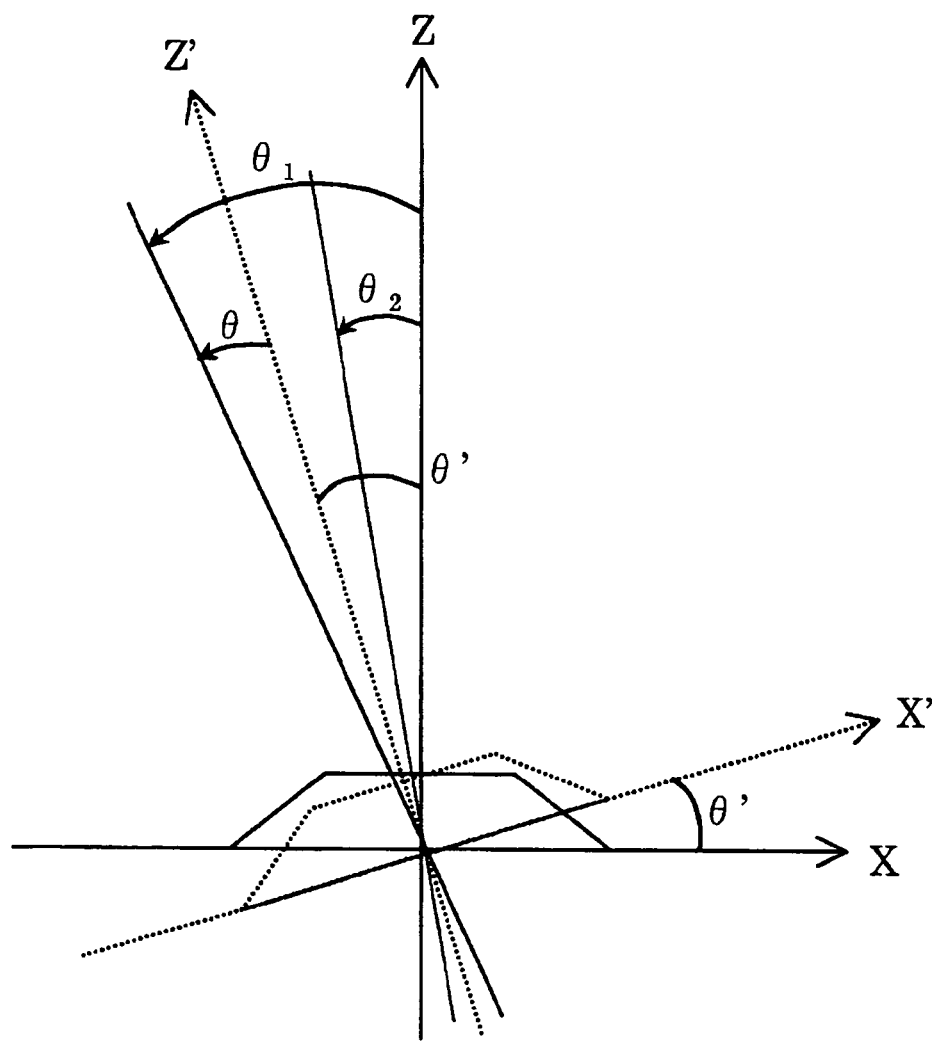
FIG. 15 shows a case where the photographing angles of right and left images constituting a stereo image are respectively tilted at angles θ1 and θ2 with respect to the Z-axis.

With reference to FIG. 15, an angle-independent equation is derived. FIG. 15 shows a case where the photographing angles of the right and left images constituting a stereo image are respectively tilted at angles θ1 and θ2 with respect to the Z-axis.

The left image is photographed at an angle θ1 and the right image is photographed as an angle θ2, and a Z'-axis titled at an angle θ' with respect to the Z-axis is assumed. Assume that the photographing angles of the right and left images in FIG. 14 are symmetric with respect to the Z'-axis. By applying a pseudo-coordinate (X', Y', Z'), the angles of the images can be represented as θ'±θ. Then, by using the equation (12), the pseudo-coordinate (X', Y', Z') is rotated by an angle θ' to be represented in a coordinate system X, Y, Z.

$$Z' = ((Lx - Rx)/(2 \times \sin \theta)) \times s \quad (14)$$

$$X' = ((Lx + Rx)/(2 \times \cos \theta)) \times s$$

$$Y = Ly = Ry$$

Thus, the following equations hold true:

$$X = X' \times \cos \theta' - Z' \times \sin \theta' \quad (15)$$

$$Z = X' \times \sin \theta' + Z' \times \cos \theta'$$

$$Y = Y'$$

Thus, lens distortion in the height direction of the measuring object 9 in the stereo pair tilted images can be corrected by applying the equation (13) or (15), depending on the tilt state of the sample 9. That is, the electron beam measuring device can generate lens-distortion-corrected stereo-pair images of the measuring object 9, using the approximate position and height of the measuring object 9 and height correction parameters included in the first image correction factor. The generated stereo-pair images of the measuring object 9 can be displayed on a display device, such as a CRT, of the electron beam measuring device.

In the second embodiment, one of stereo-pair right and left images is selected as a reference image, and another, non-reference image is converted by way of image coordinates toward the reference image. After a stereo matching process is performed on the images, they are transformed to be represented in standard coordinates, and three-dimensional coordinates of the sample 9 are calculated (see FIG. 8). When the non-reference image is converted by way of image coordinates toward the reference image, advantageously the occurrence rate of miss matching in the stereo matching process can be reduced and the reliability of the stereo matching can be increased, by correcting the distortions in the right and left images.

Third Embodiment

Figure 16A:
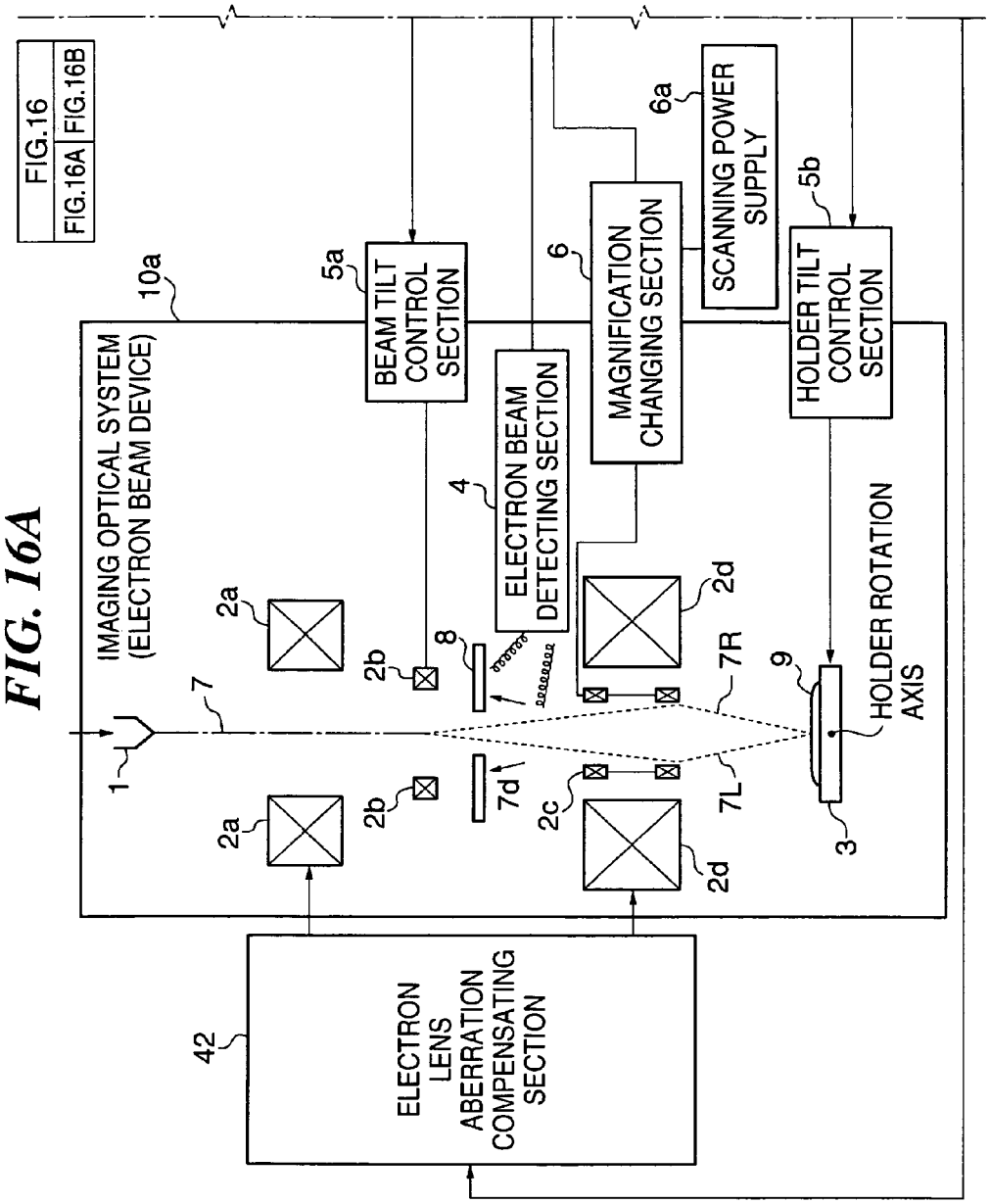
FIG. 16A and FIG. 16B are general block diagrams illustrating the structure of a third embodiment of this invention.
Figure 16B:
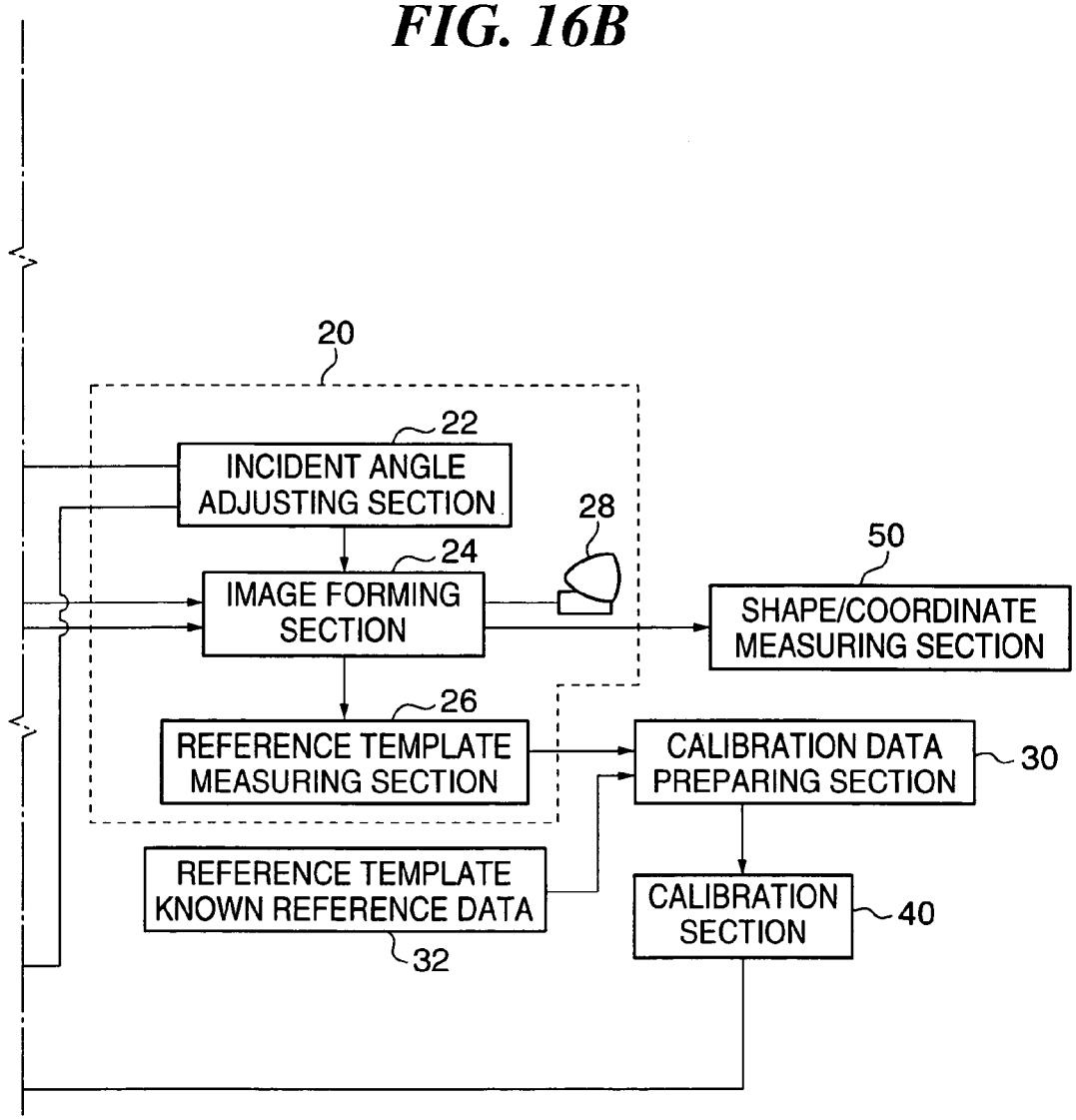

FIG. 16 is a general block diagram illustrating the structure of a third embodiment of this invention. In the third embodiment, the electron beam of the scanning electron microscope 10*a* is deflected to obtain a stereo image, unlike the first and second embodiments, where the holder is tilted to obtain a stereo image. In FIG. 16, components corresponding to those in FIG. 1 are given the same reference numerals and symbols, and descriptions of them are not repeated. A beam tilt control section 5*a* for controlling the tilt of the electron beam 7 is provided as the tilt control section 5. The beam tilt control section 5*a* transmits a tilt control signal to the deflection lenses 2*b* so that the irradiated electron beam 7 is switched between an electron beam 7R which makes a first tilt angle relative to the sample holder 3 and an electron beam 7L which makes a second tilt angle relative to the sample holder 3. The beam tilt control section 5*a* may be able to adjust the relative tilt angle between the irradiated electron beam 7 and the sample holder 3, not limiting to two angles, but to a multiplicity of angles. At least two angles are necessary to obtain stereo detection data.

Fourth Embodiment

Figure 17B:
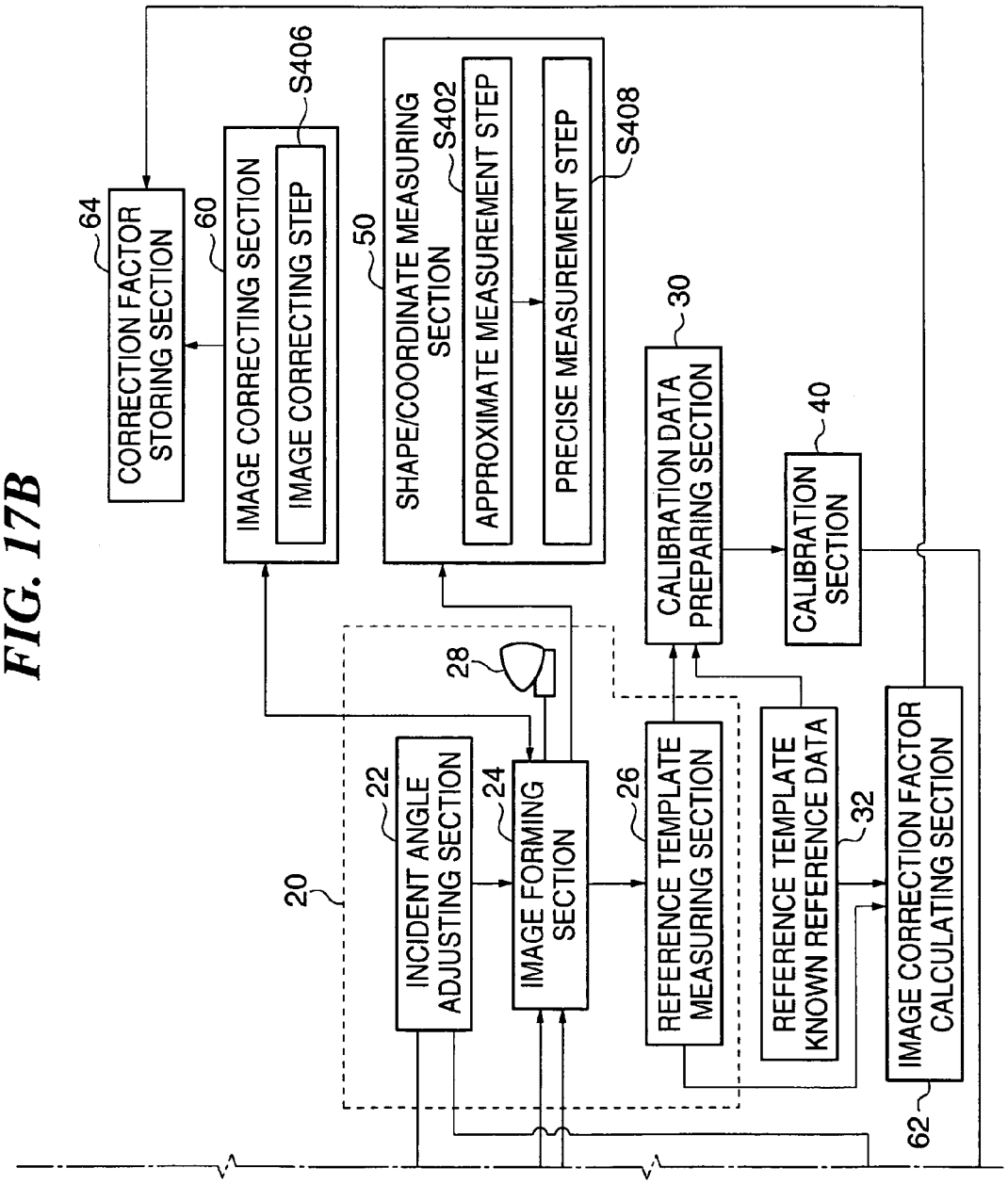

FIG. 17 is a general block diagram illustrating the structure of a fourth embodiment of this invention. As shown in the figure, the electron beam measuring device includes a shape/coordinate measuring section 50 as a third measuring section, an image correcting section 60, an image correction factor calculating section 62, and a correction factor storing section 64, in addition to the measuring section 20 described in relation to the first embodiment. The shape/coordinate measuring section 50 has the function of performing an approximate measurement step S402 and a precise measurement step S408. The image correcting section 60 has the function of performing image correcting steps (S404 and S406). The electron beam devices according to the first to third embodiments require the calibration procedure and are therefore provided with a calibration data preparing section 30, a known reference data storing section 32, a calibration section 40, and an electron lens aberration compensating section 42. In the fourth embodiment, on the other hand, the electron beam device is assumed to have finished with the calibration procedure and only performs an image correction.

Figure 18:
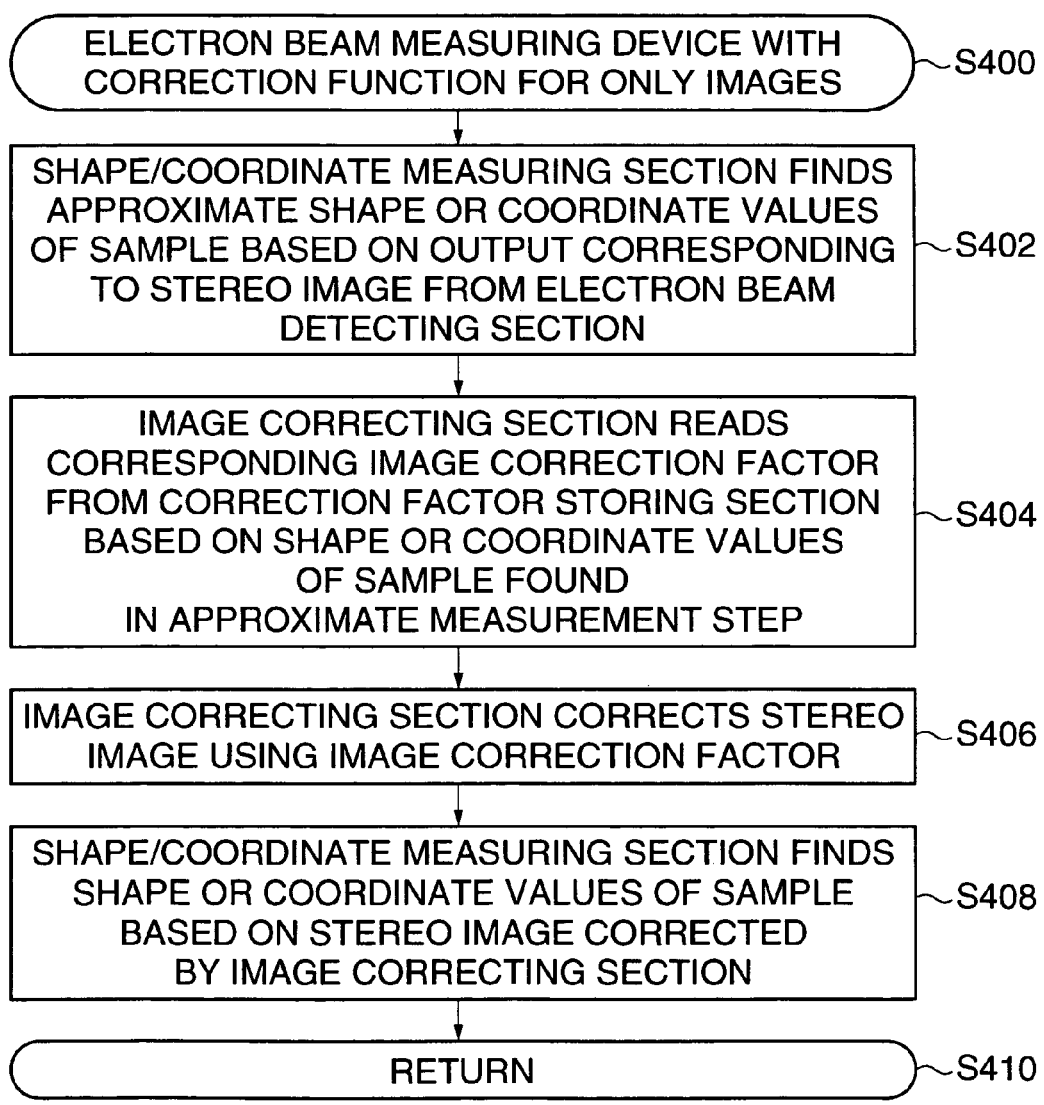
FIG. 18 is a flowchart of electron beam measurement according to the fourth embodiment of this invention.

A description is made of the operation of an device constituted as described above. FIG. 18 is a flowchart of electron beam measurement according to the fourth embodiment of this invention. In the approximate measurement step, the shape/coordinate measuring section 50 finds the approximate shape or coordinate values of the sample 9 based on an output corresponding to a stereo image detected by the electron beam detecting section 4 (S402). In the image correcting steps, the image correcting section 60 reads a corresponding image correction factor from the correction factor storing section 64 based on the shape or coordinate values of the sample 9 found in the approximate measurement step (S404), and uses the image correction factor to correct the stereo image (S406). In the precise measurement step, the shape/coordinate measuring section 50 finds the shape or coordinate values of the sample 9 based on the stereo image corrected by the image correcting section 60 (S408). The process is returned when the precise shape or coordinate values of the sample 9 can be acquired (S410). Preferably, in order to allow an observation of the sample, the stereo image corrected by the image correcting section 60 may be displayed on the display device 28.

In the embodiment above, calibration data for the electron beam measuring device prepared by the calibration data preparing section may include calibration data on the tilt amount by the sample tilting section 5, calibration data on the irradiation direction of the electron beam 7 irradiated by the electron optical system 2, calibration data on the magnification of the electron optical system 2, and calibration data on distortion correction for the electron optical system 2. However, this invention is not limited thereto. In short, calibration data prepared by the calibration data preparing section may include such data that allows the calibration section to perform a calibration to reduce aberration in an image of the sample detected by the electron beam detecting section 4.

Before describing a fifth and subsequent embodiments, a principle relating to this invention is described. As described previously, the left image is photographed at an angle θ1 and the right image is photographed at an angle θ2, and a Z'-axis titled at an angle θ' with respect to the Z-axis is assumed. Then, for FIG. 14, the equations (14) and (15) hold true.

Principle

The basic principle of this invention is as follows. Known shape data on a reference template as a reference sample and data on the reference template obtained with the electron beam measuring device tilted are used to obtain, and store the values of, the tilt angle θ, magnification, and distortion resulting from the electron optical system when the reference template is photographed. In order to measure the sample at a corrected angle, an image is corrected utilizing the tilt angle, magnification, and distortion in the electron optical system calculated in advance for the reference template, to perform a 3D measurement.

Figure 20:
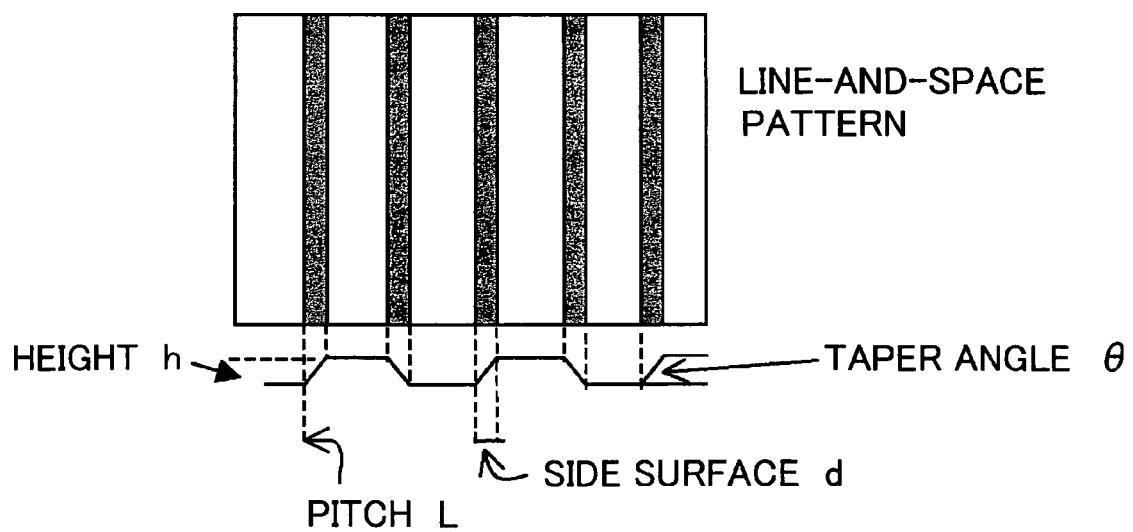
FIG. 20 is a plan view of a reference template configured with a line-and-space pattern.
Figure 21:
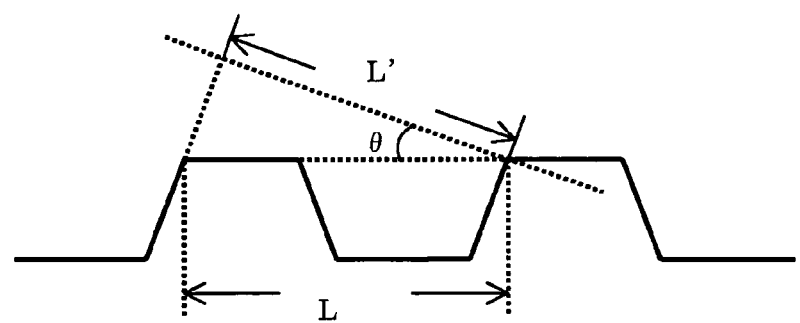
Figure 22:
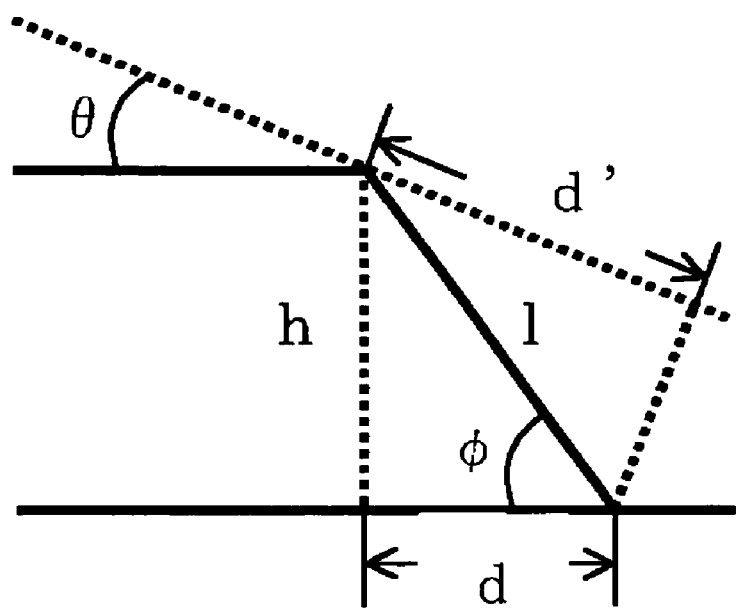
FIG. 22 illustrates specifically a side surface of the reference template of FIG. 20.

The reference template may be a template of a known shape or that of an unknown shape subjected to a measurement. The reference template may have depressions and projections, or may be, for example, of a line-and-space type as shown in FIG. 20. The known data necessary for the reference template may include, as shown in FIGS. 21 and 22, the shape of the depressions and projections, or an interval L between the depressions and projections (in cases of a line-and-space pattern, a pitch interval L), a height h of the depressions and projections, and a taper angle Φ.

From an image obtained by photographing the reference template by the electron beam system according to this invention, the pitch interval L' and a side interval d' (x') are found.

Finding these variables allows calculation of the tilt angle θ and a magnification s when the image is photographed, using the following equations.

Calculating Equation: Calculation of Tilt Angle and Magnification

When an L/S sample with a known pitch interval L [nm], a taper angle Φ [degree], a height h [nm], and a length of a slope l [nm] is photographed with a magnification s [times] and at a tilt angle θ [degree], the s and θ are found as follows.

Assuming the size of a pixel is s [nm], the pitch interval L' [pixel] as tilted at θ can be represented as:

$$L' = L \times \cos\theta / s \qquad \text{E1}$$

The side width d' [pixel] of the sample as tilted at θ can be represented as:

$$d' = 1 \times \cos(\varphi - \theta)/s \qquad \text{E2}$$
$$= (h/\sin\varphi) \times \cos(\varphi - \theta)/s$$

The equations E1 and E2 can be solved for s as follows:

$$L \times \cos\theta/L' = (h/\sin\varphi) \times \cos(\varphi - \theta)/d' \qquad \text{E3}$$
$$= (h/\sin\varphi) \times (\cos\varphi\cos\theta + \sin\varphi\sin\theta)/d'$$
$$\therefore \theta = \tan^{-1}(Ld'/hL' - (1/\tan\varphi))$$

Distortion Correction

Figure 30:
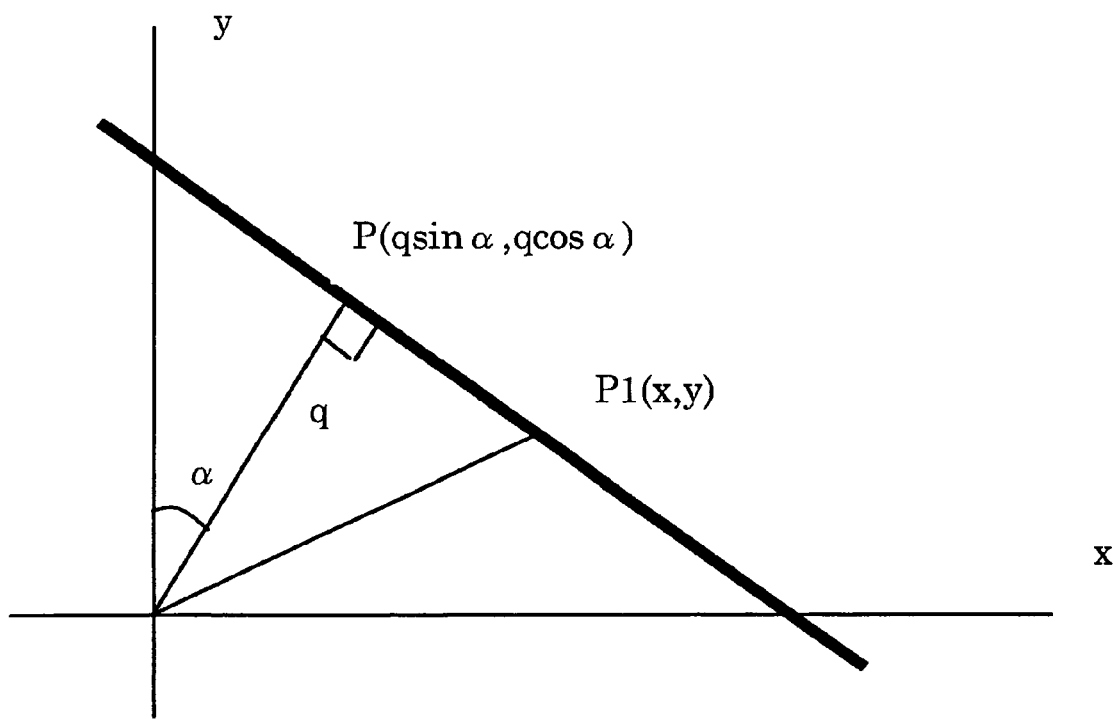
FIG. 30 is a diagram for illustrating equations used to perform a linear approximation of the boundaries between the side surface and the top surface, and between the side surface and the bottom surface, of the reference template as shown in FIG. 20.

A description is made of calculation of distortion correction parameters for the electron optical system. Distortions in the electron optical system can be corrected with an aggregate correction factor for distortion aberration of the lens system, scanning distortion of the electron beam, and other distortion generated in the entire electron optical system. For example, in cases where the reference template is of the line-and-space type as shown in FIG. 20, the boundaries between a side surface and the top surface, and between a side surface and the bottom surface, of the reference template should be straight lines. Therefore, a correction can be made by approximating such portions to straight lines. That is, an approximation to straight lines can be made according to the following equations (see FIG. 30):

$$x \sin \alpha + y \cos \alpha = q$$

In consideration of distortions in the electron optical system, the equation above can be represented as:

$$(x+\Delta x)\sin \alpha + (y+\Delta y)\cos \alpha = q$$

where Δx and Δy represent a distortion amount.

The equations above indicate the condition that a number of points (currently curved due to the distortions) on the boundaries between a side surface and the bottom surface, and between a side surface and the top surface, should be "on straight lines". A distorted model is adjusted so as to correct such points to be on straight lines.

Concerning lens distortion correction, in order to find distortion aberration of the electron lenses constituting the electron optical system 2, the equations (4) and (5) described previously should hold true, and correction is possible by using the equation (4).

Distortion aberration of the electron lenses can be calculated by measuring image coordinates and object coordinates, substituting the measured coordinates into the equation above, and using the successive approximation method. Since unknown variables increase with the lens distortion factors, distortion aberration of the electron lenses may conveniently be calculated by measuring image coordinates and object coordinates with a multiplicity of points on the straight lines as reference points, substituting the coordinates into the equation, and using the successive approximation method. In the case of the equation (5), the lens distortion factors are represented by radial lens distortion. However, any element necessary for correction of tangential lens distortion, spiral lens distortion, or other distortion aberration of the electron lenses may be incorporated into the equation (5) to find respective lens distortion factors, to allow calibration of such lens distortions.

For example, utilizing the found lens distortion factors, scanning of a beam can be performed in such a manner as to correct the lens distortions, resulting in a corrected image acquired. Alternatively, the lens distortions can be stored in a memory and scanning of a beam can be performed in such a manner as to correct the lens distortions, to allow lens distortion correction on an image.

As has been described above, the reference template can be tilted at a desired angle, and the actual tilt angle, magnification, and distortion in the electron optical system under that condition can be found and stored in advance. By utilizing such stored values when the sample or the beam is tilted to measure the sample, an accurate three-dimensional shape can be found. Tilt angles used in the measurement may be found and respective correction factors corresponding to the tilt angles may be found by calculations, to perform a correction.

Figure 24:
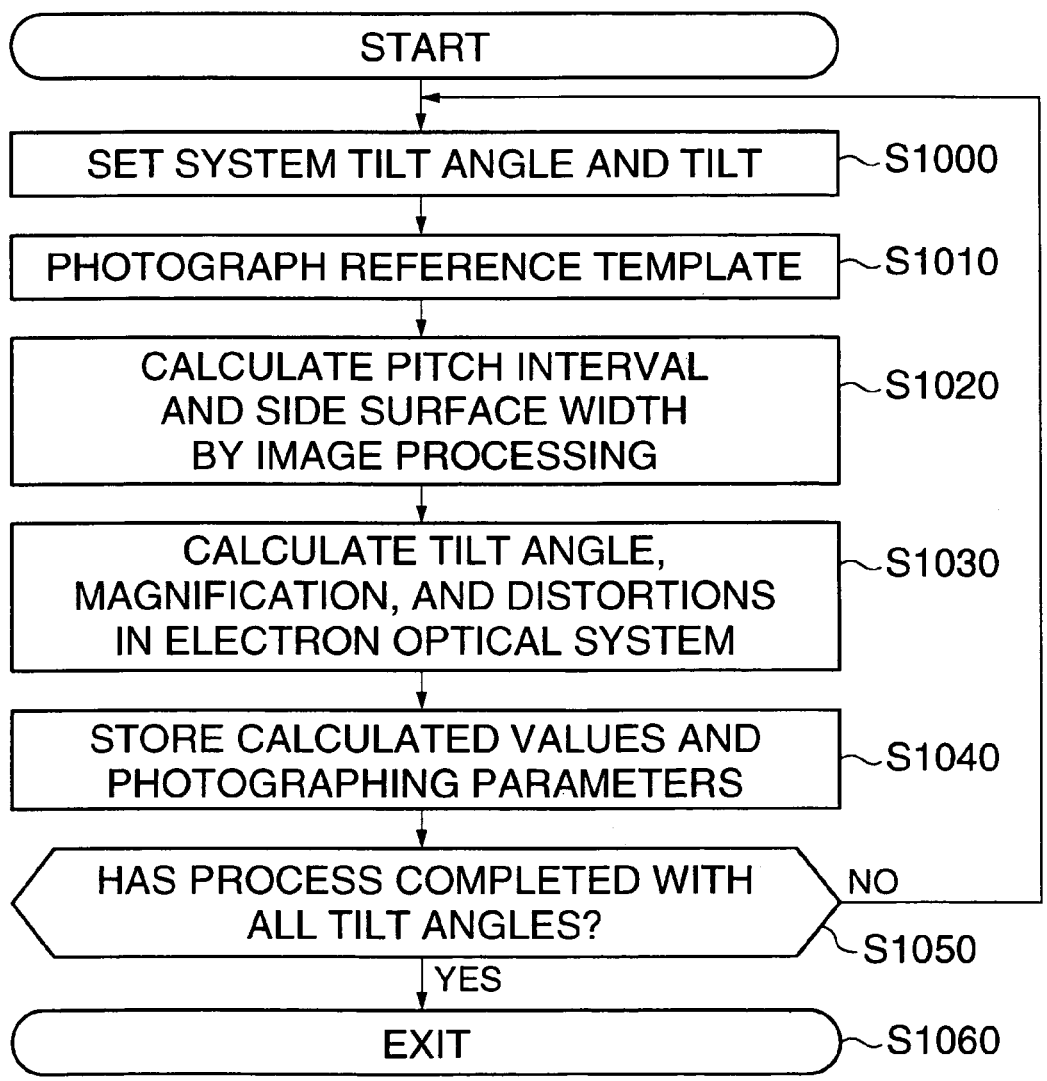
FIG. 24 is a flowchart of preprocessing, illustrating a procedure for finding an accurate three-dimensional shape.

According to the flowchart of FIG. 24, the procedure is described.

FIG. 20 shows a line-and-space pattern, as an example, on a reference template 9a, FIG. 21 illustrates the pitch interval and tilt of the space-and-line pattern, and FIG. 22 illustrates a side surface portion of the reference template 9a. For example, the reference template 9a may have a line-and-space pattern as shown, for example, in FIG. 20. The reference template may be a pitch standard or the like sold on the market as a reference template. If such a reference template is not available, a measuring device such as a CD-AFM may be used to measure a line-and-space pattern as shown in FIG. 20. When a reference template available on the market is used, the values of the pitch interval L, taper angle Φ, and height h of a sample can be utilized from the reference template, and otherwise, such data must be measured in advance.

S1000: Set the tilt angle of the sample or the beam of the electron beam measuring device to tilt it. The tilt angle is set to all, or a number of typical ones of, the tilt angles at which a measurement is desired to be performed in advance.

S1010: Photograph the reference template by the electron beam measuring device.

S1020: Calculate the pitch interval L' and the side surface width d' (x') of the photographed reference template through image conversion.

Line Edge Detection Process

In order to precisely calculate the pitch interval on the image and to correct the magnification or angle, the edges of the lines and the spaces should be found with sub-pixel accuracy. A method for doing this is to apply a linear detection operator to the acquired image of the reference template (the standard) and detect edge points. The linear detection operator may be of any type such as a 3×3 filter type commonly used in image processing.

Figure 32:
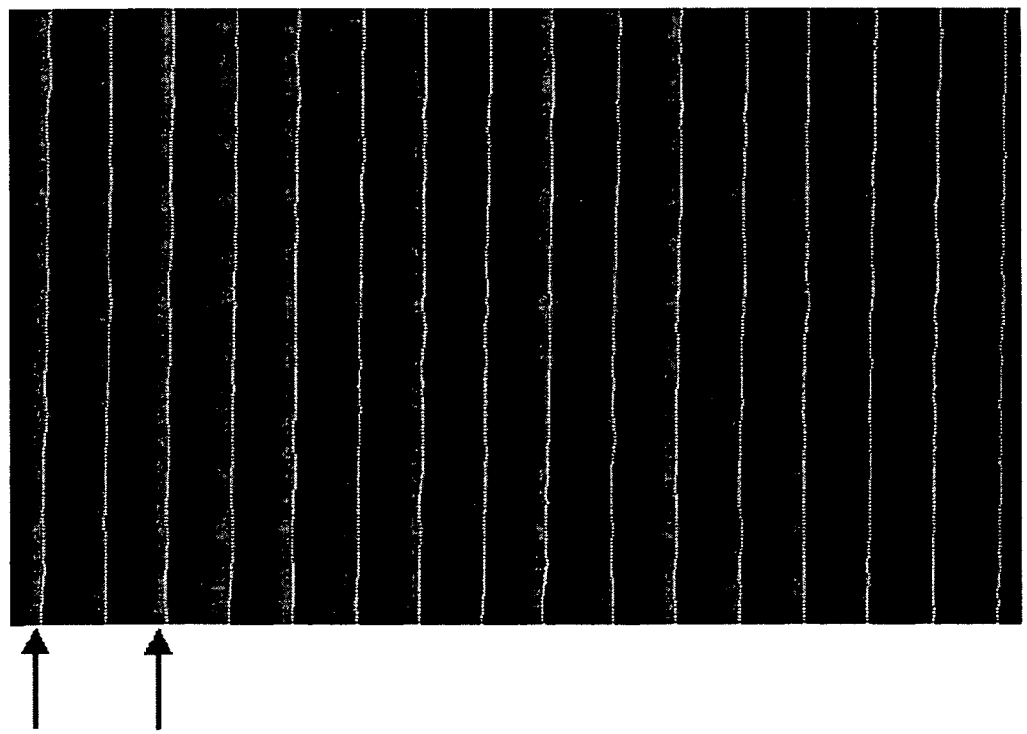
FIG. 32 shows an example of edges actually detected.

Based on all the found edge points and utilizing the connectivity of the edges, a group of edges connected to a greater degree than a threshold value are recognized as a line (straight line) of the reference template. FIG. 32 shows an example of edges actually detected.

S1030: Calculate the tilt angle, magnification, and distortion caused by the electron optical system when the reference template is photographed.

The calculation is performed using the equations previously described in the Principle section.

S1040: Store the calculated tilt angle, magnification, and distortion parameters in the correction factor storing section.

S1050: If the calculation is finished with all the set tilt angles, the process terminates; otherwise the process returns to S1000, to repeatedly calculate the parameters for different tilt angles.

In an device constituted as described above, the electron beam measuring device acquires a shape in the image of the reference template at each tilt angle, and acquires the tilt angle and magnification necessary for three-dimensional measurement, and correction factors for removing image distortion caused by the electron optical system, from the reference template subjected to a measurement in advance. Then, a sample 9 is placed on the sample holder 3 in place of the reference template, and an image of the sample 9 as a subject is acquired at an arbitrary tilt angle by the electron beam measuring device.

Fifth Embodiment

Figure 19A:
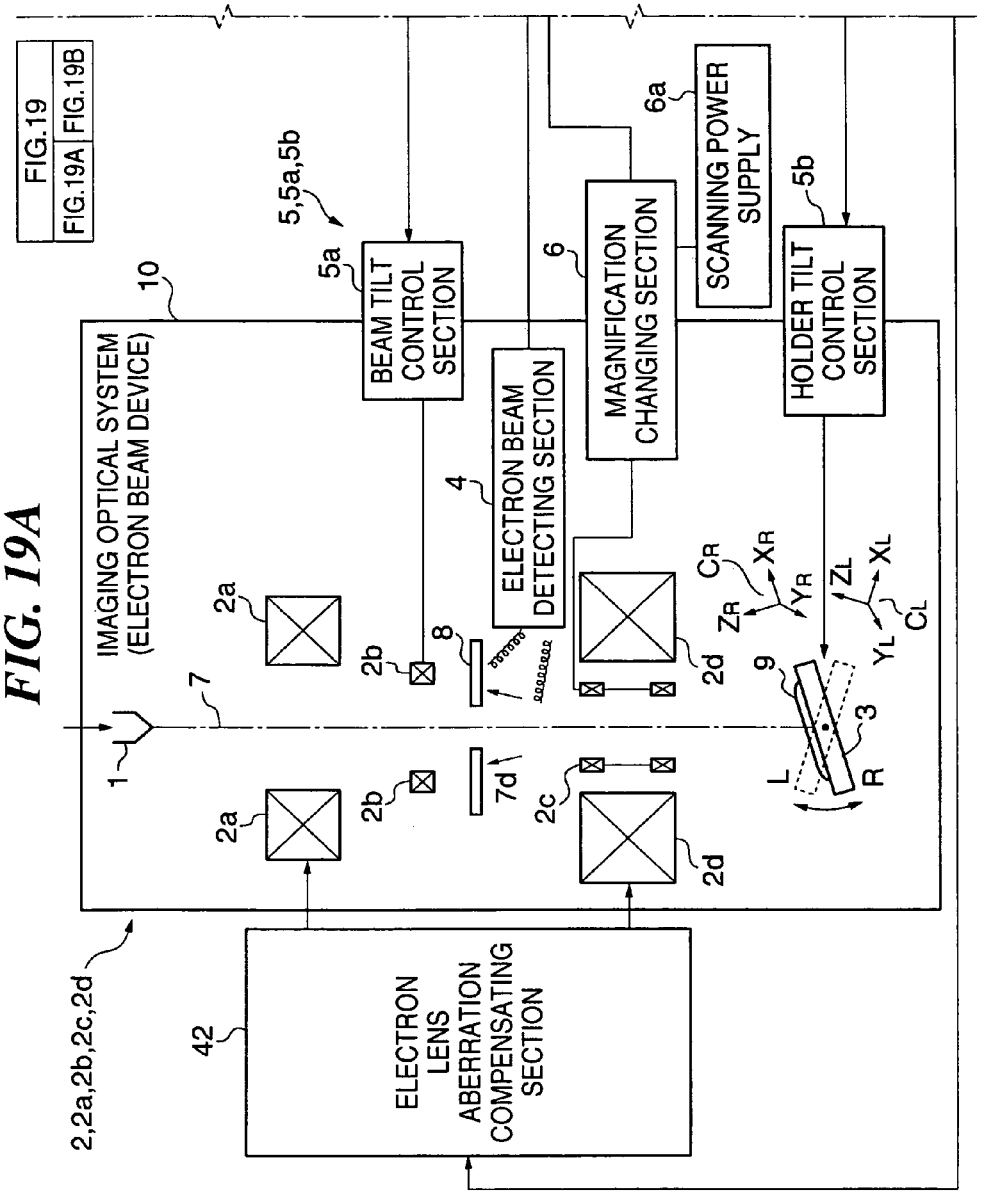
FIG. 19A and FIG. 19B are general block diagrams illustrating the structure of a fifth embodiment of this invention.
Figure 19B:
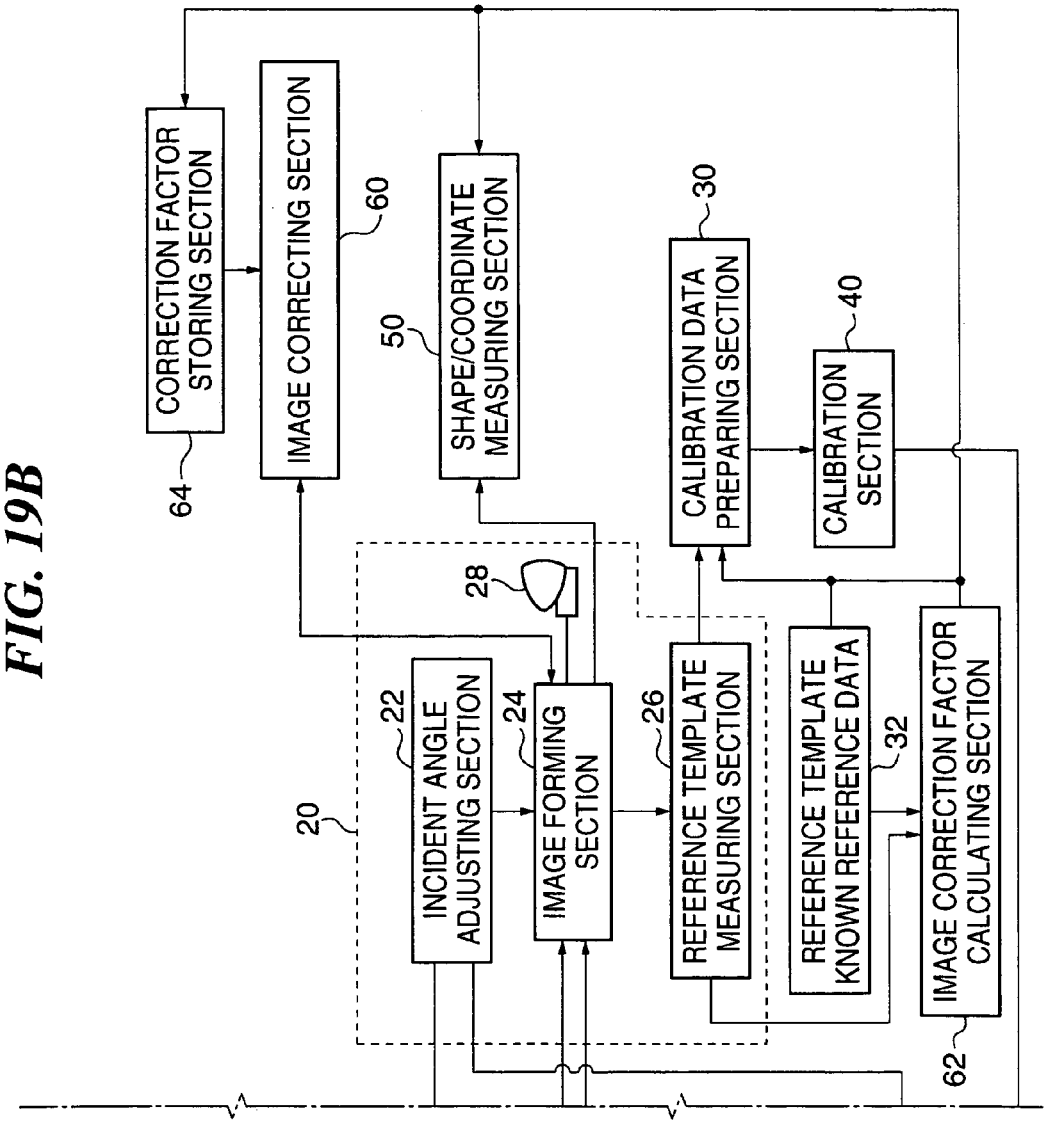

With reference to FIG. 19, a description is made of an embodiment of this invention. FIG. 19 is a block diagram illustrating the structure of a fifth embodiment of this invention. In the fifth embodiment, the rotational angle of a holder for holding an object is adjusted to adjust the tilt angle of the object so that a stereo image of the object can be obtained. As shown in the figure, an electron beam device 10 (scanning electron microscope) as an imaging optical system in an electron beam system includes an electron beam source 1 for emitting an electron beam 7, an electron optical system 2 for irradiating the electron beam 7 on an object 9, a sample holder 3 for tiltably holding the object 9, a magnification changing section 6 for changing the magnification of the electron optical system 2, a scanning power supply 6a for supplying electric power to the magnification changing section 6, a detector 4 for detecting secondary electrons or reflected electrons from the object on which the electron beam 7 is irradiated, a holder tilt control section 5b as a tilt control section 5 for controlling the tilt of the sample holder 3, and a secondary electron converting target 8 for attenuating the energy of the secondary electrons outgoing from the object 9 to reflect the secondary electrons toward the detector 4. A beam tilt control section 5a as the tilt control section 5 for controlling the tilt of the electron beam 7 is not used in the fifth embodiment but used in a seventh embodiment described later.

The electron optical system 2 includes condenser lenses 2a for changing the electron flow density, divergence angle and irradiation area of the electron beam 7 emitted from the electron beam source 1, deflection lenses 2b for controlling the incident angle of the electron beam 7 on a sample surface, scanning lenses 2c for deflecting the electron beam 7 with a reduced diameter to cause it to scan the sample surface two-dimensionally, and objective lenses 2d which focus the incident probe beam on the sample surface and serve as condenser lenses in the final stage. The area on the sample surface which the scanning lenses 2c cause the electron beam 7 to scan is determined according to a magnification change command from the magnification changing section 6. The beam tilt control section 5b sends a tilt control signal to the sample holder 3 to switch it between a first attitude 3L in which it makes a first tilt angle relative to the irradiated electron beam 7 and a second attitude 3R in which it makes a second tilt angle relative to the electron beam 7.

A three-dimensional coordinate system $C_L$ of the object 9 placed on the sample holder in the first attitude 3L can be represented as $(X_L, Y_L, Z_L)$ in a fixed coordinate system of the electron beam device 10. Also, a three-dimensional coordinate system $C_R$ of the object 9 placed on the sample holder in the second attitude 3R can be represented as $(X_R, Y_R, Z_R)$ in a fixed coordinate system of the electron beam device 10. Although the holder tilt control section 5b can switch the tilt angle of the sample holder 3 relative to the irradiated electron beam 7 between an angle R tilted upward to the right and an angle L tilted upward to the left in the figure, the sample holder 3 may be configured to be tilted at a multiplicity of angles, not limited to two angles. At least two angles are necessary to obtain stereo detection data.

When a yaw axis, a pitch axis and a roll axis, for example, are set as a three-dimensional coordinate system of the object 9, the yaw axis, the pitch axis and the roll axis correspond to Z-axis, X-axis and Y-axis, respectively.

The object 9 is a chip of a semiconductor material such as a silicon semiconductor or a gallium arsenide semiconductor, or may be an electronic component such as a power transistor, a diode or a thyristor, or may be a display device component using glass such as a liquid crystal panel or an organic EL panel. Under typical observing conditions for a scanning electron microscope, the electron beam source 1 is set to a potential of −3 kV and the object 9 to −2.4 kV. Secondary electrons released from the object 9 are attenuated in energy as they collide with the secondary electron converting target 8 and detected by the detector 4.

As shown in FIG. 19, the electron beam system includes a measuring section 20 as a first measuring section, a calibration data preparing section 30, a known reference data storing section 32, a calibration section 40, an electron lens aberration compensating section 42, a shape/coordinate measuring section 50, an image correcting section 60, a correction factor calculating section 62, and a correction factor storing section 64.

The measuring section 20 is adapted to tilt the reference template 9a held by the sample holder 3 relative to the irradiated electron beam 7 by means of the sample tilting section 5, to find the shape or coordinate values (pitch interval L, taper angle Φ, height h, and/or the like) of the reference template 9a based on an image of the reference template 9a photographed by the electron beam detecting section 4. The measuring section 20 has an incident angle adjusting section 22, an image forming section 24, a reference template measuring section 26, and a display device 28.

The incident angle adjusting section 22 adjusts the attitude of the object 9 (including the reference template 9a), to adjust the incident angle of the electron beam 7 projected from the electron beam device 10 onto the object 9 relative to the object 9 so that a stereo image of the object 9 can be formed. That is, the incident angle adjusting section 22 transmits a control signal to the holder tilt control section 5b to adjust the attitude of the object 9. In addition, the incident angle adjusting section 22 transmits a control signal to the holder tilt control section 5b to adjust a reference surface to be scanned by the electron beam 7 emitted from the electron beam source 1 so that right and left images necessary to form a stereo image can be formed. The image forming section 24 forms an image of the sample surface using a secondary electron beam detected by the detector 4 when the electron beam 7 is caused to scan a region on the sample surface by the scanning lenses 2c. The reference template measuring section 26 finds the shape or coordinate values of the reference template 9a based on the image of the reference template 9a photographed by the electron beam detecting section 4. The display device 28 is adapted to display right and left images constituting the stereo image of the object 9 (including the reference template 9a) photographed by the electron beam detecting section 4. A CRT or liquid crystal display, for example, may be used as the display device 28.

The calibration data preparing section 30 utilizes the measurement results of the reference template by the measuring section 20 and known reference data on the reference template 9a, to prepare a correction factor and/or calibration data for a stereo image photographed by the electron beam system. The reference template known reference data storing section 32 stores the shape (pitch interval, taper angle, height, and/or the like) of the reference template 9a. Calibration data for the electron beam system prepared by the calibration data preparing section 30 may include:

(1) calibration data on the tilt amount by the sample tilting section 5,
(2) calibration data on the irradiation direction of the electron beam 7 irradiated by the electron optical system 2,
(3) calibration data on the magnification of the electron optical system 2, and
(4) calibration data on distortion correction for the electron optical system 2.

The calibration section 40 performs a calibration based on the calibration data so as to reduce aberration in an image of the sample detected by the electron beam detecting section 4. Depending on the foregoing calibration data for the electron beam system prepared by the calibration data preparing section 30, the calibration section 40 may be configured to:

(1) calibrate the tilt amount by the sample tilting section 5,
(2) calibrate the irradiation direction of the electron beam 7 irradiated by the electron optical system 2,
(3) calibrate the scanning range of the electron optical system 2, and
(4) calibrate the scanning direction of a scan coil of the electron optical system 2.

The electron lens aberration compensating section 42 compensates for the distribution states of magnetic potentials and electrostatic potentials of the electron lenses constituting the electron optical system 2 according to a calibration signal outputted from the calibration section 40 so as to reduce aberration in an image of the sample, thereby adjusting the electron optical system 2 to be suitable for image measurement. The electron beam device 10 may have an electromagnetic prism called ExB that separates secondary electrons emitted from the sample 9, from the electron beam 7 emitted from the electron beam source 1, to send the secondary electrons to the electron beam detecting section 4. In such cases, the electron optical system 2 as an object of calibration by the calibration section 40 should include such an electromagnetic prism called ExB.

The shape/coordinate measuring section 50 finds the shape or coordinate values of the sample 9 based on the stereo image, photographed by the electron beam detecting section 4, of the sample 9 placed in a tilt state created by the sample tilting section 5 on the sample holder 3, where the sample 9 is calibrated by the calibration section 40. The shape/coordinate measuring section 50 uses the incident angle adjusting section 22, the image forming section 24, and the display device 28 of the measuring section 20, in common with the reference template measuring section 26.

Figure 25:
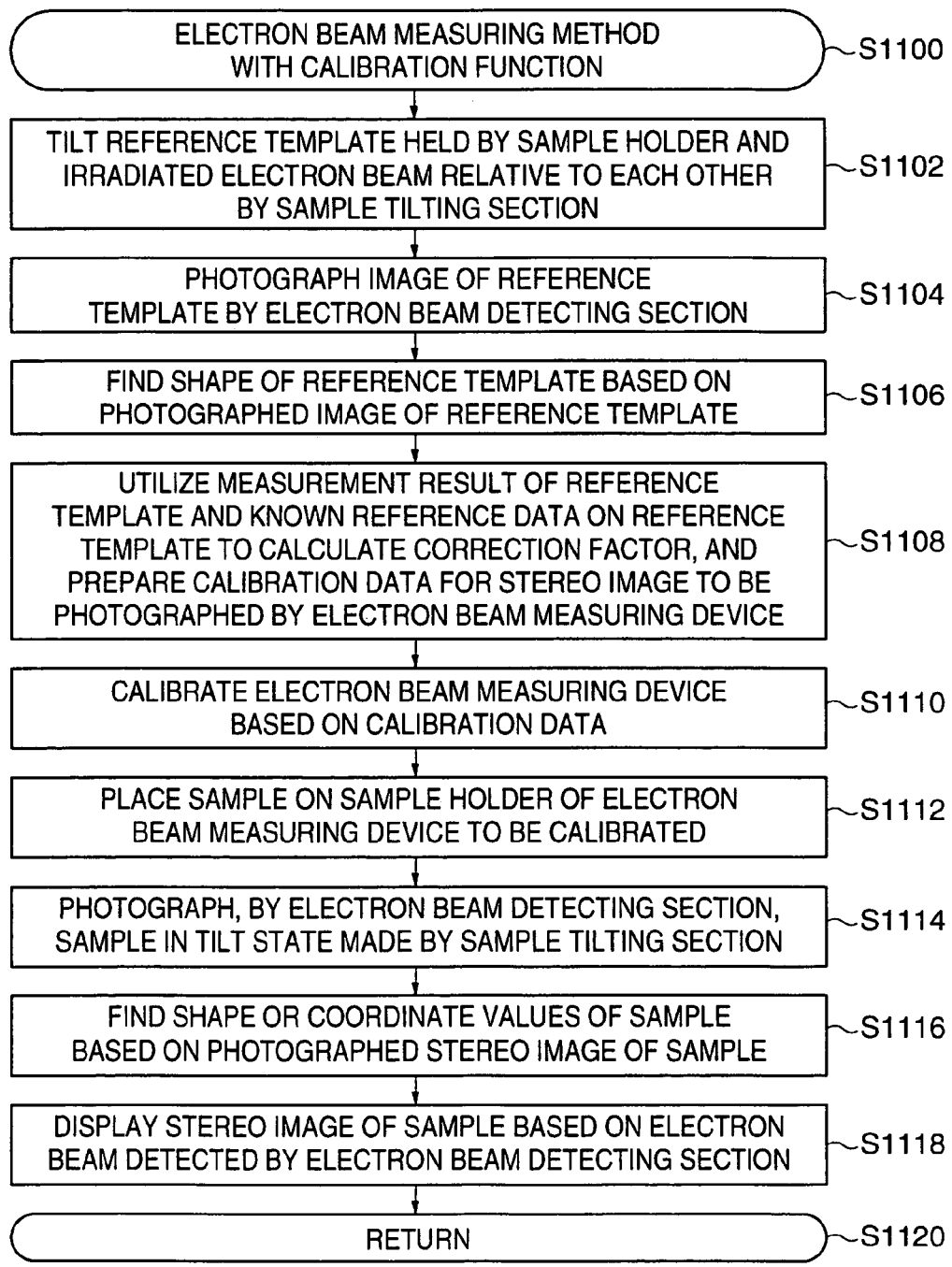
FIG. 25 is a flowchart of electron beam measurement including the calibration procedure for an electron beam device according to the fifth embodiment of this invention.

With reference to FIG. 25, a description is made of the calibration procedure for an electron beam device necessary for stereo image measurement by an device constituted as described above. FIG. 25 is a flowchart of electron beam measurement including the calibration procedure for the electron beam device according to the fifth embodiment of this invention. FIG. 25 shows a process flow of calibration of the electron beam device using the reference template 9a, and of subsequent measurement of an image of the sample (S1100). A reference template 9a is placed on the sample holder 3, to bring the sample holder 3 or the electron beam 7 into a tilt state (S1102). For example, the beam tilt control section 5b transmits a tilt control signal to the sample holder 3 and the incident angle adjusting section 22 adjusts the incident angle of the electron beam 7 relative to the object 9. The tilt angle is set with respect to the tilt angle of the reference template 9a to be measured. For example, the tilt angle is set to the tilt state shown in FIG. 2A or FIG. 2B.

When there are a plurality of tilt angles, an image may conveniently be acquired at all the tilt angles at which a measurement may possibly be performed.

The measuring section 20 acquires a tilted image of the reference template 9a from the electron beam detecting section 4 (S1104). The measuring section 20 finds the shape of the reference template 9a based on the image of the reference template 9a photographed by the electron beam detecting section 4 (S1106). The edge extraction process described in the Principle section may conveniently be used in S1106.

The calibration data preparing section 30 utilizes the measurement results of the reference template 9a in S1106 and known reference data on the reference template 9a to calculate a correction factor (as described in the Principle section), to prepare calibration data for a stereo image photographed by the electron beam device 10 (S1108). The calibration section 40 performs a calibration of the electron beam device 10 based on the calibration data so as to reduce aberration in an image of the sample detected by the electron beam detecting section 4 (S1110).

Then, a sample (measuring object) 9 is placed on the sample holder 3 (S1112). The electron beam 7 or the sample holder 3 is brought into a desired tilt state, to allow the sample 9 to be photographed by the electron beam detecting section 4 (S1114). As the desired tilt state, an angle at which much of the sample 9 can be viewed with a minimum blind spots or an angle at which the targets particularly desired to be measured can be satisfactorily photographed may be selected, for example, when three-dimensional image measurement of the sample 9 is performed. The shape or coordinate values of the sample 9 are found based on the stereo image of the sample 9 in the desired tilt state (S1116). This process is achieved by the stereo matching process using two stereo images. As the desired tilt state, an angle at which much of the sample 9 can be viewed with minimum blind spots or an angle at which the targets particularly desired to be measured can be satisfactorily photographed may be selected, for example, when three-dimensional image measurement of the sample 9 is performed.

The stereo matching process is the same as described with reference to FIG. 10.

Then, the correction factor calculating section 62 (see FIG. 19) finds a first correction factor for bringing the non-reference image into the reference image in a distorted state, using the selected reference image and applying the correspondence between the stereo-pair images to the non-reference image of the stereo-pair tilted images. This process is also the same as described previously. The found first correction factor is stored, for example, in the correction factor storing section 64 so as to be available, for example, to the measuring section 20, the shape/coordinate measuring section 50, and the image correcting section 60. The found first correction factor is used to convert an image while correcting image distortion, by a variety of operational processes such as making a model using points detected with a calibration method using parallel projection, a curved-line approximation method using a least squares method, a method of making an approximation using an affine transformation, and of finding a factor used to make the approximation, or the like.

In order to allow an observation of the sample, the stereo image of the sample 9 is displayed on the display device 28 based on the electron beam detected by the electron beam detecting section 4 (S1118). The process is returned when the shape or coordinate values of the sample 9 can be acquired (S1120).

In the description so far, a calibration is performed using the calibration data preparing section 30, the calibration section 40, and the electron lens aberration compensating section 42. However, such components can be dispensed with in cases where the image correcting section 60 can correct an image using a correction factor calculated with the correction factor calculating section 62, and the shape/coordinate measuring section 50 can obtain three-dimensional measurement values, to thereby allow an accurate correction.

In such cases, a preparation of calibration data in S1108 and a calibration of the electron beam system based on the calibration data in S1110 in the flowchart of FIG. 25 are not necessary.

The parallel projection is the same as described with reference to FIG. 5. In the parallel projection, the equations (1), (2), and (3) hold true.

Sixth Embodiment

Figure 26A:
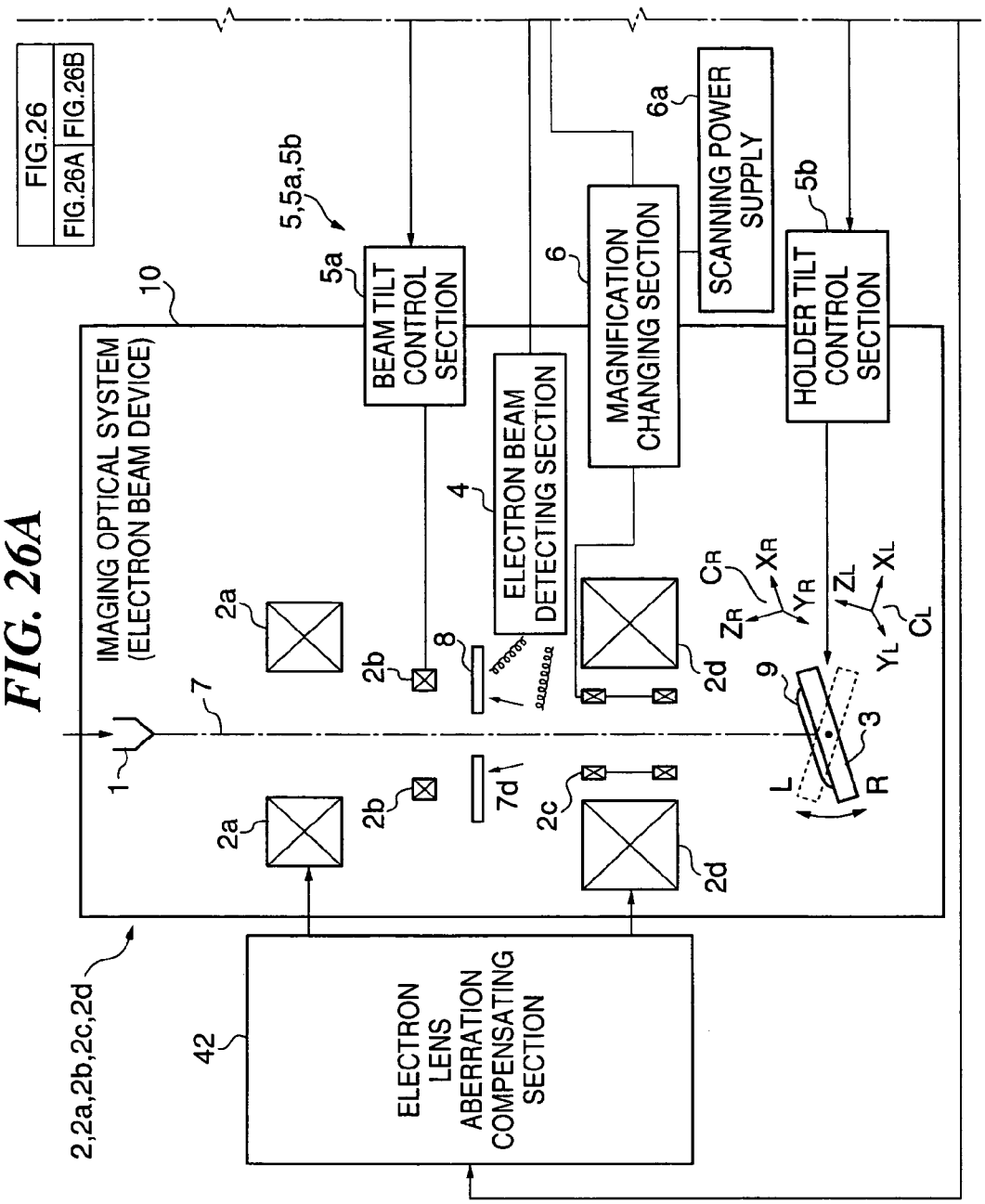
FIG. 26A and FIG. 26B are block diagrams illustrating the structure of a sixth embodiment of this invention.
Figure 26B:
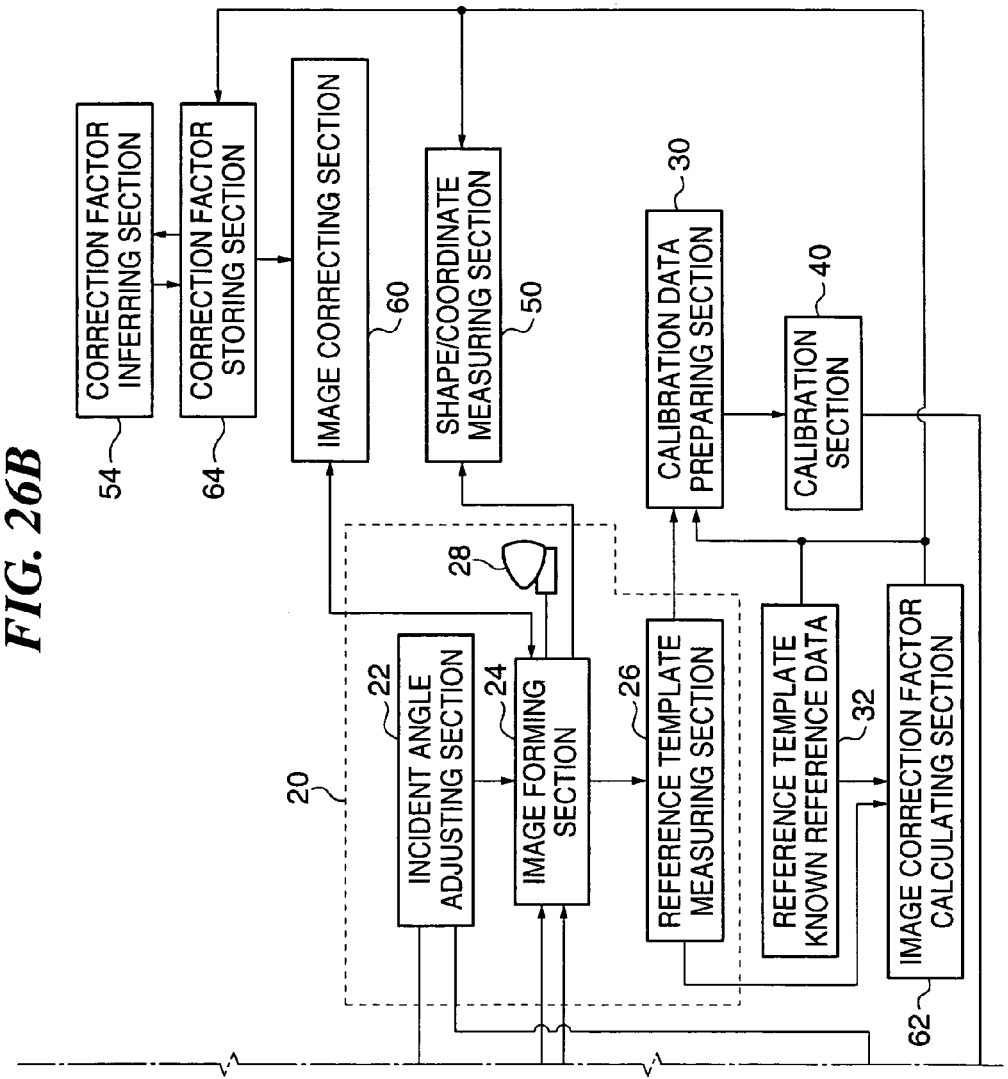

FIG. 26 is a block diagram illustrating the structure of a sixth embodiment of this invention. As shown in the figure, the electron beam system includes the measuring section 20, the calibration data preparing section 30, the known reference data storing section 32, the calibration section 40, the electron lens aberration compensating section 42, the shape/coordinate measuring section 50, the image correcting section 60, the correction factor calculating section 62 and the correction factor storing section 64 described above, and a correction factor inferring section 54. The calibration data preparing section 30, the known reference data storing section 32, the calibration section 40, the correction factor calculating section 62, the correction factor storing section 64, the correction factor inferring section 54, and the like constitute a data processing section.

The correction factor storing section 64 stores correction factors for the tilt angle, magnification, electron optical system, and the like at each tilt angle. The correction factor inferring section 54, on the other hand, finds correction factors at a tilt angle where no such correction factors are stored, by making an inference (interpolation) from the stored correction factors.

The inference (interpolation) can be made by preparing a correction function for each factor using a curve-fitting or the other method. Addition of this function allows an accurate three-dimensional measurement where an image can be photographed from any angle and corrected.

Figure 27:
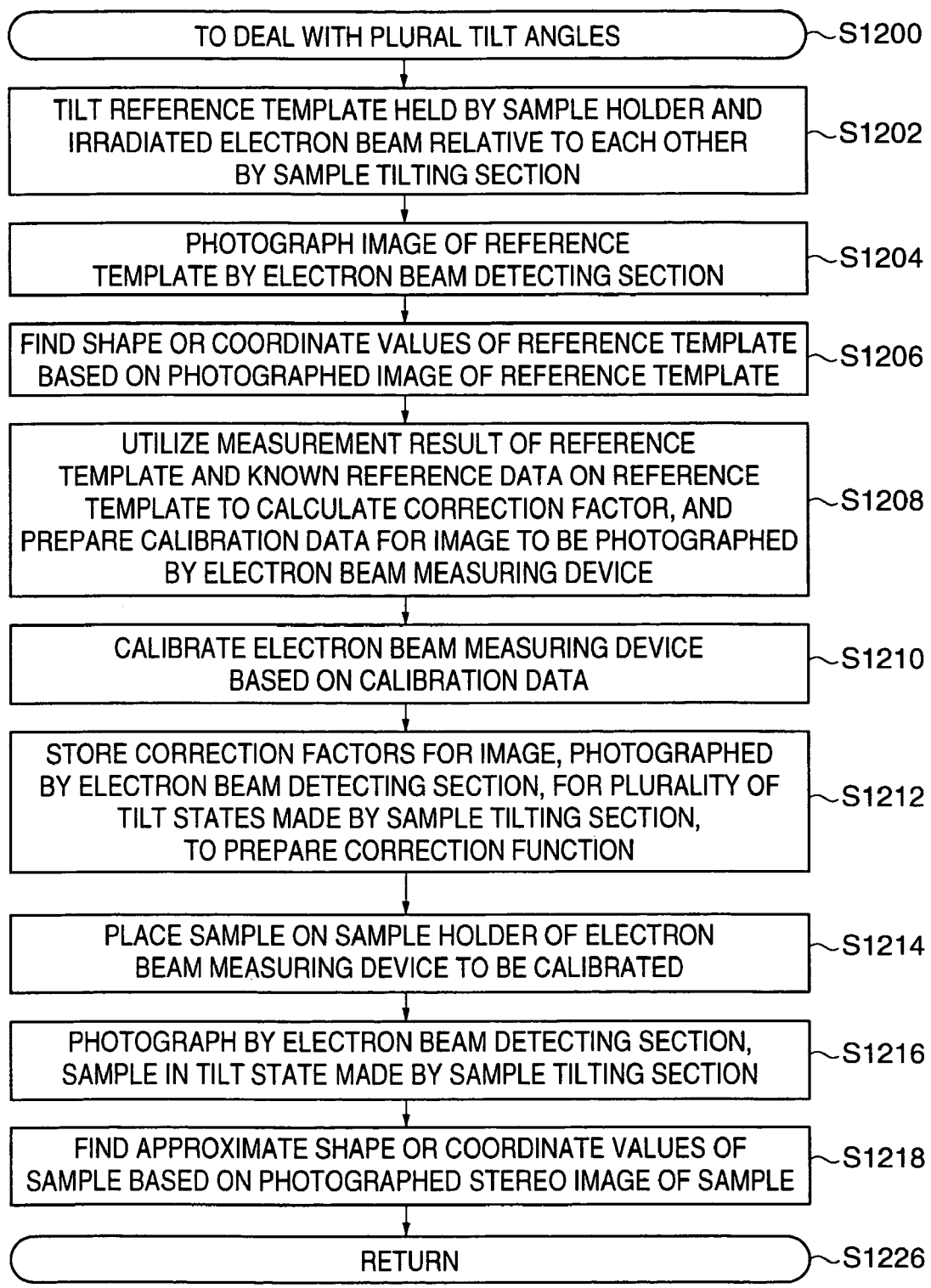
FIG. 27 is a flowchart of electron beam measurement including the calibration procedure for an electron beam device according to the sixth embodiment of this invention.

With reference to FIG. 27, a description is made of the calibration procedure for an electron beam device necessary for stereo image measurement by an device constituted as described above. FIG. 27 is a flowchart of electron beam measurement including the calibration procedure for the electron beam device according to the seventh embodiment of this invention. FIG. 27 shows a process flow of calibration of the electron beam device using the reference template 9a, and of subsequent measurement of an image of the sample (S1200). The processes in S1202 to S1210 are the same as described previously in S1102 to S1110. That is, a reference template 9a is placed on the sample holder 3, to bring the sample holder 3 or the electron beam 7 into a tilt state (S1202). The measuring section 20 acquires a tilted image of the reference template 9a from the electron beam detecting section 4 (S1204). The measuring section 20 finds the shape or coordinate values of the reference template 9a based on the image of the reference template 9a photographed by the electron beam detecting section 4 (S1206). The calibration data preparing section 30 utilizes the measurement results of the reference template 9a in S1206 and known reference data on the reference template 9a to calculate a correction factor, to prepare calibration data for an image photographed by the electron beam device 10 (S1208). The calibration section 40 performs a calibration of the electron beam device 10 based on the calibration data so as to reduce aberration in an image of the sample detected by the electron beam detecting section 4 (S1210). The correction factor calculating section 62 calculates correction factors for an image, photographed by the electron beam detecting section 4, in a plurality of tilt states made by the sample tilting section 5, and the correction factor storing section 64 stores the calculated correction factors, and the correction factor inferring section 54 prepares a correction function for a variety of correction factors at tilt angles (S1212).

Then, a sample (measuring object) 9 is placed on the sample holder 3 (S1214). The electron beam 7 or the sample holder 3 is brought into a desired tilt state, to allow the sample 9 to be photographed by the electron beam detecting section 4 (S1216). As the desired tilt state, an angle at which much of the sample 9 can be viewed with minimum blind spots or an angle at which the targets particularly desired to be measured can be satisfactorily photographed may be selected, for example, when three-dimensional image measurement of the sample 9 is performed. The approximate measurement section 52 finds the shape or coordinate values of the sample 9 based on the stereo image of the sample 9 in the desired tilt state (S1218).

The process is returned when the precise shape or coordinate values of the sample 9 can be acquired (S1226). Preferably, in order to allow an observation of the sample, the stereo image corrected by the image correcting section 60 may be displayed on the display device 28.

In cases where a plurality of tilt directions are used, multi-matching (where corresponding points are found from more than two images to be measured) may be performed in addition to the stereo matching. In such cases, the correction factors are utilized, as a matter of course.

Figure 31:
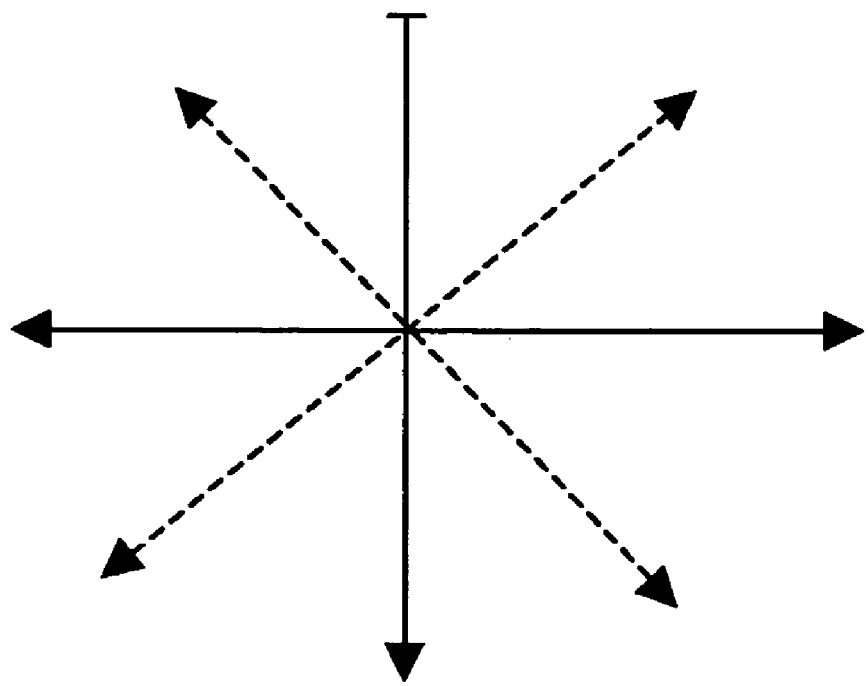
FIG. 31 shows that the tilting is not limited to one axial direction but may be in perpendicular and/or oblique directions.

The tilt direction is not limited to one axial direction. As shown in FIG. 31, perpendicular and/or oblique directions may be used to calculate respective correction factors, to deal with a tilt in any direction.

As shown in FIG. 23, in order to deal with such a plurality of directions, a reference template with patterns in a plurality of directions may be used for correction. The process with such a template is the same as already described except that the process is repeated for the plurality of directions, and therefore is not described here.

Seventh Embodiment

Figure 28A:
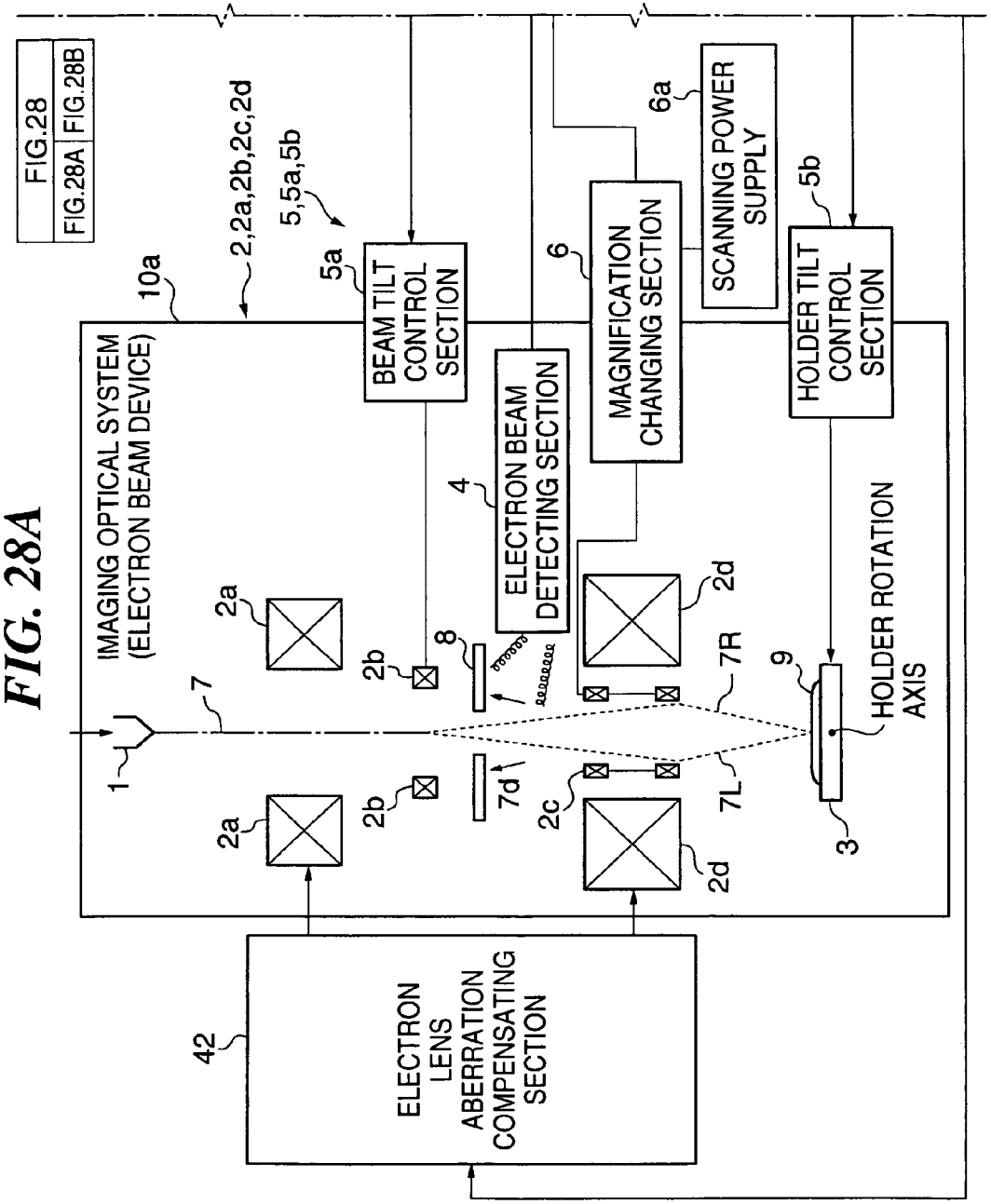
FIG. 28A and FIG. 28B are general block diagrams illustrating the structure of a seventh embodiment of this invention.
Figure 28B:
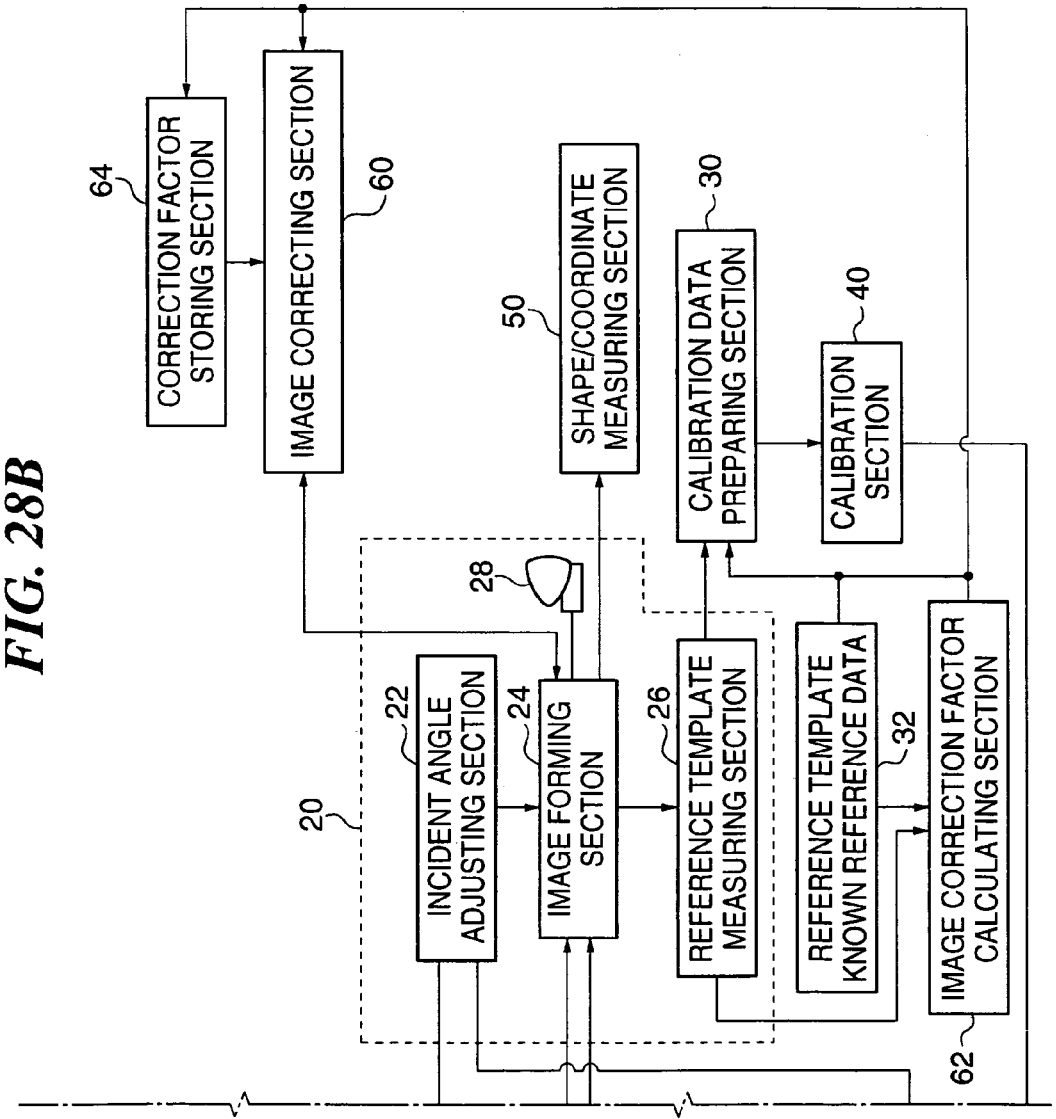

FIG. 28 is a general block diagram illustrating the structure of a seventh embodiment of this invention. In the seventh embodiment, the electron beam of the scanning electron microscope 10a is deflected to obtain a stereo image, unlike the fifth and sixth embodiments, where the holder is tilted to obtain a stereo image. In FIG. 28, components corresponding to those in FIG. 19 are given the same reference numerals and symbols, and descriptions of them are not repeated. A beam tilt control section 5a for controlling the tilt of the electron beam 7 is provided as the tilt control section 5. The beam tilt control section 5a transmits a tilt control signal to the deflection lenses 2b so that the irradiated electron beam is switched between an electron beam 7R which makes a first tilt angle relative to the sample holder 3 and an electron beam 7L which makes a second tilt angle relative to the sample holder 3. The beam tilt control section 5a may be able to adjust the relative tilt angle between the irradiated electron beam 7 and the sample holder 3 to a multiplicity of angles, not limited to two angles. At least two angles are necessary to obtain stereo detection data.

Eighth Embodiment

Figure 29A:
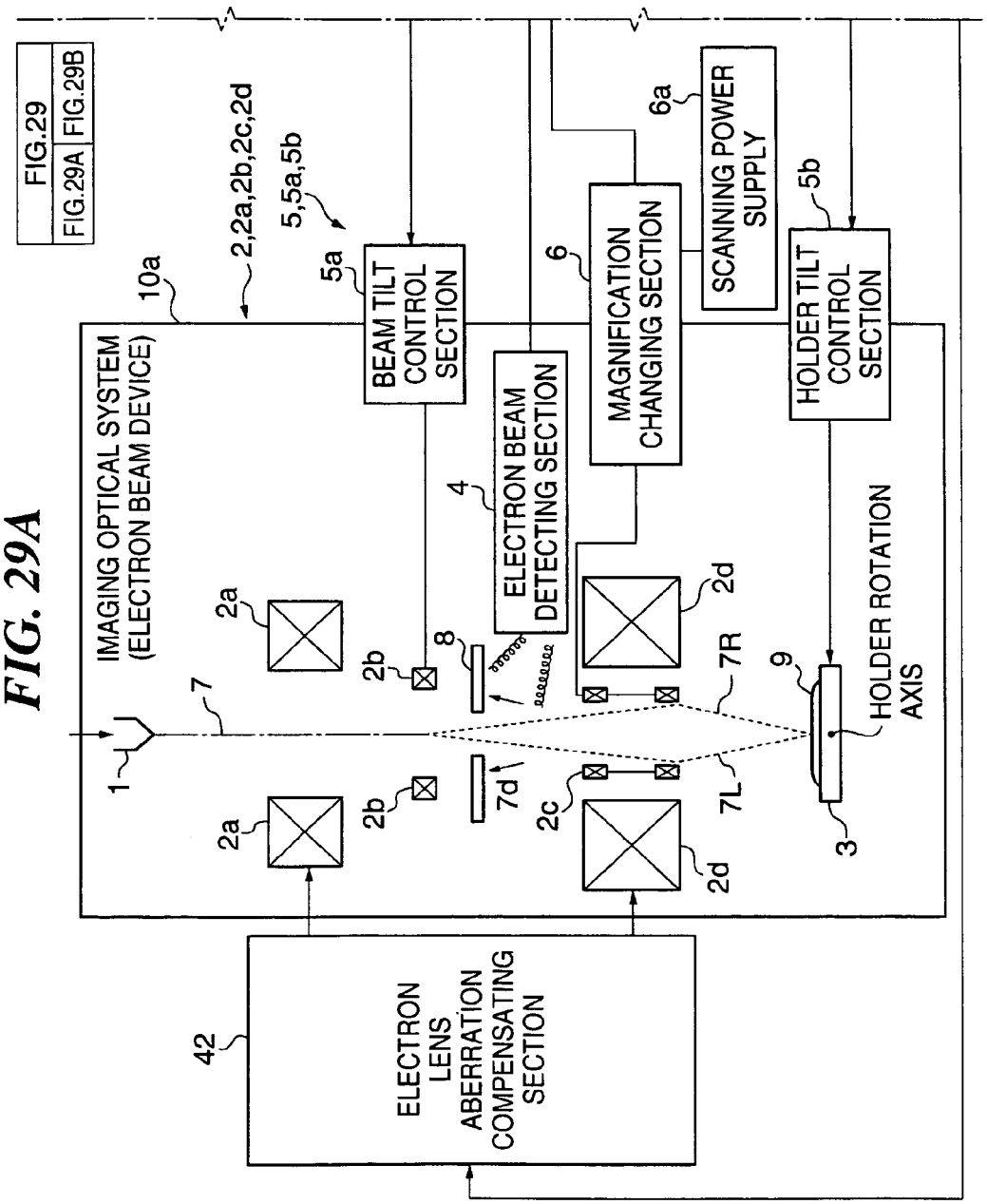
FIG. 29A and FIG. 29B are general block diagrams illustrating the structure of an eighth embodiment of this invention.
Figure 29B:
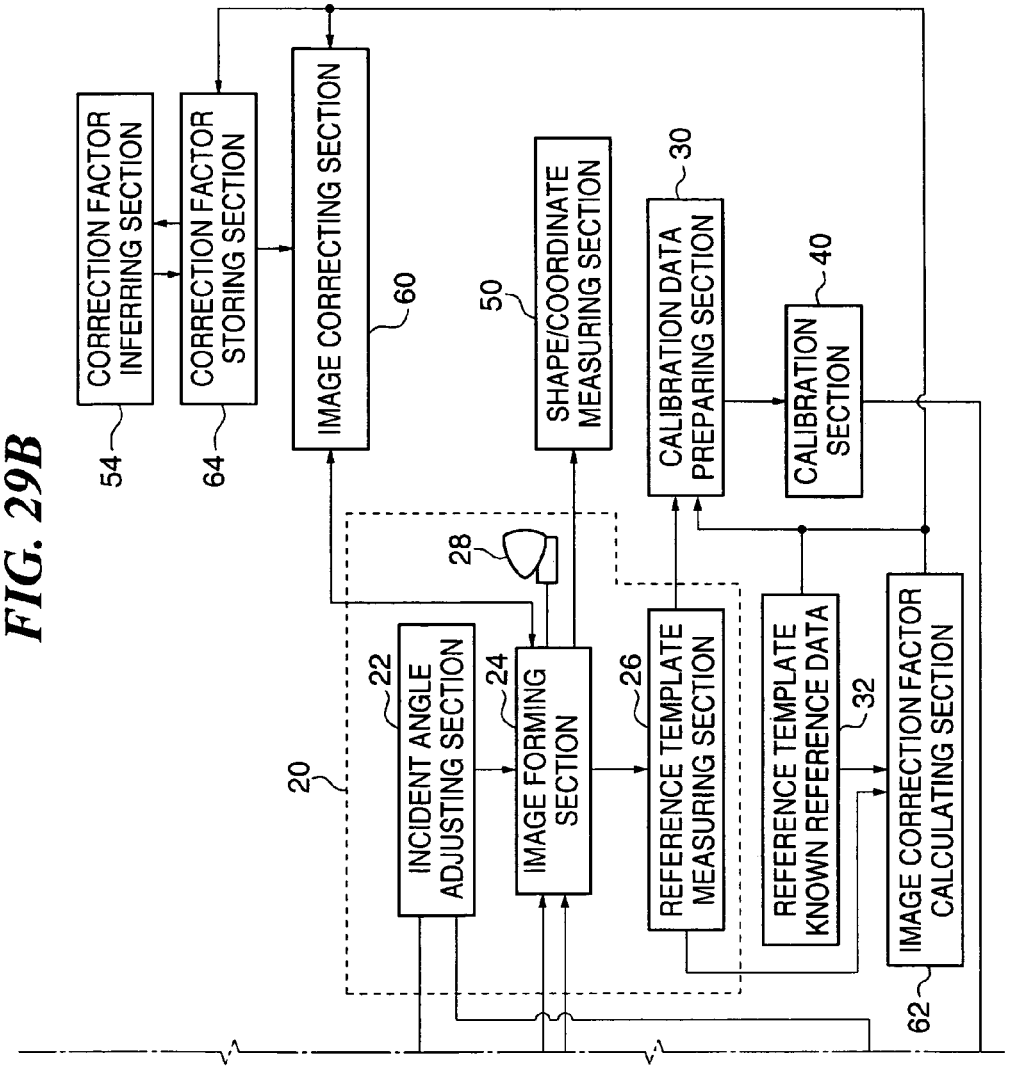

FIG. 29 is a general block diagram illustrating the structure of an eighth embodiment of this invention. The electron beam system includes a shape/coordinate measuring section 50 as a third measuring section, an image correcting section 60, a correction factor calculating section 62, and a correction factor storing section 64, in addition to the measuring section 20 described in relation to the fifth embodiment. The device further includes a correction factor inferring section 54. FIG. 29 is the same as FIG. 26 except that the beam is tilted instead of the sample. Therefore, components in FIG. 29 corresponding to those in FIG. 26 are given the same reference numerals and symbols, and descriptions of them are not repeated.

The operation of the device of the eight embodiment constituted as described above is the same as illustrated in the flowchart of FIG. 27, except that the beam is tilted instead of the sample, and therefore a description of the operation is not repeated.

In the embodiment above, calibration data for the electron beam system prepared by the calibration data preparing section may include calibration data on the tilt amount by the sample tilting section 5, calibration data on the irradiation direction of the electron beam 7 irradiated by the electron optical system 2, calibration data on the magnification of the electron optical system 2, and calibration data on distortion correction for the electron optical system 2. However, this invention is not limited thereto. In short, calibration data prepared by the calibration data preparing section may include such data that allows the calibration section to perform a calibration to reduce aberration in an image of the sample detected by the electron beam detecting section 4.

In the embodiment, a calibration is performed using the calibration data preparing section 30, the calibration section 40, and the electron lens aberration compensating section 42. However, such components can be dispensed with in cases where the image correcting section 60 can correct an image using a correction factor calculated with the correction factor calculating section 62, and the shape/coordinate measuring section 50 can obtain three-dimensional measurement values, to thereby allow an accurate correction.

DESCRIPTION OF REFERENCE NUMERALS
AND SYMBOLS

9: sample (measuring object)
9a, 9c: reference template
10: electron beam device
20: measuring section
30: calibration data preparing section
40: calibration section
50: shape/coordinate measuring section
52: approximate measurement section
54: precise measurement section
60: image correcting section
64: correction factor storing section

What is claimed is:
1. An electron beam system, comprising:
an electron beam source for emitting an electron beam;
an electron optical system for irradiating the electron beam on a sample;

a sample holder for holding the sample;

a sample tilting section for tilting the sample holder and the irradiated electron beam relative to each other so that a stereo image can be acquired;

an electron beam detecting section for detecting an electron beam outgoing from the sample;

a first measuring section for finding a shape or coordinate values of the reference template held by the sample holder based on a stereo image of the reference template photographed by the electron beam detecting section while the reference template and the irradiated electron beam are tilted relative to each other by the sample tilting section;

a calibration data preparing section adapted to compare measurement results of the reference template by the first measuring section with known reference data on the reference template, to prepare calibration data for a stereo image photographed by the electron beam detecting section;

a calibration section for performing a calibration based on the calibration data so as to reduce aberration in an image of the sample detected by the electron beam detecting section; and a second measuring section for finding a shape or coordinate values of the sample based on a stereo image, photographed by the electron beam detecting section, of the sample placed in a tilt state made by the sample tilting section on the sample holder, the sample being calibrated by the calibration section.

2. The electron beam system according to claim 1, further comprising:

a correction factor storing section for storing correction factors for a stereo image, photographed by the electron beam detecting section, for a plurality of tilt states made by the sample tilting section; and an image correcting section adapted to read a correction factor corresponding to a tilt state in which the stereo image is photographed from the correction factor storing section, to correct the stereo image, wherein the second measuring section includes an approximate measurement section for finding an approximate shape or coordinate values of the sample photographed in the stereo image, and a precise measurement section for finding a shape or coordinate values of the sample based on the stereo image corrected by the image correcting section; and the image correcting section is configured to correct the stereo image based on the shape or coordinate values of the sample found by the approximate measurement section and using the correction factor read from the correction factor storing section.

3. An electron beam system, connected to an electron beam device including an electron beam source for emitting an electron beam; an electron optical system for irradiating the electron beam on a sample, a sample holder for holding the sample, a sample tilting section for tilting the sample holder and the irradiated electron beam relative to each other so that a stereo image can be acquired, and an electron beam detecting section for detecting an electron beam outgoing from the sample, the electron beam system comprising:

a first measuring section for finding a shape or coordinate values of the reference template held by the sample holder based on a stereo image of the reference template photographed by the electron beam detecting section while the reference template and the irradiated electron beam are tilted relative to each other by the sample tilting section;

a calibration data preparing section adapted to compare measurement results of the reference template by the first measuring section with known reference data on the reference template, to prepare calibration data for a stereo image photographed by the electron beam detecting section;

a calibration section for performing a calibration based on the calibration data so as to reduce aberration in an image of the sample detected by the electron beam detecting section;

a second measuring section for finding a shape or coordinate values of the sample based on a stereo image, photographed by the electron beam detecting section, of the sample placed in a tilt state made by the sample tilting section on the sample holder, the sample being calibrated by the calibration section; and an image display section for displaying a stereo image of the sample based on the electron beam detected by the electron beam detecting section.

4. The electron beam system according to claim 1, wherein the sample tilting section is configured to tilt the sample holder and the irradiated electron beam relative to each other in at least one of a first sample tilt mode where an irradiation direction of the electron beam irradiated by the electron optical system is changed with respect to the sample and a second sample tilt mode where the sample holder is tilted with respect to the electron beam.

5. The electron beam system according to claim 2, wherein the sample tilting section is configured to tilt the sample holder and the irradiated electron beam relative to each other in at least one of a first sample tilt mode where an irradiation direction of the electron beam irradiated by the electron optical system is changed with respect to the sample and a second sample tilt mode where the sample holder is tilted with respect to the electron beam.

6. The electron beam system according to claim 3, wherein the sample tilting section is configured to tilt the sample holder and the irradiated electron beam relative to each other in at least one of a first sample tilt mode where an irradiation direction of the electron beam irradiated by the electron optical system is changed with respect to the sample and a second sample tilt mode where the sample holder is tilted with respect to the electron beam.

7. The electron beam system according to claim 1, wherein the calibration data preparing section prepares calibration data on a tilt amount by the sample tilting section; and the calibration section calibrates the tilt amount by the sample tilting section.

8. The electron beam system according to claim 2, wherein the calibration data preparing section prepares calibration data on a tilt amount by the sample tilting section; and the calibration section calibrates the tilt amount by the sample tilting section.

9. The electron beam system according to claim 3, wherein the calibration data preparing section prepares calibration data on a tilt amount by the sample tilting section; and the calibration section calibrates the tilt amount by the sample tilting section.

10. The electron beam system according to claim 4, wherein the calibration data preparing section prepares calibration data on a tilt amount by the sample tilting section; and the calibration section calibrates the tilt amount by the sample tilting section.

11. The electron beam system according to claim 1, wherein the calibration data preparing section prepares calibration data on an irradiation direction of the electron beam irradiated by the electron optical system; and
the calibration section calibrates the irradiation direction of the electron beam irradiated by the electron optical system.

12. The electron beam system according to claim 2, wherein the calibration data preparing section prepares calibration data on an irradiation direction of the electron beam irradiated by the electron optical system; and
the calibration section calibrates the irradiation direction of the electron beam irradiated by the electron optical system.

13. The electron beam system according to claim 3, wherein the calibration data preparing section prepares calibration data on an irradiation direction of the electron beam irradiated by the electron optical system; and
the calibration section calibrates the irradiation direction of the electron beam irradiated by the electron optical system.

14. The electron beam system according to claim 4, wherein the calibration data preparing section prepares calibration data on an irradiation direction of the electron beam irradiated by the electron optical system; and
the calibration section calibrates the irradiation direction of the electron beam irradiated by the electron optical system.

15. The electron beam system according to claim 1, wherein the calibration data preparing section prepares calibration data on a magnification of the electron optical system; and the calibration section calibrates a scanning range of the electron optical system.

16. The electron beam system according to claim 2, wherein the calibration data preparing section prepares calibration data on a magnification of the electron optical system; and the calibration section calibrates a scanning range of the electron optical system.

17. The electron beam system according to claim 3, wherein the calibration data preparing section prepares calibration data on a magnification of the electron optical system; and the calibration section calibrates a scanning range of the electron optical system.

18. The electron beam system according to claim 4, wherein the calibration data preparing section prepares calibration data on a magnification of the electron optical system; and
the calibration section calibrates a scanning range of the electron optical system.

19. The electron beam system according to claim 1, wherein the calibration data preparing section prepares calibration data on distortion correction for the electron optical system; and
the calibration section calibrates a scanning direction of a scan coil of the electron optical system.

20. The electron beam system according to claim 2, wherein the calibration data preparing section prepares calibration data on distortion correction for the electron optical system; and
the calibration section calibrates a scanning direction of a scan coil of the electron optical system.

21. The electron beam system according to claim 3, wherein the calibration data preparing section prepares calibration data on distortion correction for the electron optical system; and
the calibration section calibrates a scanning direction of a scan coil of the electron optical system.

22. The electron beam system according to claim 4, wherein the calibration data preparing section prepares calibration data on distortion correction for the electron optical system; and
the calibration section calibrates a scanning direction of a scan coil of the electron optical system.

23. An electron beam measuring method, using an electron beam system including an electron beam source for emitting an electron beam, an electron optical system for irradiating the electron beam on a sample, a sample holder for holding the sample, a sample tilting section for tilting the sample holder and the irradiated electron beam relative to each other so that a stereo image can be acquired, and an electron beam detecting section for detecting an electron beam outgoing from the sample, wherein a computer is caused to perform:
a first measuring step of finding a shape or coordinate values of the reference template held by the sample holder based on a stereo image of the reference template photographed by the electron beam detecting section while the reference template and the irradiated electron beam are tilted relative to each other by the sample tilting section;
a calibration data preparing step of comparing measurement results of the reference template in the first measuring step with known reference data on the reference template, to prepare calibration data for a stereo image photographed by the electron beam detecting section;
a calibration step of performing a calibration based on the calibration data so as to reduce aberration in an image of the sample detected by the electron beam detecting section; and
a second measuring step of finding a shape or coordinate values of the sample based on a stereo image, photographed by the electron beam detecting section, of the sample placed in a tilt state made by the sample tilting section on the sample holder, the sample being calibrated in the calibration step.

24. An electron beam measuring method, using an electron beam system including an electron beam source for emitting an electron beam, an electron optical system for irradiating the electron beam on a sample, a sample holder for holding the sample, a sample tilting section for tilting the sample holder and the irradiated electron beam relative to each other so that a stereo image can be acquired, and an electron beam detecting section for detecting an electron beam outgoing from the sample, wherein a computer is caused to perform:
a first measuring step of finding a shape or coordinate values of the reference template held by the sample holder based on a stereo image of the reference template photographed by the electron beam detecting section while the reference template and the irradiated electron beam are tilted relative to each other by the sample tilting section;
a calibration data preparing step of comparing measurement results of the reference template in the first measuring step with known reference data on the reference template, to prepare calibration data for a stereo image photographed by the electron beam detecting section;
a calibration step of performing a calibration based on the calibration data so as to reduce aberration in an image of the sample detected by the electron beam detecting section;

a correction factor storing step of storing correction factors for a stereo image, photographed by the electron beam detecting section, for a plurality of tilt states made by the sample tilting section;

an approximate measurement step of finding an approximate shape or coordinate values of the sample based on a stereo image, photographed by the electron beam detecting section, of the sample placed in a tilt state made by the sample tilting section on the sample holder, the sample being calibrated in the calibration step;

an image correcting step of reading a correction factor corresponding to a tilt state in which the stereo image is photographed from the correction factors stored in the correction factor storing step and applying the correction factor to the shape or coordinate values of the sample found in the approximate measurement step to correct the stereo image; and a precise measurement step of finding a shape or coordinate values of the sample based on the stereo image corrected in the image correcting step.

25. An electron beam measuring method, using an electron beam system including an electron beam source for emitting an electron beam, an electron optical system for irradiating the electron beam on a sample, a sample holder for holding the sample, a sample tilting section for tilting the sample holder and the irradiated electron beam relative to each other so that a stereo image can be acquired, and an electron beam detecting section for detecting an electron beam outgoing from the sample, wherein a computer is caused to perform:

a first measuring step of finding a shape or coordinate values of the reference template held by the sample holder based on a stereo image of the reference template photographed by the electron beam detecting section while the reference template and the irradiated electron beam are tilted relative to each other by the sample tilting section;

a calibration data preparing step of comparing measurement results of the reference template in the first measuring step with known reference data on the reference template, to prepare calibration data for a stereo image photographed by the electron beam detecting section;

a calibration step of performing a calibration based on the calibration data so as to reduce aberration in an image of the sample detected by the electron beam detecting section;

a second measuring step of finding a shape or coordinate values of the sample based on a stereo image, photographed by the electron beam detecting section, of the sample placed in a tilt state made by the sample tilting section on the sample holder, the sample being calibrated in the calibration step; and an image displaying step of displaying a stereo image of the sample based on the electron beam detected by the electron beam detecting section.

26. An electron beam system, comprising:
an electron beam source for emitting an electron beam;
an electron optical system for irradiating the electron beam on a sample;
a sample holder for holding the sample;
a sample tilting section for tilting the sample holder and the irradiated electron beam relative to each other so that a stereo image can be acquired;
an electron beam detecting section for detecting an electron beam outgoing from the sample;

a third measuring section for finding a shape or coordinate values of the sample based on an output corresponding to the acquired stereo image in the tilt state made by the sample tilting section;

a first measuring step of finding a shape or coordinate values of the reference template, of which a shape or coordinate values are identified, held by the sample holder based on a signal corresponding to the stereo image outputted from the electron beam detecting section while the reference template and the irradiated electron beam are tilted relative to each other by the sample tilting section;

a correction factor storing section adapted to compare measurement results of the reference template by the first measuring section with the identified reference data on the reference template, to store a correction factor for a space other than a tilted surface to which the sample is tilted by the sample tilting section; and an image correcting section adapted to read a corresponding correction factor from the correction factor storing section to correct the image, wherein the third measuring section performs an approximate measurement step of finding an approximate shape or coordinate values of the sample based on the output corresponding to the stereo image from the electron beam detecting section, the image correcting section performs an image correcting step of reading a corresponding image correction factor from the correction factor storing section to correct the image based on the shape or coordinate values of the sample found in the approximate measurement step, and the third measuring section performs a precise measurement step of finding a shape or coordinate values of the sample based on the corrected stereo image corrected by the image correcting section.

27. An electron beam system, comprising:
an electron beam source for emitting an electron beam;
an electron optical system for converging the electron beam emitted from the electron beam source and irradiating the electron beam on a sample;
a detecting section for receiving an electron from the sample on which the electron beam is irradiated;
a sample holder for holding the sample;
a sample tilting section for tilting the electron beam irradiated on the sample held by the sample holder and the sample relative to each other; and
a data processing section adapted to receive, for each tilt angle, a signal detected by the detecting section receiving an electron from a reference sample having at least two tilted surfaces and held by the sample holder so as to be free in the relative tilt, to find a tilt angle of the reference sample based on an image of the two tilted surfaces and a reference dimension of the reference sample.

28. The electron beam system according to claim 27, wherein the data processing section is configured to further find a magnification of an image of the sample.

29. The electron beam system according to claim 27, wherein the data processing section is configured to find a correction factor for a tilt amount of the sample based on the found tilt angle, to correct the tilt angle based on the correction factor for the tilt amount of the sample.

30. The electron beam system according to claim 28, wherein the data processing section is configured to find a correction factor for a tilt amount of the sample based on the found tilt angle, to correct the tilt angle based on the correction factor for the tilt amount of the sample.

31. The electron beam system according to claim 29, wherein the data processing section is configured to find a correction factor for a tilt amount of the sample between tilt angles where a measurement is performed based on a plurality of found tilt angles, to correct a tilt amount of the sample for a tilt angle other than the tilt angles where a measurement is performed.

32. An electron beam system, comprising:
an electron beam source for emitting an electron beam;
an electron optical system for converging the electron beam emitted from the electron beam source and irradiating the electron beam on a sample;
a detecting section for receiving an electron from the sample on which the electron beam is irradiated;
a sample holder for holding the sample;
a sample tilting section for tilting the electron beam irradiated on the sample held by the sample holder and the sample relative to each other; and
a data processing section adapted to receive, for each tilt angle, a signal detected by the detecting section receiving an electron from a reference sample having at least two tilted surfaces and held by the sample holder so as to be free in the relative tilt, to perform a process of finding a tilt angle of the reference sample based on an image of the two tilted surfaces derived from an image of the sample in a position where little displacement in the electron optical system occurs due to tilting of the sample and a reference dimension of the reference sample, and a process of finding a correction factor based on a difference between a magnification in a neighboring image at the tilt angle and a magnification in an image according to the detected signal.

33. The electron beam system according to claim 27, wherein the sample tilting section is configured to perform either tilt control of the sample holder for allowing the sample to tilt relative to the electron beam, or deflection control of the electron beam for allowing the electron beam to be irradiated at different angle relative to the sample.

34. The electron beam system according to claim 32, wherein the sample tilting section is configured to perform either tilt control of the sample holder for allowing the sample to tilt relative to the electron beam, or deflection control of the electron beam for allowing the electron beam to be irradiated at different angle relative to the sample.

35. The electron beam system according to claim 32, wherein the data processing section includes an image forming section for forming an image of the sample in which electron lens distortion, scanning distortion, and/or the like are corrected using the correction factor and based on a signal from the electron beam detecting section.

36. The electron beam system according to claim 32, wherein the data processing section is configured to find by interpolation a correction factor for a tilt angle where a measurement is not performed in addition to a correction factor for a tilt angle where a measurement is performed.

37. A reference sample for use with the electron beam system according to claim 27, wherein the reference sample has a pattern including a bottom portion, a top portion, and a side surface portion connecting therebetween at a predetermined taper angle, where a dimension of a respective portion, an angle of the side surface portion and a height are known.

38. A reference sample for use with the electron beam system according to claim 32, wherein the reference sample has a pattern including a bottom portion, a top portion, and a side surface portion connecting therebetween at a predetermined taper angle, where a dimension of a respective portion, an angle of the side surface portion and a height are known.

39. The reference sample for use with the electron beam system according to claim 37, wherein the reference sample is configured with a line-and-space pattern.

40. The reference sample for use with the electron beam system according to claim 37, wherein the reference sample is formed with a line-and-space pattern in a direction perpendicular to a tilt direction of the sample.

* * * * *